United States Patent
Fu et al.

(10) Patent No.: US 10,920,269 B2
(45) Date of Patent: *Feb. 16, 2021

(54) AMPLIFICATION AND ANALYSIS OF SELECTED TARGETS ON SOLID SUPPORTS

(71) Applicant: Affymetrix, Inc., Carlsbad, CA (US)

(72) Inventors: Glenn K. Fu, Dublin, CA (US); Glenn H. Mcgall, Palo Alto, CA (US); Robert G. Kuimelis, Palo Alto, CA (US); Jing Hu, San Jose, CA (US); Pei-Hua Wang, Fremont, CA (US)

(73) Assignee: AFFYMETRIX, INC., Carlsbad, CA (US)

( * ) Notice: Subject to any disclaimer, the term of this patent is extended or adjusted under 35 U.S.C. 154(b) by 128 days.

This patent is subject to a terminal disclaimer.

(21) Appl. No.: 15/959,683

(22) Filed: Apr. 23, 2018

(65) Prior Publication Data

US 2019/0002965 A1  Jan. 3, 2019

Related U.S. Application Data

(63) Continuation of application No. 14/269,234, filed on May 5, 2014, now Pat. No. 9,982,293, which is a (Continued)

(51) Int. Cl.
*C40B 30/04* (2006.01)
*C12Q 1/6837* (2018.01)
(Continued)

(52) U.S. Cl.
CPC ......... *C12Q 1/6837* (2013.01); *C12Q 1/6844* (2013.01); *C12Q 1/6858* (2013.01);
(Continued)

(58) Field of Classification Search
None
See application file for complete search history.

(56) References Cited

U.S. PATENT DOCUMENTS

| 4,582,788 A | 4/1986 | Erlich |
| 4,683,194 A | 7/1987 | Saiki et al. |

(Continued)

FOREIGN PATENT DOCUMENTS

| EP | 0684315 B1 | 6/2002 |
| EP | 1634963 A1 | 3/2006 |

(Continued)

OTHER PUBLICATIONS

Adessi et al., "Solid Phase DNA Amplification: characterisation of primer attachment and amplification mechanisms", Nucleic Acids Research, vol. 28, No. 20, e87, 2000, 1-8.
Baner et al. (1998) "Signal amplification of padlock probes by rolling circle replication," Nucleic Acids Res. 26(22):5073-5078.
Barany, et al., "Genetic Disease Detection and DNA Amplification Using Cloned Thermostable Ligase", Proceedings of the National Academy of Sciences, vol. 88, Issue 1, 1991, 189-193.
(Continued)

*Primary Examiner* — Christian C Boesen
(74) *Attorney, Agent, or Firm* — Affymetrix, Inc.; Jinhee Chang

(57) ABSTRACT

Methods are provided for multiplexed amplification of selected targets and analysis of the amplified targets. In preferred aspects the amplification and analysis take place on the same solid support and preferably in a localized area such as a bead or a feature of an array. Targets are circularized by hybridization to probes followed by ligation of the ends of the target to form a closed circle. The targets are then used as template for extension of an array bound probe resulting in extended probes having multiple copies of the target. The extended probes can then be analyzed. The methods may be used for genotyping, sequencing and analysis of copy number.

17 Claims, 24 Drawing Sheets

Specification includes a Sequence Listing.

Related U.S. Application Data continuation of application No. 12/899,540, filed on Oct. 6, 2010, now Pat. No. 8,716,190, and a continuation-in-part of application No. 12/211,100, filed on Sep. 15, 2008, now Pat. No. 9,388,457, said application No. 12/899,540 is a continuation-in-part of application No. 12/211,100, filed on Sep. 15, 2008, now Pat. No. 9,388,457.

(60) Provisional application No. 61/249,242, filed on Oct. 6, 2009, provisional application No. 60/972,548, filed on Sep. 14, 2007, provisional application No. 60/972,410, filed on Sep. 14, 2007.

(51) Int. Cl.
*C12Q 1/6844* (2018.01)
*C12Q 1/6858* (2018.01)
*C12Q 1/6874* (2018.01)
*C12Q 1/6876* (2018.01)
*C40B 50/06* (2006.01)

(52) U.S. Cl.
CPC ......... *C12Q 1/6874* (2013.01); *C12Q 1/6876* (2013.01); *C12Q 2600/106* (2013.01); *C12Q 2600/154* (2013.01); *C12Q 2600/156* (2013.01); *C40B 30/04* (2013.01); *C40B 50/06* (2013.01)

(56) References Cited

U.S. PATENT DOCUMENTS

| | | |
|---|---|---|
| 5,102,784 A | 4/1992 | George, Jr. |
| 5,455,166 A | 10/1995 | Walker |
| 5,545,522 A | 8/1996 | Van Gelder et al. |
| 5,547,839 A | 8/1996 | Dower et al. |
| 5,554,516 A | 9/1996 | Kacian et al. |
| 5,641,658 A | 6/1997 | Adams et al. |
| 5,648,211 A | 7/1997 | Fraiser et al. |
| 5,716,785 A | 2/1998 | Van Gelder et al. |
| 5,744,311 A | 4/1998 | Fraiser et al. |
| 5,800,992 A | 9/1998 | Fodor et al. |
| 5,824,517 A | 10/1998 | Cleuziat et al. |
| 5,871,928 A | 2/1999 | Fodor et al. |
| 5,925,525 A | 7/1999 | Fodor et al. |
| 5,935,793 A | 8/1999 | Wong |
| 6,013,440 A | 1/2000 | Lipshutz et al. |
| 6,013,449 A | 1/2000 | Hacia et al. |
| 6,040,138 A | 3/2000 | Lockhart et al. |
| 6,060,288 A | 5/2000 | Adams et al. |
| 6,110,667 A | 8/2000 | Lopez-Nieto et al. |
| 6,114,149 A | 9/2000 | Fry et al. |
| 6,132,997 A | 10/2000 | Shannon |
| 6,251,639 B1 | 6/2001 | Kurn et al. |
| 6,258,539 B1 | 7/2001 | Hunkapiller et al. |
| 6,258,568 B1 | 7/2001 | Nyren et al. |
| 6,300,070 B1 | 10/2001 | Boles et al. |
| 6,329,150 B1 | 12/2001 | Lizardi et al. |
| 6,344,329 B1 | 2/2002 | Lizardi |
| 6,361,947 B1 | 3/2002 | Dong et al. |
| 6,632,611 B2 | 10/2003 | Su et al. |
| 6,638,717 B2 | 10/2003 | Perrin et al. |
| 6,686,156 B2 | 2/2004 | Kurn |
| 6,692,918 B2 | 2/2004 | Kurn |
| 6,858,413 B2 | 2/2005 | Kurn |
| 6,872,529 B2 | 3/2005 | Su |
| 6,958,225 B2 | 10/2005 | Dong |
| 7,108,976 B2 | 9/2006 | Jones et al. |
| 7,115,400 B1 | 10/2006 | Adessi et al. |
| 7,202,039 B2 | 4/2007 | Su |
| 7,208,295 B2 | 4/2007 | Faham et al. |
| 7,214,490 B2 | 5/2007 | Su et al. |
| 7,267,966 B2 | 9/2007 | Dong et al. |
| 7,351,557 B2 | 4/2008 | Kurn |
| 7,425,431 B2 | 9/2008 | Church et al. |
| 7,452,671 B2 | 11/2008 | Shapero et al. |
| 7,459,273 B2 | 12/2008 | Jones et al. |
| 7,510,829 B2 | 3/2009 | Faham et al. |
| 7,745,178 B2 | 6/2010 | Dong |
| 7,771,934 B2 | 8/2010 | Kurn |
| 7,822,555 B2 | 10/2010 | Huang et al. |
| 7,858,304 B2 | 12/2010 | Baker et al. |
| 7,862,999 B2 | 1/2011 | Zheng et al. |
| 2003/0232348 A1 | 12/2003 | Jones et al. |
| 2004/0110153 A1 | 6/2004 | Dong et al. |
| 2004/0115644 A1 | 6/2004 | Dong |
| 2005/0009059 A1 | 1/2005 | Shapero et al. |
| 2005/0037356 A1 | 2/2005 | Gullberg et al. |
| 2005/0064476 A1 | 3/2005 | Huang et al. |
| 2005/0153347 A1 | 7/2005 | Shapero et al. |
| 2006/0073511 A1 | 4/2006 | Jones et al. |
| 2006/0292585 A1 | 12/2006 | Nautiyal et al. |
| 2007/0003949 A1 | 1/2007 | Rava |
| 2007/0020639 A1 | 1/2007 | Shapero |
| 2007/0048756 A1 | 3/2007 | Mei et al. |
| 2007/0207482 A1 | 9/2007 | Church et al. |
| 2008/0057499 A1 | 3/2008 | Fu |
| 2008/0199916 A1 | 8/2008 | Zheng et al. |
| 2008/0254453 A1 | 10/2008 | Shapero et al. |
| 2008/0293589 A1 | 11/2008 | Shapero |
| 2009/0075345 A1 | 3/2009 | Shapero et al. |
| 2009/0176234 A1 | 7/2009 | Drmanac et al. |
| 2010/0292097 A1 | 11/2010 | Dong |

FOREIGN PATENT DOCUMENTS

| | | |
|---|---|---|
| EP | 1590477 B1 | 7/2009 |
| EP | 1594980 B1 | 11/2009 |
| WO | WO-9210587 A1 | 6/1992 |
| WO | WO-9925873 A1 | 5/1999 |

OTHER PUBLICATIONS

Barringer et al., "Blunt-end and single-strand ligations by *Escherichia coli* ligase: influence on an in vitro amplication scheme," Gene, 89(1): 117-122 (1990).

Bentley, "Whole-genome re-sequencing," Current Opinion in Genetics & Development, 16(6) 545-552 (2006).

Bloomfield, "DNA condensation," Current Opinion in Structural Biology, 6(3): 334-341 (1996).

Brownie et al., "The elimination of primer-dimer accumulation in PCR," Nucleic Acids Research, 25(16): 3235-3241 (1997).

Chen and Ruffner, "Amplification of closed circular DNA in vitro," Nucleic Acids Research, 26(23): 1126-1127 (1998).

Chen et al., "A Microsphere-Based Assay for Multiplexed Single Nucleotide Polymorphism Analysis Using Single Base Chain Extension," Genome Research, 10(4):549-557 (2000).

Dahl F et al. (2005) Multiplex amplification enabled by selective circularization of large sets of genomic DNA fragments. Nucleic Acids Res. 33, e71.

Erratum for Margulies, et al. Genome sequencing in microfabricated high-density picolitre reactors. Nature. 2005;437(7057):376-80.: Margulies, et al. Nature. 441(7089):120. (May 4, 2006).

Faham et al., "Multiplexed variation scanning for 1,000 amplicons in hundreds of patients using mismatch repair detection (MRD) on tag arrays," Proc. Natl. Acad. Sci., 102(41): 14717-14722 (2005).

Fang and Hoh, "Surface-directed DNA condensation in the absence of soluble multivalent cations," Nucleic Acids Research, 26(2): 588-593 (1998).

Faruqi et al., "High-throughput genotyping of single nucleotide polymorphisms with rolling circle amplification," BMC Genomics, 2:4 {2001).

Fields, "Molecular biology:Site-seeing by Sequencing,"Science, 316(5830): 1441-1442 (2007).

Fire, et al, "Rolling Replication of Short DNA Circles", Proc. Natl. Acad. Sci., (1995) vol. 92, No. 10, pp. 4641-4645.

Fredriksson et al., "Multiplex amplification of all coding sequences within 10 cancer genes by Gene-Collector," Nucleic Acids Research, 35(7): e47 (2007).

(56) References Cited

OTHER PUBLICATIONS

Frohman, Michael A. et al., "Rapid production of full-length cDNAs from rare transcripts: amplification using a single gene-specific oligonucleotide primer,", Proceedings of the National Academy of Sciences, Biochemistry, vol. 85,, Dec. 1988, 8998-9002.

Guatelli et al, Isothermal in vitro amplification of nucleic acids by a multienzyme reaction modeled after retroviral replication, Proc. Natl Acad. Sci USA, vol. 87, 1874-1878, (Mar. 5, 1990).

Hafner et al., "Isothermal amplification and multimerization of DNA by Bst DNA polymerase," BioTechniques, 30(4): 852-867 (2001).

Hatch et al., "Rolling circle amplification of DNA immobilized on solid surfaces and its application to multiplex mutation detection," Genetic Analysis: Biomolecular Engineering, 15(2): 35-40 (Apr. 1999).

Huse et al., "Accuracy and quality of massively parallel DNA pyrosequencing," Genome Biology, 8(7):R143.1-R143.9 (2007).

Ju, et al., "Four-color DNA sequencing by synthesis using cleavable fluorescent nucleotide reversible terminators," Proceedings of the National Academy of Sciences of USA, vol. 103, No. 52, pp. 19635-19640 (2006).

Kennedy et al., "Large-scale Genotyping of Complex DNA," Nature Biotechnology, vol. 21 (10), pp. 1233-1237 (Oct. 2003).

Kim et al., "Isolation of human Dna2 endonuclease and characterization of its enzymatic properties," Nucleic Acids Research, 34(6): 1854-1864 (2006).

Kurn et al., "Novel isothermal, Linear Nucleic Acid Amplification Systems for Highly Multiplexed Applications," Clinical Chemistry, 51: 1973-1981 (2005).

Kwoh, et al., "Transcription-Based Amplification System and Detection of Amplified Human Immunodeficiency Virus Type 1 With a Bead-Based Sandwich Hybridization Format", Proceedings of the National Academy of Sciences (PNAS), vol. 86, Issue 4, Feb. 15, 1989, 1173-1177.

Leamon et al., "High-throughput, massively parallel DNA sequencing technology for the era of personalized medicine," Gene Therapy and Regulation, 3(1): 15-31 (2007).

Lizardi et al., "Exponential Amplification of Recombinant-RNA Hybridization Probes," Nature Biotechnology, 6: 1197-1202 (1988).

Lizardi et al. Mutation detection and single-molecule counting using isothermal rolling-circle amplification. Nature Genetics 19 (1998) 225-232.

Lockhart, et al., "Expression Monitoring by Hybridization to High-Density Oligoncleotide Arrays", Nature Biotechnology, vol. 14, 1996, 1675-1680.

Lyamichev, Victor et al., "Structure-Specific Endonucleolytic Cleavage of Nucleic Acids by Eubacterial DNA Polymerases", Science, vol. 260 , Association for the Advancement of Science, May 7, 1993, 778-783.

Matsuzaki et al., "Genotyping of over 100,000 SNPs on a pair of oligonucleotide arrays," Nature methods 1 (2) : 109-111 (2004).

Mullis, K. et al., "Specific Enzymatic Amplification of DNA in Vitro: The Polymerase Chain Reaction", Cold Spring Harbor Symposia on Quantitative Biology, vol. 51, Cold Spring Harbor Laboratory Press, 1986, 263-273.

Nallur et al., "Signal amplification by rolling circle amplification on DNA microarrays," Nucleic Acids Research, 29(23): e118 (2001).

Nilsson et al., "Analyzing genes using closing and replicating circles" Trends in Biotechnology, 24{2): 83-88 {2006).

Nilsson et al., "Making ends meet in genetic analysis using padlock probes" Human Mutation, 19{4): 410-415 {2002).

Office Action issued for corresponding U.S. Appl. No. 12/211,100, dated Dec. 30, 2013.

Office Action issued for corresponding U.S. Appl. No. 12/211,100, dated Jun. 27, 2014.

Pickering et al., "Integration of DNA ligation and rolling circle amplification for the homogeneous, end-point detection of single nucleotide polymorphisms," Nucleic Acids Research, 30(12): e60 (2002).

Pihlak, et al. Rapid genome sequencing with short universal tiling probes. Nature Biotechnology, 26: 676-684 (2008).

Qi et al., "L-RCA {ligation-rolling circle amplification): a general method for genotyping of single nucleotide polymorphisms {SNPs)" Nucleic Acids Research, 29{22): e116 {2001).

Randall K. Saiki et al., "Enzymatic Amplification of .beta.-Globin Genomic Sequences and Restriction Site Analysis for Diagnosis of Sickle Cell Anemia", Science, Dec. 20, 1985, pp. 1350-1354, vol. 230.

Robertson et al., "Genome-wide profiles of STA T1 DNA association using chromatin immunoprecipitation and massively parallel sequencing" Nature Methods, 4{8): 651-657 {2007).

Rubina et al., "Hydrogel-based protein microchips: manufacturing, properties, and applications," BioTechniques, 34(5): 1008-1022 (2003).

Shapero MH et al. (2004) MARA: a novel approach for highly multiplexed locus-specific SNP genotyping using high-density DNA oligonucleotide arrays. Nucleic Acids Res. 32(22): e181.

Shapero, Michael et al., "SNP Genotyping by Multiplexed Solid-Phase Amplification and Fluorescent Minisequencing", Genome Research, 11, 2001, 1926-1934.

Shendure et al, Accurate Multiplex Polony Sequencing of an Evolved Bacterial Genome, Seience, Sep. 2005, vol. 309, No. 5741, pp. 1728-1732.

Lin, Z et al., "Multiplex Genotype Determination at a Large Number of Gene Loci", Proceedings of the National Academy of Sciences of the United States, vol. 93, No. 6, Genetics, USA, Mar. 1996, 2582-2587.

Stenberg et al., "PieceMaker: selection of DNA fragments for selector-guided multiplex amplification," Nucleic Acids Research, 33(8): e72 (2005).

Stewart et al. Flap endonuclease disengages Dna2 helicase/nuclease from Okazaki fragment flaps. J. Biol. Chem. (2006) vol. 281, No. 50, pp. 38565-38572.

Stewart et al., "Significance of the dissociation of Dna2 by flap endonuclease 1 to Okazaki fragment processing in *Saccharomyces cerevisiae*," The Journal of Biological Chemistry, 284(13): 8283-8289 (2009).

Syvanen, "From gels to chips: minisequencing primer extension for analysis of point mutations and single nucleotide polymorphisms," Human Mutation, 13(1): 1-10 (1999).

Thomas et al., "Amplification of padlock probes for DNA diagnostics by cascade rolling circle amplification or the polymerase chain reaction," Archives of Pathology and Laboratory Medicine, 123(12): 1170-1176 (1999).

Vasiliskov et al., "Fabrication of Microarray of Gel-Immobilized Compounds on a Chip by Copolymerization," BioTechniques, 27(3): 592-606 (1999).

Voisey et al., "Interrogation of multimeric DNA amplification products by competitive primer extension using Bst DNA polymerase (large fragment)," BioTechniques, 31(5): 1122-1129 (2001).

Walker et al., "Isothermal in vitro amplification of DNA by restriction enzyme I DNA polymerase system," Proceedings of the National of Academy of Sciences, vol. 89, 1992, 392-396.

Walker et al, Strand Displacement amplification—an isothermal, in vitro DNA amplification technique, Nucleic Acids Research, vol. 20, No. 7, 1992, 1691-1696.

Wang et al., "A genotyping system capable of simultaneously analyzing> 1000 single nucleotide polymorphisms in a haploid genome," Genome Research, 15: 276-283 (2005).

Westin, Lorelei et al., "Anchored multiplex amplification on a microelectronic chip array", Nature Biotechnology, vol. 18, Feb. 2000, pp. 199-204.

Wu et al, The Ligation Amplification Reaction (LAR)—Amplification of Specific DNA Sequences Using Sequential Rounds of Template-Dependent Litigation, Genomics 4, (1988 & 1989), 560-569.

Wu, J et al., "Termination of DNA synthesis by N6-alkylated, not 3'-O-alkylated, photocleavable 2'—deoxyadenosine triphosphates", Nuc Acids Research, vol. 35(19), 2007, pp. 6339-6349.

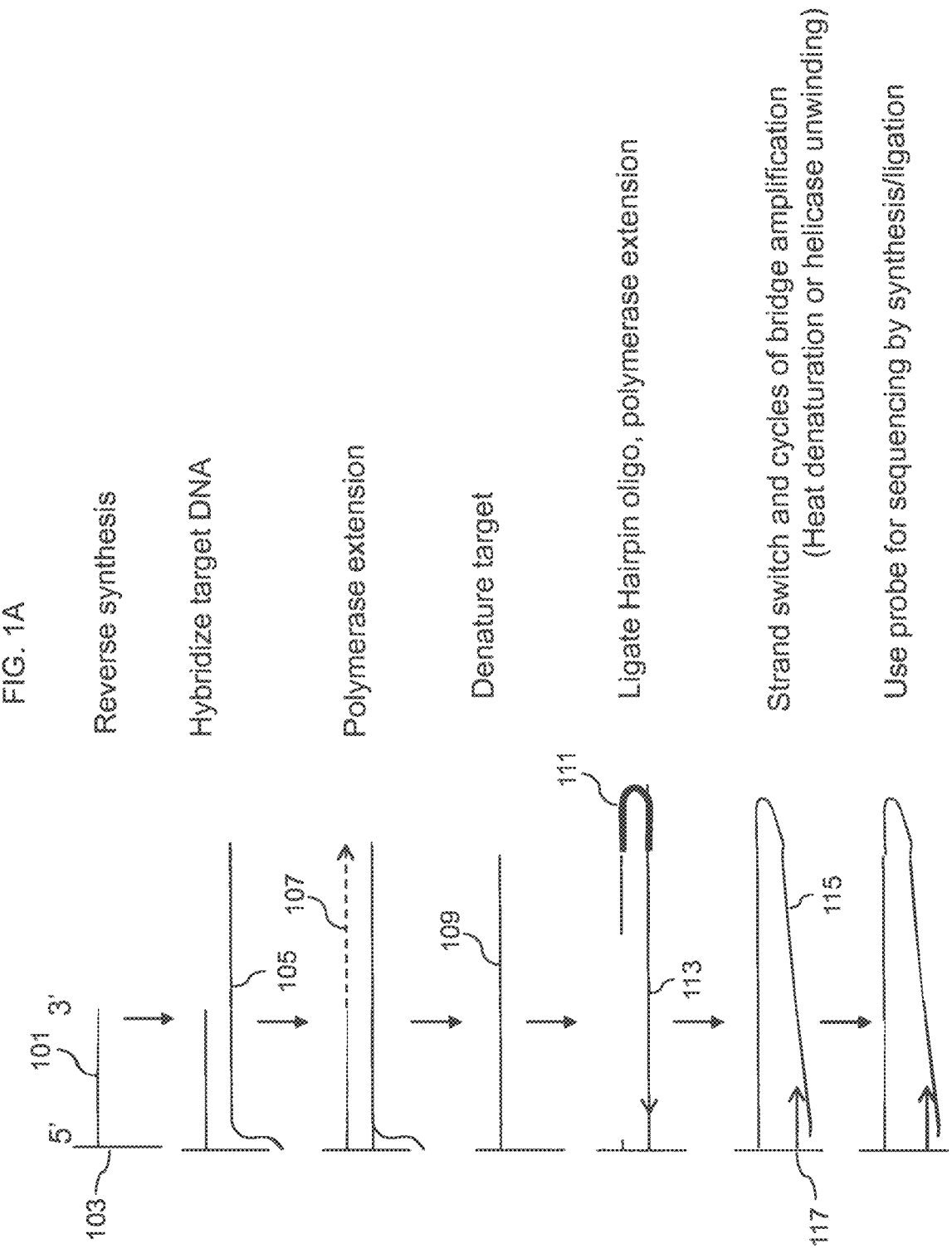

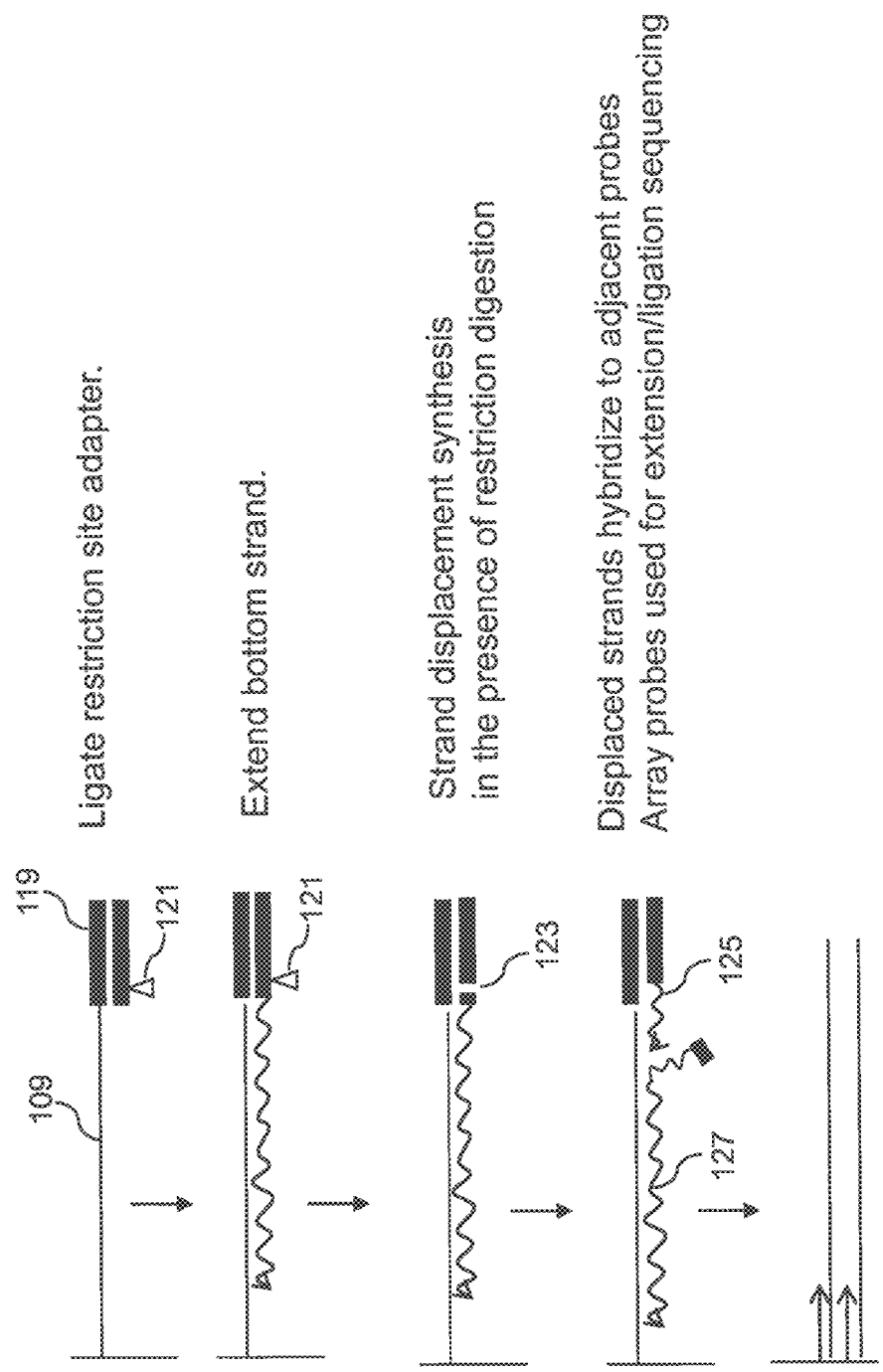

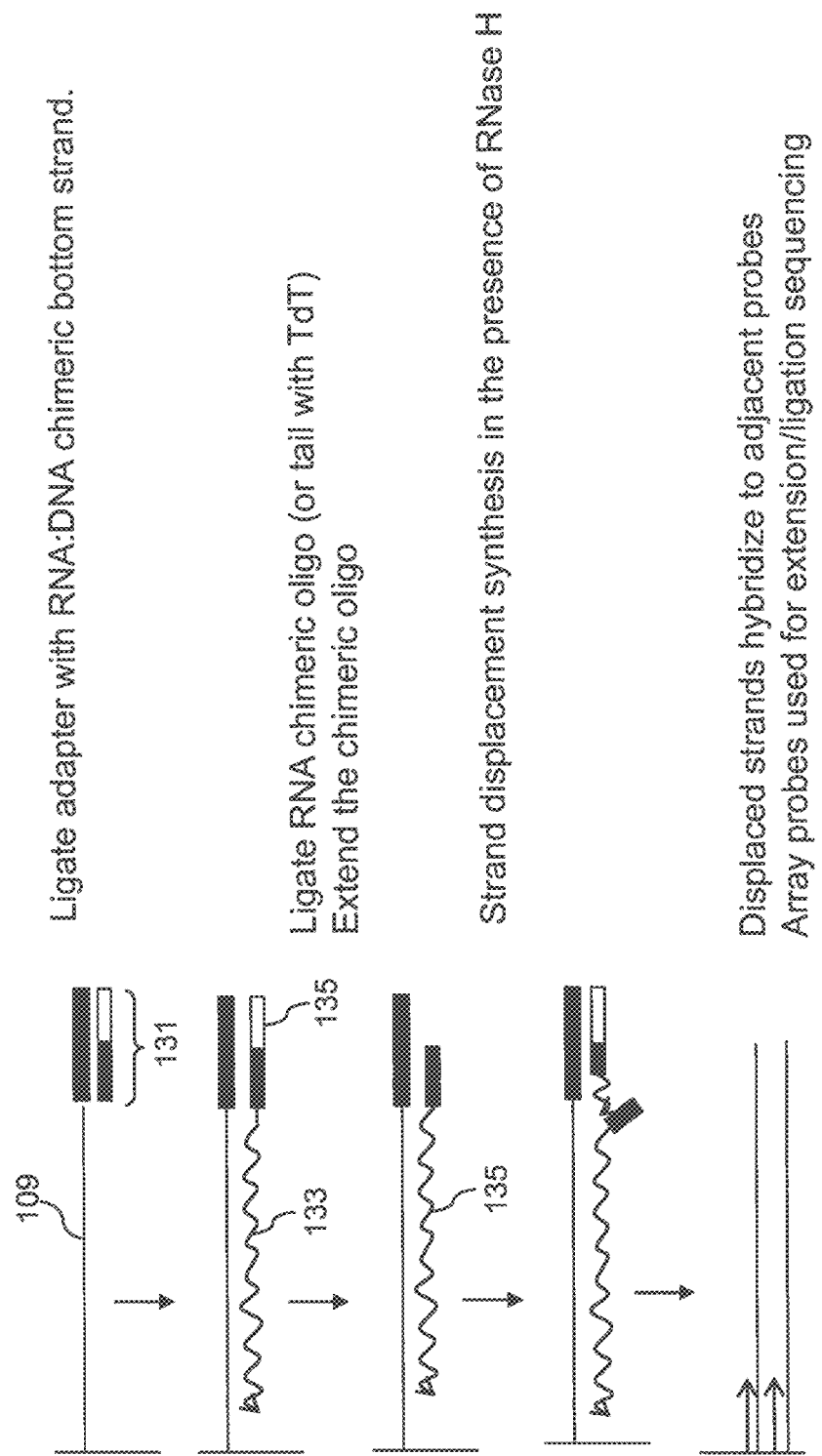

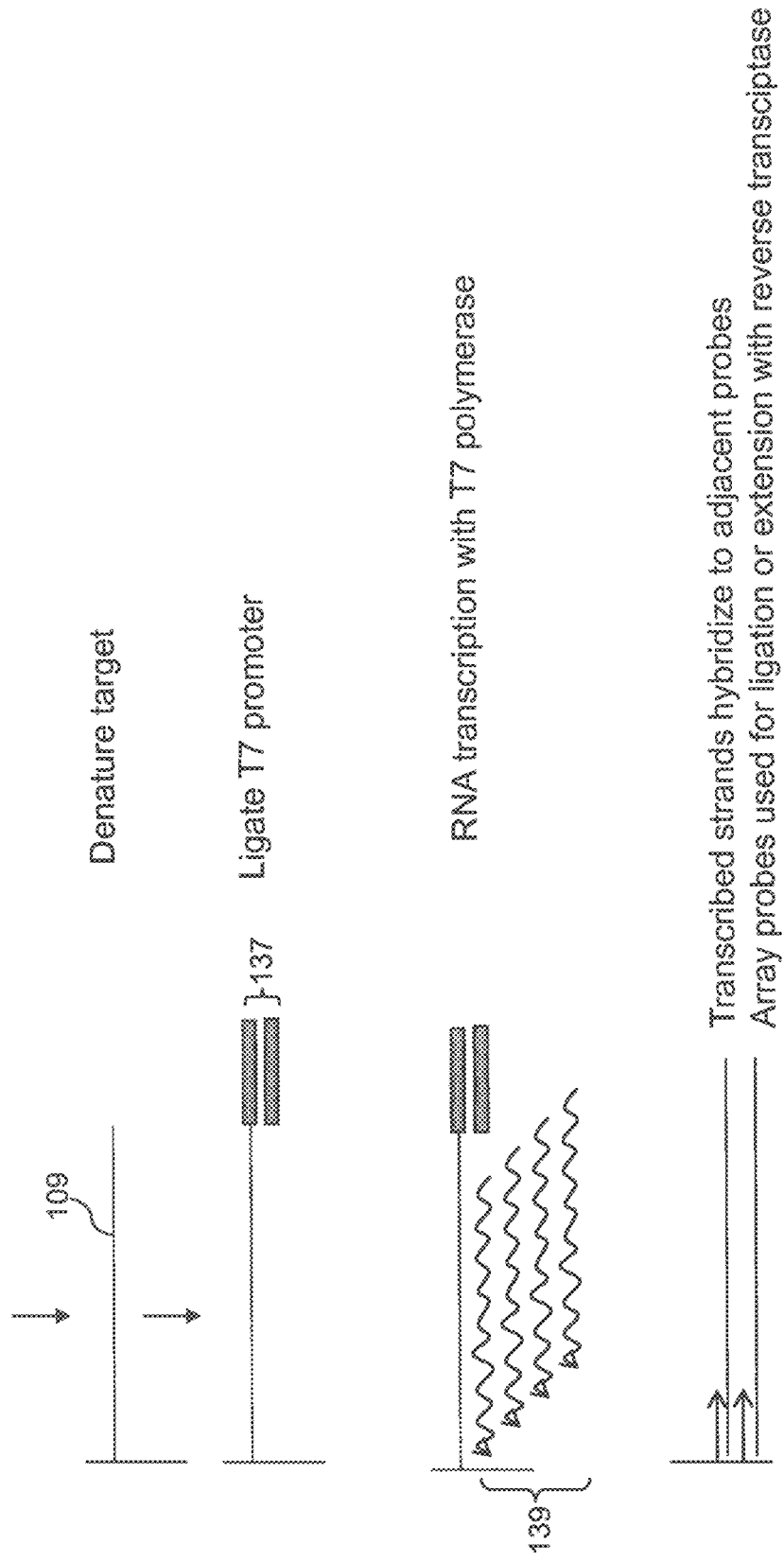

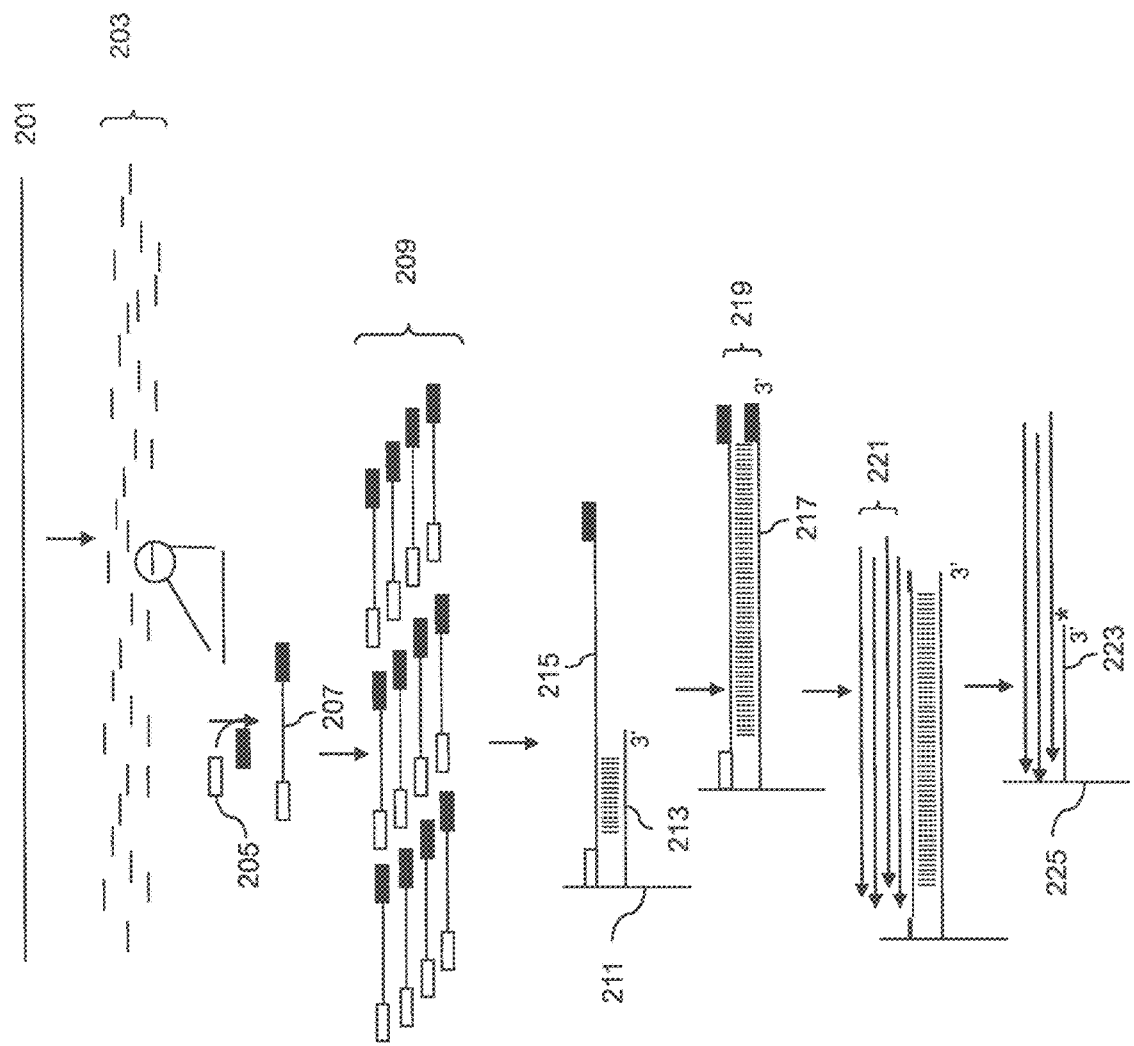

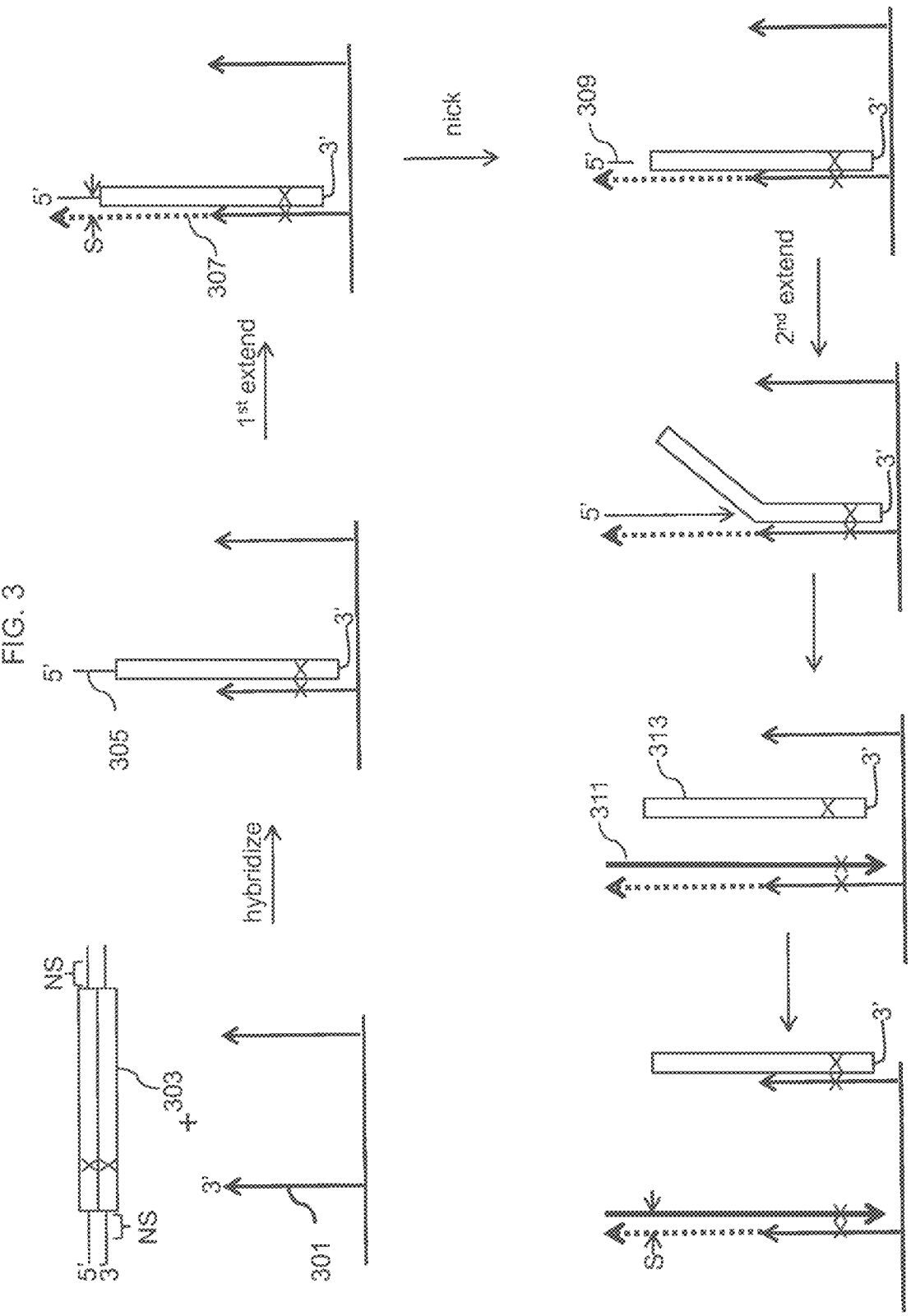

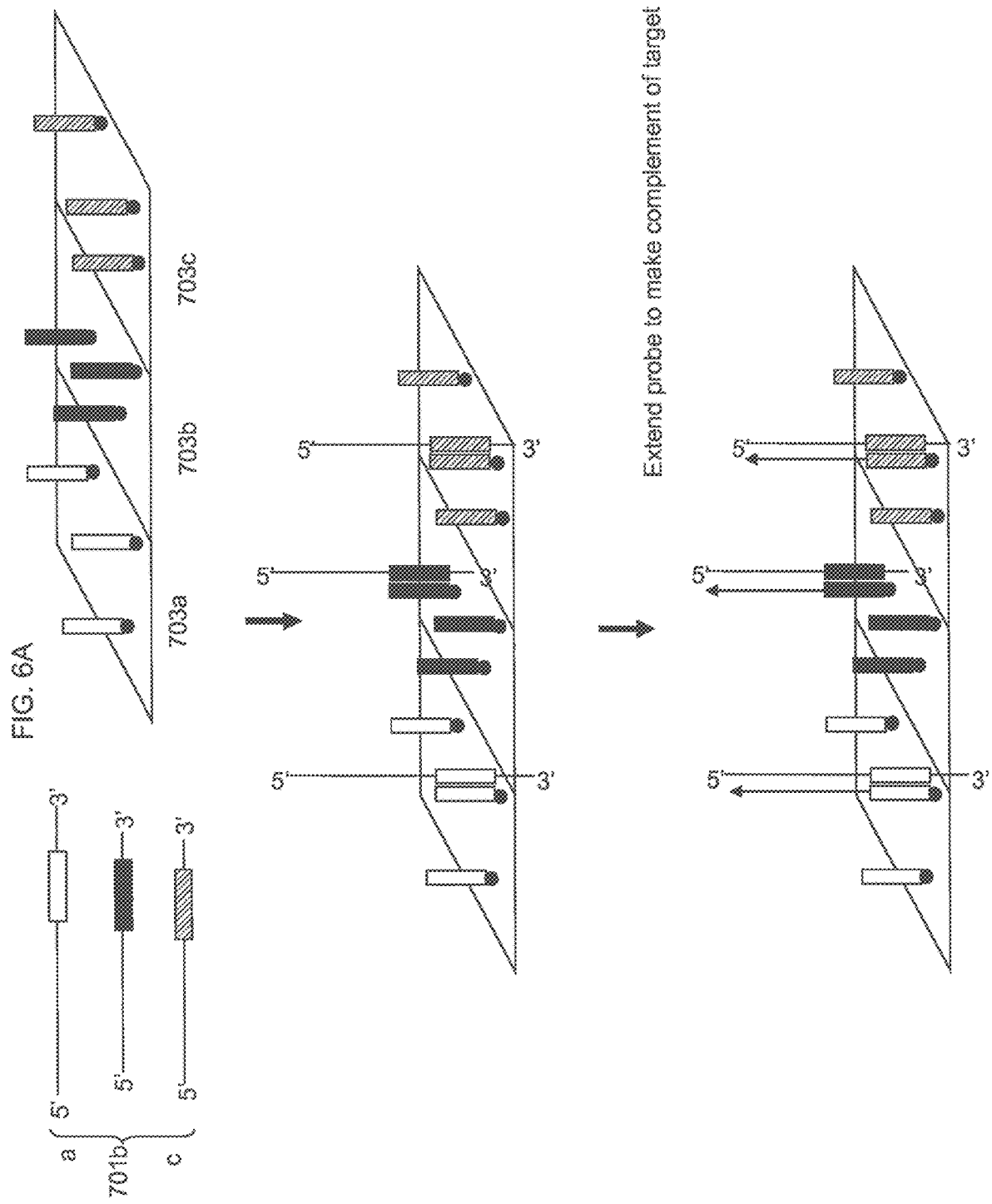

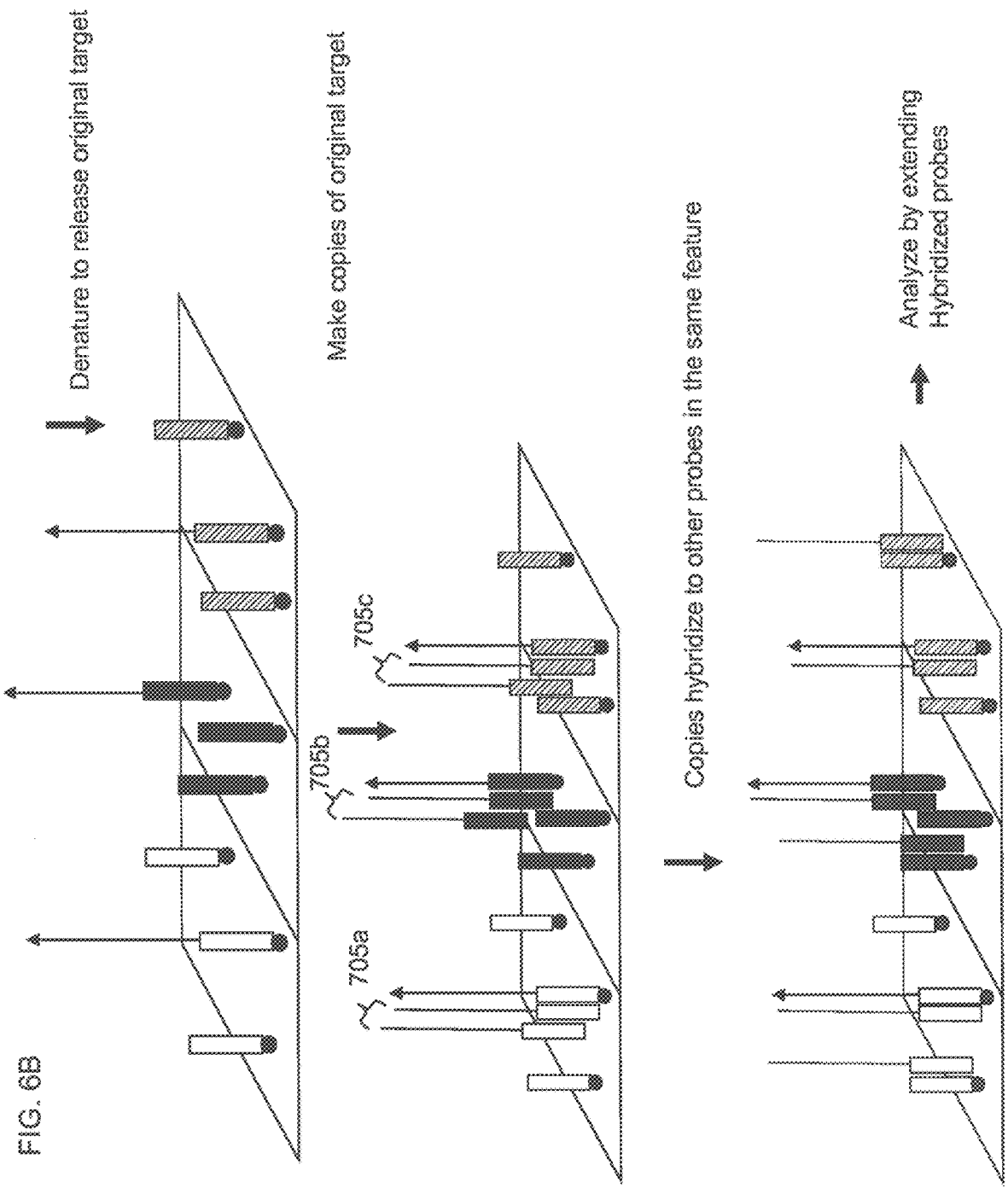

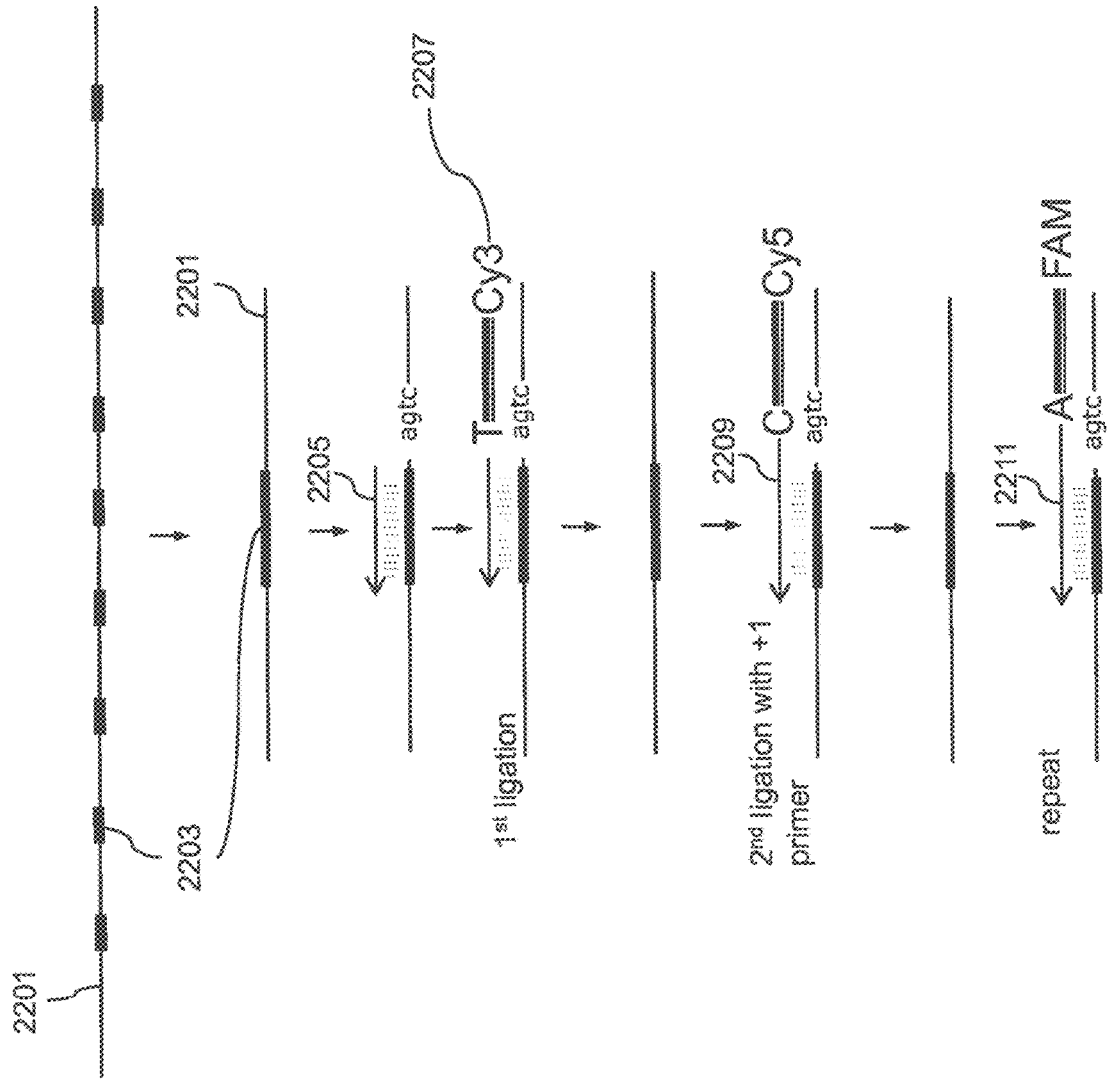

SEQUENCE LISTING

```
<160> NUMBER OF SEQ ID NOS: 7

<210> SEQ ID NO 1
<211> LENGTH: 24
<212> TYPE: DNA
<213> ORGANISM: Artificial
<220> FEATURE:
<223> OTHER INFORMATION: primer

<400> SEQUENCE: 1
uaaucauggu acugcatttt tttt                                          24

<210> SEQ ID NO 2
<211> LENGTH: 24
<212> TYPE: DNA
<213> ORGANISM: Artificial
<220> FEATURE:
<223> OTHER INFORMATION: extended probe

<400> SEQUENCE: 2
aaaaaaaatg cagtaccatg atta                                          24

<210> SEQ ID NO 3
<211> LENGTH: 32
<212> TYPE: DNA
<213> ORGANISM: Artificial
<220> FEATURE:
<223> OTHER INFORMATION: adaptor sequence
<220> FEATURE:
<221> NAME/KEY: misc_feature
<222> LOCATION: (16)..(17)
<223> OTHER INFORMATION: wherein n is g, a, t or c

<400> SEQUENCE: 3
gtccttagcc agttanngtc ccaggaaatc cg                                 32
```

```
<210> SEQ ID NO 4
<211> LENGTH: 31
<212> TYPE: DNA
<213> ORGANISM: Artificial
<220> FEATURE:
<223> OTHER INFORMATION: adaptor sequence
<220> FEATURE:
<221> NAME/KEY: misc_feature
<222> LOCATION: (16)..(17)
<223> OTHER INFORMATION: wherein n is g, a, t or c

<400> SEQUENCE: 4
caggaatcgg tcaatnncag ggtcctttag g                               31

<210> SEQ ID NO 5
<211> LENGTH: 31
<212> TYPE: DNA
<213> ORGANISM: Artificial
<220> FEATURE:
<223> OTHER INFORMATION: target sequence
<220> FEATURE:
<221> NAME/KEY: misc_feature
<222> LOCATION: (16)..(16)
<223> OTHER INFORMATION: wherein n is g, a, t or c

<400> SEQUENCE: 5
gtacctctcc atcctnctga tcctgtacct c                               31

<210> SEQ ID NO 6
<211> LENGTH: 32
<212> TYPE: DNA
<213> ORGANISM: Artificial
<220> FEATURE:
<223> OTHER INFORMATION: array probe

<400> SEQUENCE: 6
aggatggaga ggtacgaggt acacaggatc ag                              32

<210> SEQ ID NO 7
<211> LENGTH: 70
<212> TYPE: DNA
<213> ORGANISM: Artificial
<220> FEATURE:
<223> OTHER INFORMATION: probe sequence

<400> SEQUENCE: 7
gtcgtcaaga tgctaccgtt caggattaga ttatcatact gggctatcgc aacacaacca    60
cctctgccga                                                           70
```

AMPLIFICATION AND ANALYSIS OF SELECTED TARGETS ON SOLID SUPPORTS

RELATED APPLICATIONS

This application is a Continuation of U.S. patent application Ser. No. 14/269,234 filed on May 5, 2014 now U.S. Pat. No. 9,982,293 issued on May 29, 2018, which is a Continuation of U.S. application Ser. No. 12/899,540 filed on Oct. 6, 2010 now U.S. Pat. No. 8,716,190 issued on May 6, 2014, which claims priority to U.S. patent application Ser. No. 12/899,540 filed Oct. 6, 2010 which claims priority to U.S. Provisional application No. 61/249,242 filed Oct. 6, 2009, and is a continuation-in-part of U.S. patent application Ser. No. 12/211,100 filed Sep. 15, 2008 now U.S. Pat. No. 9,388,457 issued Jul. 12, 2016, which claims priority to U.S. Provisional Application Nos. 60/972,410 and 60/972,548, both filed Sep. 14, 2007, the entire disclosures of which are incorporated herein by reference in their entireties.

FIELD OF THE INVENTION

The methods of the invention relate generally to amplification of nucleic acid on a solid support and analysis of the amplified nucleic acid.

BACKGROUND OF THE INVENTION

There is currently a significant amount of interest in the next generation sequencing technologies that are being commercialized. Presently the commercial offerings range from systems that claim to achieve from 40 to 100 MB of sequence information in a single run, up to about 1 to almost 2 GB of assembled sequences in a single run.

A feature of several of the recent commercial offerings is a solid phase single molecule clonal amplification procedure based either on bead emulsion PCR, or on bridge PCR. This clonal amplification enables a single DNA molecule to be amplified on solid phase, which physically separates one molecule from another. After amplification, these distinct clusters of DNA are then subject to repeated cycles of ligation or reversible single base chain terminated extension. During these reactions, separate labeling with 4 florophores or haptens, one for each of the 4 DNA bases, allows for the identification of the incorporated base at any given position. Repeated cycles generate short fragments of DNA sequence which can then be assembled into a larger continuous length of finished sequence. The DNA sequencing approach is therefore random and currently does not specifically sample any targeted regions of interest.

SUMMARY OF THE INVENTION

Specific hybridization can be achieved by direct synthesis of the DNA sequences of interest on arrays. The methods disclosed herein enable solid phase clonal amplification of hybridized target molecules on the surface of probe arrays, after hybridization of target to complementary probes on the array. Such clonally amplified DNAs can serve as a template for a variety of analytical reactions including sequencing of a portion of the target. This approach allows for the locus specific targeting of sequencing in only regions of interest and reduces the overwhelming redundancies required with other random sampling methods.

Methods for solid phase clonal amplification of hybridized target molecules on the surface of arrays of short oligonucleotides of known sequence and location are disclosed. In preferred embodiments an array of probes complementary to a plurality of sequences of interest are hybridized to targets. The targets of interest are then amplified in a defined location so that many copies of the same target sequence are generated in a single location. The amplified target is then analyzed, for example, by sequencing by synthesis or sequencing by ligation. The methods may also be used for quantitative analysis of expression levels of RNA. Methods for the locus specific targeting of sequencing or analysis of regions of interest are disclosed. In preferred aspects the methods reduce the requirements for analysis of redundant sequences relative to that of methods that employ random sampling methods.

In many of the embodiments the methods include amplifying a target to make many copies and then analyzing the copies. Targets are amplified in a feature to which the target hybridizes through a target specific interaction between a probe in the feature and the target. The target:probe interaction is specific so a known target is amplified at each feature. The amplified targets may be covalently attached to the surface or they may be hybridized to probes in the feature. A feature may be used both for amplification of a specific target and for analysis of the target. Analysis may be by sequencing by extension or ligation, for example. The amplification may be with a primer that hybridizes to a plurality of targets, for example, it may adaptor-mediated.

In one aspect, a method for nucleic acid analysis is disclosed. The method includes the steps of (a) fragmenting a nucleic acid sample to obtain fragments; (b) ligating adapters to the fragments to obtain adapter-ligated fragments; (c) hybridizing the adapter-ligated fragments to an array of target-specific probes, wherein target-specific probes are arranged on the array in features so that probes that are specific for the same target are present in the same feature; (d) extending the target-specific probes that are hybridized to adapter-ligated fragments, thereby obtaining extended target-specific probes that comprise copies of adapter-ligated fragments and terminate with an adapter sequence; (e) hybridizing a primer to the adapter sequence and extend the primer to make a copy of the extended target-specific probes; (f) repeating step (e) at least once, wherein a copy of the extended target-specific probe is displaced; and (g) analyzing the extended target-specific probes displaced in (f).

In a related aspect step (g) includes hybridizing the extended target-specific probes displaced in step (f) to an array of probes to obtain hybridized probes and extending the hybridized probes by a labeled nucleotide and determining the identity of the labeled nucleotide, thereby sequencing the target.

In another aspect, a method for amplifying selected targets is disclosed. The method includes the steps of (a) fragmenting a nucleic acid sample comprising said target to obtain fragments and ligating adapters to the fragments to obtain adapter-ligated fragments; (b) hybridizing the adapter-ligated fragments to a support bound probe to the target, wherein said probe is attached to the support at its 5' end and has a free 3' end; (c) hybridizing a splint to the adapter sequences of the target such that the 5' and 3' ends of the target are adjacent and ligating the ends to form circularized target; and (d) extending the support bound probe using the circularized target as template to obtain an extended probe comprising a plurality of copies of the target. The extending step may be by rolling circle amplification using a strand displacing polymerase. The extended probe can be detected as a surrogate for the target.

Any of the disclosed methods of amplification can be used to analyze a plurality of targets by following the amplification with the following detection steps: (a) hybridizing a primer to the amplified targets; step (b) extending the hybridized primer by a single base using a template dependent polymerase, wherein the base that is added is complementary to the base in the target that is immediately adjacent to the 3' end of the primer; step (c) determining the identity of the base added in (b); and step (d) repeating (b) and (c) to determine the sequence of a region of the target.

Differentially labeled based that are blocked from extension by a blocking group can be used for labeling. After detection of the label the blocking group and the label can be removed and the extension repeated to determine the sequence.

In another aspect, targets may be amplified by (a) hybridizing each target to a first complementary support bound probe in an array comprising a plurality of support bound probes, where probes of the same sequence are present in the same feature and wherein different targets hybridize to different first probes in different; (b) extending the first probes using the hybridized targets as template to obtain extended first probes; (c) optionally removing the target; (d) attaching an adapter to the 3' end of the extended first probes, wherein said adapter comprises a top strand that attached to the extended first probes, a bottom strand that is hybridized to the first strand and a nicking site in the second strand; (e) extending the 3' end of the bottom strand using the extended first probes as template to obtain an extended bottom strand; (f) nicking the extended bottom strand at the nicking site to generate a free 3' end and extending from the free 3' end to make another extended bottom strand, thereby displacing the portion of the extended bottom strand that is 3' of the nick, wherein the displaced portion is a copy of a portion of the target and allowing said portion of the target to hybridize to second probes in the feature and extending the second probes to obtain second extended probes; and (g) repeating the nicking and extension steps to make amplified copies of the targets.

In another aspect targets may be amplified by (a) hybridizing each target to a first complementary support bound probe in an array comprising a plurality of support bound probes, where probes of the same sequence are present in the same feature and wherein different targets hybridize to different first probes in different; (b) extending the first probes using the hybridized targets as template to obtain extended first probes;

(c) removing the target; (d) attaching an adapter to the 3' end of the extended first probes, wherein said adapter comprises a top strand that is attached to the extended first probes, and a bottom strand that is hybridized to the first strand, wherein said bottom strand comprises a chimeric primer that has a 5' RNA portion and a 3' DNA portion (or alternatively RNA alone); (e) extending the 3' end of the bottom strand using the extended first probes as template to obtain an extended bottom strand; (f) treating the products of (e) with RNase H so that the 3' RNA portion of the chimeric primer is removed; (g) hybridizing another copy of the chimeric primer to the extended first probes and extending said another copy of the chimeric primer, thereby displacing an extended bottom strand and generating an additional extended bottom strand, wherein displaced extended bottom strands hybridize to probes in the feature; and (h) repeating (f) and (g) to obtain amplified copies of the targets hybridized to probes in the feature.

In another aspect targets are amplified by (a) hybridizing each target to a first complementary support bound probe in an array comprising a plurality of support bound probes, where probes of the same sequence are present in the same feature and wherein different targets hybridize to different first probes in different features; (b) extending the first probes using the hybridized targets as template to obtain extended first probes; (c) removing the target; (d) attaching an adapter to the 3' end of the extended first probes, wherein said adapter comprises a top strand that is attached to the extended first probes, and a bottom strand that is hybridized to the first strand, wherein said adapter comprises a T7 RNA polymerase promoter; (e) transcribing multiple RNA copies of the extended first probe using T7 RNA polymerase; (f) allowing the copies of the extended first probe to hybridize to probes of the array in the same feature; and (g) analyzing the copies to determine the sequence of the targets.

In another aspect targets may be amplified as follows: (a) hybridizing each target to a first complementary support bound probe in an array comprising a plurality of support bound probes, where probes of the same sequence are present in the same feature and wherein different targets hybridize to different first probes in different; (b) extending the first probes using the hybridized targets as template to obtain extended first probes; (c) optionally removing the target; (d) ligating a hairpin oligonucleotide to the 3' end of the extended first probes, wherein said hairpin oligonucleotide comprises a double stranded region, a loop region and a 3' end, and extending the 3' end of the hairpin oligonucleotide using the extended first probes as template to obtain a double stranded support bound extension product corresponding to a double stranded copy of the target; (e) allowing the 3' end of the extension product generated in (d) to hybridize to second probes in the same features and extending the second probes to obtain second extended probes; (f) allowing the 3' end of the second extended probes to hybridize to another copy of the second probes and extending; and (g) repeating step (f) at least once to obtain a plurality of amplified targets.

In some aspects the hairpin oligonucleotide includes a cleavage site that may be one or more uracil bases. In another aspect, the double stranded region of the hairpin terminates with a base pair between the 5' terminal nucleotide and the 3' terminal nucleotide.

In another aspect, the target is circularized and hybridized to a probe on a solid support and extended. In preferred aspects the circularization takes place after the target has hybridized to the probe on the array. The probe is extended using rolling circle amplification (RCA) to generate a contiguous nucleic acid containing multiple copies of the target arranged end to end and preferably with a universal priming sequence within or adjacent to each copy of the target. The universal priming site is then used for sequencing or identification of the target.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 1A shows a method for amplification and analysis using a hairpin oligo.

FIG. 1B shows a method for amplification and analysis using strand displacement synthesis.

FIG. 1C shows a method for amplification using an RNA:DNA chimeric oligo to prime synthesis.

FIG. 1D shows a method for amplification and analysis using a T7 promoter and in vitro transcription to generate amplified products for analysis.

FIG. 2 shows a method for amplification and analysis using adapter ligated fragments.

FIG. 3 shows a schematic of solid phase, allele specific amplification with strand displacement.

FIG. 6A shows target specific probe extension at different features of an array.

FIG. 6B shows amplification of the extended probe to generate multiple copies of the target and hybridization of the target copies to other probes within the feature specific for that target.

FIG. 7A shows the method schematically. FIG. 7B shows an experiment schematically and scans of the resulting arrays.

FIG. 20 shows a method for sequencing using terminal ligation probes.

Figure 1E:
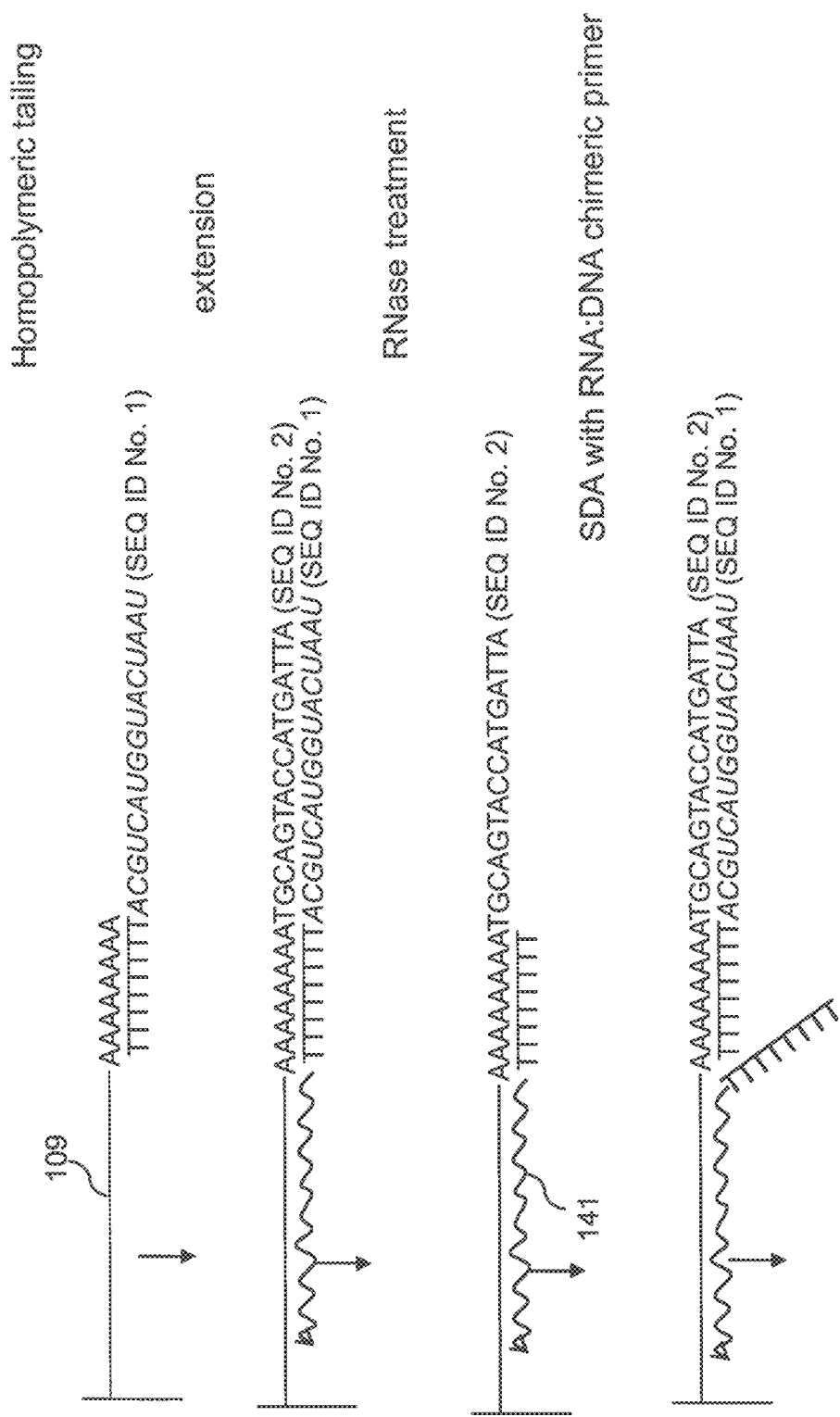
FIG. 1E shows a method for amplification of targets using homopolymeric tailing and an RNA:DNA chimeric primer.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, "*Oligonucleotide Synthesis: A Practical Approach*" 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes. Additional methods for nucleic acid array synthesis are disclosed in US 20070161778, which describes the use of acid scavengers in array synthesis and U.S. Pat. No. 6,271,957 which describes methods for array synthesis where areas are activated by spatial light modulation and without the use of a photomask.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GENECHIP. Example arrays are shown on the website at affymetrix.com. In preferred aspects the arrays are arrays of oligonucleotide probes of from length 15 to 100, more preferably from 20 to 50 and often from 20 to 30 bases in length. In preferred aspects the probes are arranged in features so that probes of the same sequence are present in the same feature. Many thousands, tens of thousands, hundreds of thousands or millions of different copies of a given probe sequence may be present in a feature. Depending on the method of synthesis of the probes on the array features will often contain non-full length probes that may be a portion of the desired sequence.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Patent Pub. No. 20070065816 and U.S. Pat. Nos. 5,856,092, 6,300,063, 5,858,659, 6,284,460, 6,361, 947, 6,368,799, 6,872,529 and 6,333,179. Other uses are embodied in U.S. Pat. Nos. 5,871,928, 5,902,723, 6,045, 996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, NY, 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. Ser. No. 09/513, 300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603 each of which is incorporated herein by reference). Other amplification methods that may be used are described in, U.S. Pat. Nos. 5,242,794, 5,494,810, 4,988,617 and 6,582,938, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592, 6,632,611, 6,872, 529, 6,958,225 and 7,202,039. Enzymatic methods for genotyping are also disclosed in U.S. Patent Pub. No. 20080131894.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, 6,225,625, and 7,689,022 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; 6,225,625, and 7,689,022 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology,* (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Patent Pub. Nos. 20020183936, 20070087368, 20040049354 and 20030120432, each incorporated herein by reference.

The present invention is also related to US Patent Pub. No. 20080199916 A1, which is incorporated herein by reference in its entirety. Methods for multiplex amplification of targets using circularization probes are disclosed therein. In some aspects flap endonucleases are used to remove 5' or 3' flaps or overhanging single stranded regions.

b) Definitions

"Adaptor sequences" or "adaptors" are generally oligonucleotides of at least 5, 10, or 15 bases and preferably no more than 50 or 60 bases in length; however, they may be even longer, up to 100 or 200 bases. Adaptor sequences may be synthesized using any methods known to those of skill in the art. For the purposes of this invention they may, as options, comprise primer binding sites, recognition sites for endonucleases, common sequences and promoters. The adaptor may be entirely or substantially double stranded or entirely single stranded. A double stranded adaptor may comprise two oligonucleotides that are at least partially complementary. The adaptor may be phosphorylated or unphosphorylated on one or both strands.

Adaptors may be more efficiently ligated to fragments if they comprise a substantially double stranded region and a short single stranded region which is complementary to the single stranded region created by digestion with a restriction enzyme. For example, when DNA is digested with the restriction enzyme EcoRI the resulting double stranded fragments are flanked at either end by the single stranded overhang 5'-AATT-3', an adaptor that carries a single stranded overhang 5'-AATT-3' will hybridize to the fragment through complementarity between the overhanging regions. This "sticky end" hybridization of the adaptor to the fragment may facilitate ligation of the adaptor to the fragment but blunt ended ligation is also possible. Blunt ends can be converted to sticky ends using the exonuclease activity of the Klenow fragment. For example when DNA is digested with PvuII the blunt ends can be converted to a two base pair overhang by incubating the fragments with Klenow in the presence of dTTP and dCTP. Overhangs may also be converted to blunt ends by filling in an overhang or removing an overhang.

Methods of ligation will be known to those of skill in the art and are described, for example in Sambrook et al. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'→5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of adaptors to one or both ends to facilitate ligation by generating ends that are compatible with ligation.

Adaptors may also incorporate modified nucleotides that modify the properties of the adaptor sequence. For example, phosphorothioate groups may be incorporated in one of the adaptor strands. A phosphorothioate group is a modified phosphate group with one of the oxygen atoms replaced by a sulfur atom. In a phosphorothioated oligo (often called, an "S-Oligo"), some or all of the internucleotide phosphate groups are replaced by phosphorothioate groups. The modified backbone of an S-Oligo is resistant to the action of most exonucleases and endonucleases. Phosphorothioates may be incorporated between all residues of an adaptor strand, or at specified locations within a sequence. A useful option is to sulfurize only the last few residues at each end of the oligo. This results in an oligo that is resistant to exonucleases, but has a natural DNA center.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa *Nucleic Acids Res.* 12:203 (1984), incorporated herein by reference.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25° C.-30° C. are suitable for allele-specific probe hybridizations or conditions of 100 mM MES, 1 M Na+, 20 mM EDTA, 0.01% Tween-20 and a temperature of 30° C.-50° C., preferably at about 45° C.-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GENECHIP Mapping Assay Manual, 2004, available at Affymetrix.com.

The term "hybridization probes" as used herein are oligonucleotides capable of binding in a base-specific manner to a complementary strand of nucleic acid. Such probes include peptide nucleic acids, as described in Nielsen et al., *Science* 254, 1497-1500 (1991), LNAs, as described in Koshkin et al. *Tetrahedron* 54:3607-3630, 1998, and U.S. Pat. No. 6,268,490 and other nucleic acid analogs and nucleic acid mimetics.

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

"Nicking endonucleases" are restriction enzymes that hydrolyze only one strand of the DNA duplex, to produce DNA molecules that are "nicked", rather than cleaved. The resulting nicks (3'-hydroxyl, 5'-phosphate) can serve as initiation points for further enzymatic reactions such as replacement DNA synthesis, strand-displacement amplification (Walker, G. T. et al. (1992) *Proc. Natl. Acad. Sci. USA* 89, 392-396.), exonucleolytic degradation or the creation of small gaps (Wang, H. and Hays, J. B. (2000) *Mol. Biotechnol.* 15, 97-104). These enzymes may occur naturally or they may be engineered or altered to nick. N.BstNB I occurs naturally and nicks because it is unable to form dimers. N.Alw I is a derivative of the restriction enzyme Alw I, that has been engineered to behave in the same way. These enzymes nick adjacent to their recognition sequences. N.BbvC IA and N.BbvC D3 are derived from the heterodimeric restriction enzyme BbvC I, each has only one catalytic site so they nick within the recognition sequence but on opposite strands. In some embodiments newly engineered or discovered nicking enzymes are used. It is likely that the methods used to engineer existing nicking enzymes will be broadly applicable and many existing restriction enzymes may be engineered to produce corresponding nicking enzymes. Nicking sites may also be engineered by including hemiphosphorothioate sites as described in Walker, G. T. et al. (1992) *Proc. Natl. Acad. Sci. USA* 89, 392-396.

DNA Polymerase I Large (Klenow) Fragment consists of a single polypeptide chain (68 kDa) that lacks the 5'->3' exonuclease activity of intact *E. coli* DNA polymerase I, but retains its 5'->3' polymerase, 3'->5' exonuclease and strand displacement activities. The Klenow fragment has been used for strand displacement amplification (SDA). See, e.g., U.S. Pat. Nos. 6,379,888; 6,054,279; 5,919,630; 5,856,145; 5,846,726; 5,800,989; 5,766,852; 5,744,311; 5,736,365; 5,712,124; 5,702,926; 5,648,211; 5,641,633; 5,624,825; 5,593,867; 5,561,044; 5,550,025; 5,547,861; 5,536,649; 5,470,723; 5,455,166; 5,422,252; 5,270,184, all incorporated herein by reference.

The term "nucleic acid library" as used herein refers to an intentionally created collection of nucleic acids which can be prepared either synthetically or biosynthetically and screened for biological activity in a variety of different formats (for example, libraries of soluble molecules; and libraries of oligos tethered to beads, chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

"Photoresist" refers to a light sensitive liquid or a film, which when selectively exposed to light, masks off areas of the design that can then be etched away. The use of photoresist technology allows for selective etching of areas. Photoresist technology may be used to synthesize oligonucleotide arrays, see, for example, U.S. Pat. Nos. 6,083,697 and 5,658,734 which are both incorporated herein by reference in their entireties.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 5%, 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

A "predefined region" is a localized area on a substrate which is, was, or is intended to be used for formation of a selected polymer and is otherwise referred to herein in the alternative as "reaction" region, a "selected" region, simply a "region" or a "feature". The predefined region may have any convenient shape, e.g., circular, rectangular, elliptical, wedge-shaped, etc. In accordance with the present invention, the arrays of the present invention have features on the order of 10-100 µm, i.e. $10 \times 10$ µm$^2$ to $100 \times 100$ µm$^2$ for approximately square features. More preferably the features will be on the order of 1-10 µm. In preferred aspects the present invention may be used in combination with arrays having features having sub-micron dimensions. Such features are preferably on the order of 100-1000 nm. Within these regions, the polymer synthesized therein is preferably synthesized in a substantially pure form. However, in other embodiments of the invention, predefined regions may substantially overlap. In such embodiments, hybridization results may be resolved by software, for example. Smaller feature sizes allow larger numbers of features on arrays of a given size. For example, a about 1.3 million features can be included using $11 \times 11$ µm features on a $1.28 \times 1.28$ cm array and the same array can have more then 6 million features with $5 \times 5$ features or more than 2 million with $8 \times 8$ µm features. Using a $5 \times 5$ inch wafer 49 such arrays can be synthesized on a wafer, for about 63.7 million features on a wafer. The wafer can be diced to form arrays of a variety of sizes, for example, $20 \times 20$ dicing of the wafer gives 400 arrays and $30 \times 30$ gives 900 arrays. One of skill in the art will recognize that larger wafers may also be used and smaller feature size allows larger numbers of features in a given area. Features sizes that may be used include $5 \times 5$ µm or 25 µm$^2$ and $1 \times 1$ (1 µm$^2$) and smaller, for example, $0.5 \times 0.5$ µm (0.25 µm$^2$) features. The methods contemplate arrays of 1 to 2, 2-5, 5-10, 10-20, or 20-100 million different features, each feature containing many copies of a given probe sequence.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptor is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

Next-generation sequencing methods are disclosed, for example, in Ansorge, W J, *N. Biotechnol.*, 2009, 25(4):195-203, Mardis, *Annu Rev. Genomics Hum Genet.* 2008, 9:387-402 and Schuster S C, *Nat Methods,* 2008, 5(1):16-18. The methods are non-Sanger-based methods that enable sequencing of nucleic acid at unprecedented speed. Additional description may be found, for example, in Ozsolak, F., et al. *Nature,* 2009 Sep. 23, epub, Bowers et al. *Nat. Methods,* 2009, 6(8):593-595, and Wheeler, D A, et al., *Nature,* 2008, 452:872-876. Other methods are shown in Pihlak, A. et al. *Nat. Biotechnology* 26, 676-684 (2008).

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term target is used herein, no difference in meaning is intended. A "Probe Target Pair" is formed when two macromolecules have combined through molecular recognition to form a complex.

The term "wafer" as used herein refers to a substrate having surface to which a plurality of arrays are bound. In a preferred embodiment, the arrays are synthesized on the surface of the substrate to create multiple arrays that are physically separate. In one preferred embodiment of a wafer, the arrays are physically separated by a distance of at least about 0.1, 0.25, 0.5, 1 or 1.5 millimeters. The arrays that are on the wafer may be identical, each one may be different, or there may be some combination thereof. Particularly preferred wafers are about 8"×8" and are made using the photolithographic process.

In one aspect, rolling circle amplification (RCA) or rolling circle replication (RCR) is used to create concatemers of the invention. The RCA/RCR process has been shown to generate multiple continuous copies of the M13 genome. (Blanco, et al., (1989) *J Biol Chem* 264:8935-8940). In such a method, a nucleic acid is replicated by linear concatemerization. Guidance for selecting conditions and reagents for RCA reactions is available in many references available to those of ordinary skill, including U.S. Pat. Nos. 5,426,180; 5,854,033; 6,143,495; and 5,871,921, each of which is hereby incorporated by reference in its entirety for all purposes and in particular for all teachings related to generating concatemers using RCA or other methods. RCA of DNA immobilized on solid surfaces and its application variation detection has been shown, for example, in Hatch A, et al. *Genet Anal.* 1999, 15(2):35-40. Amplification of closed circular DNA is described, for example in Chen and Ruffner, *Nucleic Acids Research*, Vol 26, Issue 4 1126-1127. Amplification by rolling circle amplification on arrays has been shown, for example, in Nallur et al. *Nucleic Acids Res.* 2001 Dec. 1; 29(23): e118. Circle based amplification methods are also disclosed, for example, in Baner et al. (1998) NAR 26:5073, Lizardi et al. (1998) Nat. Genet. 19:225 and Fire and Xu, (1995) PNAS 92:4641-5. Integration of DNA ligation and rolling circle amplification for detection of single nucleotide polymorphisms has been shown, for example, in Pickering, J. et al., *Nucleic Acids Research*, 2002, Vol. 30, No. 12 e60. Methods related to DNA condensation are disclosed in, for example, Y Fang and JH Hoh. Nucleic Acids Research, 26 (2): 588-593 and in Bloomfield, Cur. Op. Struct. Biol. 1996, 6:334-341. Additional methods related to circularization of targets followed by amplification are disclosed in US Pat. Pub. 20080131899.

The term "isothermal amplification" refers to an amplification reaction that is conducted at a substantially constant temperature. The isothermal portion of the reaction may be proceeded by or followed by one or more steps at a variable temperature, for example, a first denaturation step and a final heat inactivation step or cooling step. It will be understood that this definition by no means excludes certain, preferably small, variations in temperature but is rather used to differentiate the isothermal amplification techniques from other amplification techniques known in the art that basically rely on "cycling temperatures" in order to generate the amplified products. Isothermal amplification, varies from, for example PCR, in that PCR amplification relies on cycles of denaturation by heating followed by primer hybridization and polymerization at a lower temperature.

The term "Strand Displacement Amplification" (SDA) is an isothermal in vitro method for amplification of nucleic acid. In general, SDA methods initiate synthesis of a copy of a nucleic acid at a free 3' OH that may be provided, for example, by a primer that is hybridized to the template. The DNA polymerase extends from the free 3' OH and in so doing, displaces the strand that is hybridized to the template leaving a newly synthesized strand in its place. Subsequent rounds of amplification can be primed by a new primer that hybridizes 5' of the original primer or by introduction of a nick in the original primer. Repeated nicking and extension with continuous displacement of new DNA strands results in exponential amplification of the original template. Methods of SDA have been previously disclosed, including use of nicking by a restriction enzyme where the template strand is resistant to cleavage as a result of hemimethylation. Another method of performing SDA involves the use of "nicking" restriction enzymes that are modified to cleave only one strand at the enzymes recognition site. A number of nicking restriction enzymes are commercially available from New England Biolabs and other commercial vendors.

Polymerases useful for SDA generally will initiate 5' to 3' polymerization at a nick site, will have strand displacing activity, and preferably will lack substantial 5' to 3' exonuclease activity. Enzymes that may be used include, for example, the Klenow fragment of DNA polymerase I, Bst polymerase large fragment, Phi29, and others. DNA Polymerase I Large (Klenow) Fragment consists of a single polypeptide chain (68 kDa) that lacks the 5' to 3' exonuclease activity of intact *E. coli* DNA polymerase I. However, DNA Polymerase I Large (Klenow) Fragment retains its 5' to 3' polymerase, 3' to 5' exonuclease and strand displacement activities. The Klenow fragment has been used for SDA. For methods of using Klenow for SDA see, for example, U.S. Pat. Nos. 6,379,888; 6,054,279; 5,919,630; 5,856,145; 5,846,726; 5,800,989; 5,766,852; 5,744,311; 5,736,365; 5,712,124; 5,702,926; 5,648,211; 5,641,633; 5,624,825; 5,593,867; 5,561,044; 5,550,025; 5,547,861; 5,536,649; 5,470,723; 5,455,166; 5,422,252; 5,270,184, the disclosures of which are incorporated herein by reference. Examples of other enzymes that may be used include: exo minus Vent (NEB), exo minus Deep Vent (NEB), Bst (BioRad), exo minus Pfu (Stratagene), Pfx (Invitrogen), 9° $N_m$™ (NEB), and other thermostable polymerases.

Phi29 is a DNA polymerase from *Bacillus subtilis* that is capable of extending a primer over a very long range, for example, more than 10 Kb and up to about 70 Kb. This enzyme catalyzes a highly processive DNA synthesis coupled to strand displacement and possesses an inherent 3' to 5' exonuclease activity, acting on both double and single stranded DNA. Variants of phi29 enzymes may be used, for example, an exonuclease minus variant may be used. Phi29 DNA Polymerase optimal temperature range is between about 30° C. to 37° C., but the enzyme will also function at higher temperatures and may be inactivated by incubation at about 65° C. for about 10 minutes. Phi29 DNA polymerase and Tma Endonuclease V (available from Fermentas Life Sciences) are active under compatible buffer conditions. Phi29 is 90% active in NEBuffer 4 (20 mM Tris-acetate, 50 mM potassium acetate, 10 mM magnesium acetate and 1 mM DTT, pH 7.9 at 25° C.) and is also active in NEBuffer 1 (10 mM Bis-Tris-Propane-HCl, 10 mM magnesium chloride and 1 mM DTT, pH 7.0 at 25° C.), NEBuffer 2 (50 mM sodium chloride, 10 mM Tris-HCl, 10 mM magnesium chloride and 1 mM DTT, pH 7.9 at 25° C.), NEBuffer 3 (100 mM NaCl, 50 mM Tris HCl, 10 mM magnesium chloride and 1 mM DTT, pH 7.9 at 25° C.). For additional information on phi29, see U.S. Pat. Nos. 5,001,050, 5,198,543 and 5,576,204 and Esteban, J. A., Salas, M. and Blanco, L. (1993) *J. Biol. Chem.* 268 2719-2726, Garmendia, C., Bemad, A., Esteban, J. A., Blanco, L. and Salas, M. (1992) *J. Biol. Chem.* 26%, 2594-2599 and Blanco, L., Bemad, A., Lazaro, I. M., Martin, G., Garmendia, C. and Salas, M. (1989) *J. Biol. Chem.* 264, 8935-8940.

Bst DNA polymerase originates from *Bacillus stearothermophilus* and has a 5' to 3' polymerase activity, but lacks a 5' to 3' exonuclease activity. This polymerase is known to have strand displacing activity. The enzyme is available from, for example, New England Biolabs. Bst is active at high temperatures and the reaction may be incubated optimally at about 65° C. but also retains 30%-45% of its activity at 50° C. Its active range is between 37° C.-80° C. The enzyme tolerates reaction conditions of 70° C. and below and can be heat inactivated by incubation at 80° C. for 10 minutes. Bst DNA polymerase is active in the NEBuffer 4 (20 mM Tris-acetate, 50 mM potassium acetate, 10 mM magnesium acetate and 1 mM DTT, pH 7.9 at 25° C.) as well as NEBuffer 1 (10 mM Bis-Tris-Propane-HCl, 10 mM magnesium chloride and 1 mM DTT, pH 7.0 at 25° C.), NEBuffer 2 (50 mM sodium chloride, 10 mM Tris-HCl, 10 mM magnesium chloride and 1 mM DTT, pH 7.9 at 25° C.), and NEBuffer 3 (100 mM NaCl, 50 mM Tris HCl, 10 mM magnesium chloride and 1 mM DTT, pH 7.9 at 25° C.). Bst DNA polymerase could be used in conjunction with *E. coli* Endonuclease V (available from New England Biolabs). For additional information see Mead, D. A. et al. (1991) *BioTechniques*, p.p. 76-87, McClary, J. et al. (1991) *J. DNA Sequencing and Mapping*, p.p. 173-180 and Hugh, G. and Griffin, M. (1994) *PCR Technology*, p.p. 228-229.

The term "endonuclease" refers to an enzyme that cleaves a nucleic acid (DNA or RNA) at internal sites in a nucleotide base sequence. Cleavage may be at a specific recognition sequence, at sites of modification or randomly. Specifically, their biochemical activity is the hydrolysis of the phosphodiester backbone at sites in a DNA sequence. Examples of endonucleases include Endonuclease V (Endo V) also called deoxyinosine 3' endonuclease, which recognizes DNA containing deoxyinosines (paired or not). Endonuclease V cleaves the second and third phosphodiester bonds 3' to the mismatch of deoxyinosine with a 95% efficiency for the second bond and a 5% efficiency for the third bond, leaving a nick with 3' hydroxyl and 5' phosphate. Endo V, to a lesser, degree, also recognizes DNA containing abasic sites and also DNA containing urea residues, base mismatches, insertion/deletion mismatches, hairpin or unpaired loops, flaps and pseudo-Y structures. See also, Yao et al., *J. Biol. Chem.*, 271(48): 30672 (1996), Yao et al., *J. Biol. Chem.*, 270(48): 28609 (1995), Yao et al., *J. Biol. Chem.*, 269(50): 31390 (1994), and He et al., *Mutat. Res.*, 459(2):109 (2000). Endo V from *E. coli* is active at temperatures between about 30 and 50° C. and preferably is incubated at a temperature between about 30° C. to 37° C. Endo V is active in NEBuffer 4 (20 mM Tris-acetate, 50 mM potassium acetate, 10 mM magnesium acetate and 1 mM DTT, pH 7.9 at 25° C.), but is also active in other buffer conditions, for example, 20 mM HEPES-NaOH (pH 7.4), 100 mM KCl, 2 mM $MnCl_2$ and 0.1 mg/ml BSA. Endo V makes a strand specific nick about 2-3 nucleotides downstream of the 3' side of inosine base, without removing the inosine base. Endonucleases, including Endo V, may be obtained from manufacturers such as New England Biolabs (NEB) or Fermentas Life Sciences. The enzyme Uracil-DNA Glycosylase (UDG or UNG) catalyzes the hydrolysis of the N-glycosylic bond between the uracil and sugar, leaving an apyrimidinic site in uracil-containing single or double-stranded DNA. This activity has been used, for example, for site directed mutation (Kunkel, PNAS 82:488-492 (1985) and for elimination of PCR carry-over contamination (Longo, et al., *Gene* 93:125-128 (1990). Uracil mediated cleavage has also been used for cleaving single stranded circularized probes (Hardenbol et al., Genome Res. 15:269-75 (2005).

The RecA protein is a protein found in *E. coli* that in the presence of ATP, promotes the strand exchange of single-strand DNA fragments with homologous duplex DNA. RecA is also an ATPase, an enzyme capable of hydrolyzing ATP, when bound to DNA. RecA uses ATP to carry out strand exchange over long sequences and impose direction to the exchange, to bypass short sequence heterogeneities, and to stall replication so DNA lesions can be mended. The reaction has three distinct steps: (i) RecA polymerizes on the single-strand DNA to form a nucleoprotein filament, (ii) the nucleoprotein filament binds the duplex DNA and searches for a homologous region in a process that requires ATP but not hydrolysis, because ATPγS, a noncleavable analogue, can substitute, (iii) RecA catalyzes local denaturation of the duplex and strand exchange with the single-stranded DNA, see also Radding, C. M. (1991) *J. Biol. Chem.*, 266: 5355-5358. Recombinant *E. coli* RecA is commercially available from, for example, New England Biolabs. The use of a nonhydrolyzable analogue such as ATPγS favors the formation of stable triple stranded complexes. For reaction conditions useful for promoting oligonucleotide binding to a duplex DNA, see Rigas et al. *Proc. Natl. Acad. Sci. USA* 83:9591-9595 (1986) and Honigberg et al. *Proc. Natl. Acad. Sci. USA* 83:9586-9590 (1986). RecA is active under a variety of reaction conditions and can be heat inactivated at 65° C. for 20 minutes.

DNA polymerases harboring strand displacement activities are widely used for isothermal amplification reactions. DNA polymerases from the phage Phi29, from bacteria BST XI, and the Klenow fragment of DNA polymerase I from *E. coli* are examples of enzymes that exhibit strand displacement activities. These polymerases have been used in reactions containing specific oligonucleotide primers or short random primers to amplify DNA. Due to the highly processive nature of some of these polymerase enzymes, they can be used to amplify template DNAs of long lengths. Templates can also be circular DNA molecules, where successive rounds of amplification result in a "rolling circle" mechanism.

DNA arrays can be manufactured with DNA probes immobilized on their 5'ends, allowing for the free 3'hydroxyl ends to participate in polymerase reactions in solution. Essentially, these arrayed probes can serve as oligonucleotide primers for various enzymatic reactions, including the action of DNA polymerases. For example, DNA targets hybridized to these probes can serve as templates in a DNA polymerase reaction. Methods of utilizing 3'hydroxyl probe arrays to capture, circularize and amplify DNA fragments are disclosed herein. The amplified DNA fragments may serve as a clonal representation of hybridized DNA molecules that may be used as templates for subsequent reactions such as detection of specific sequences or DNA sequencing.

In preferred aspects, target DNA is hybridized as a linear fragment or as prepared circular DNAs. When linear fragments are hybridized, the arrayed probe sequences provide for hybridization in an inverse fashion, creating the opportunity to circularize the hybridized linear DNA through the action of DNA ligase. If desired, an additional universal sequence can be introduced on the probe for incorporation into the formed circular DNA. The sequences on the array probes define the target DNA that will hybridize to the array. One method of creating perfectly flushed ends with the array probes is to produce target DNA of known breakpoints, such as through the use of restriction enzymes. Other methods may also rely on the action of exonucleases and/or polymerases to create suitable ends for circle formation. Once DNA targets have been captured onto the arrays and turned into circular molecules, a DNA polymerase with a strong strand displacement activity is used to extend the array probes. During the polymerization reaction, the circular template is continuously displaced to lead to the generation of long strands of amplified DNAs. The length of these long amplified strands can exceed tens to hundreds of kilobases. Visually, they appear as hair-like strands that can extend over hundreds of microns. These long DNAs can be condensed and 'coiled' into tertiary structures on the array surface using appropriate conditions (see FIGS. 10 and 12). Each amplified DNA strand represents a clonally duplicated copy of the original hybridized template. The number of times a template is amplified is directly correlated with the number of cycles of rolling circle amplification. For example, a 50 kb amplified strand from a 100 base long hybridized fragment represents a 500-fold amplification rate.

Figure 12:
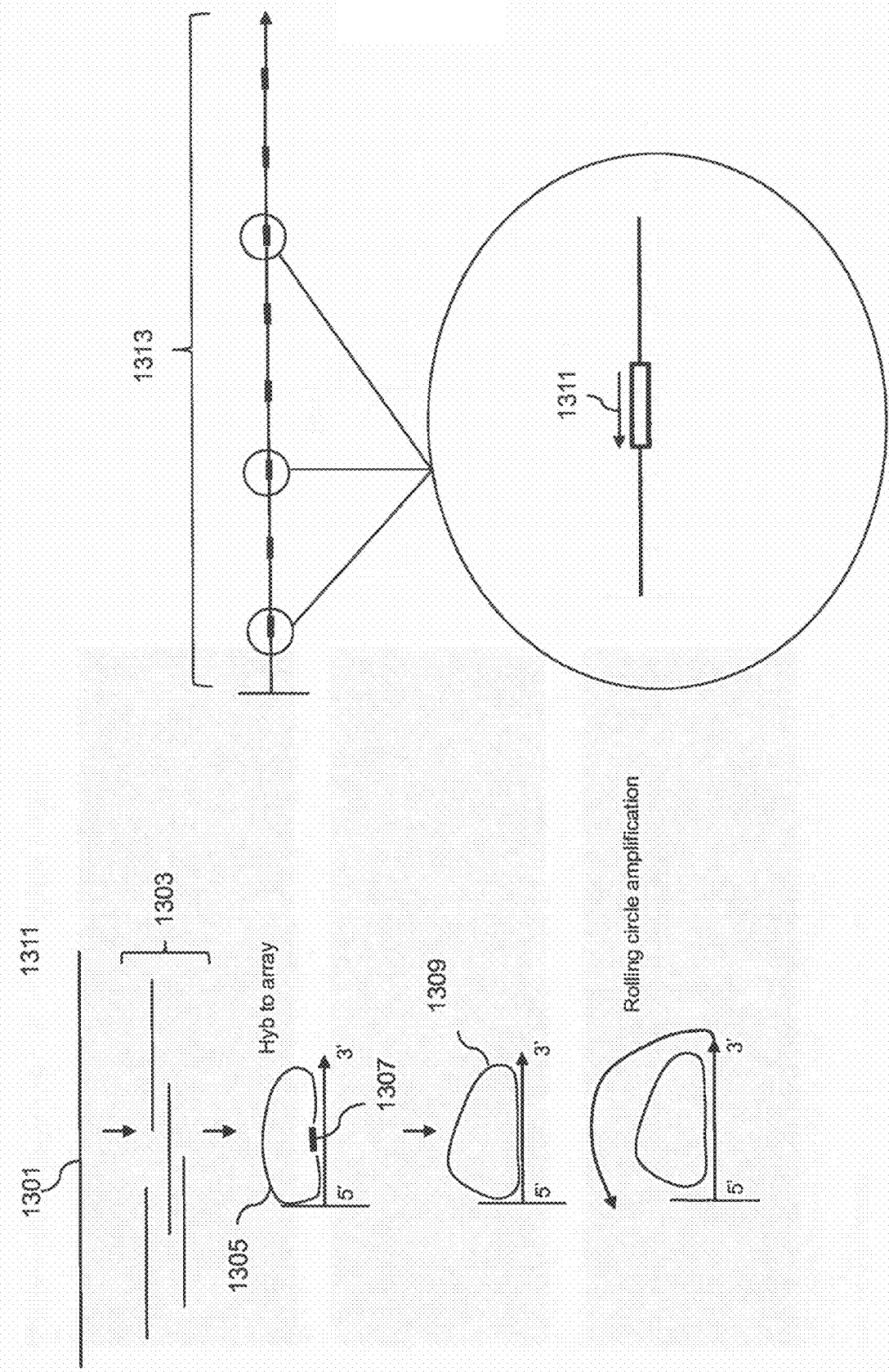
FIG. 12 shows a schematic of a method for forming amplicons of target sequences that include common priming sequences.

Downstream applications for the captured, and amplified DNAs are numerous. For example, the incorporation of a universal sequence in each circle copy provides a priming site for DNA sequencing. As shown in FIG. 12 this method incorporates a universal sequence into the amplified DNA. The probe on the array has a 5' target specific region and a 3' target specific region with a universal priming site in between. The fragment hybridizes to the probe on the array as an inversion. A sequence complementary to the universal priming site hybridizes to the universal priming site and the gaps are closed using, for example, T4 ligase, to form a closed circle template.

Figure 13:
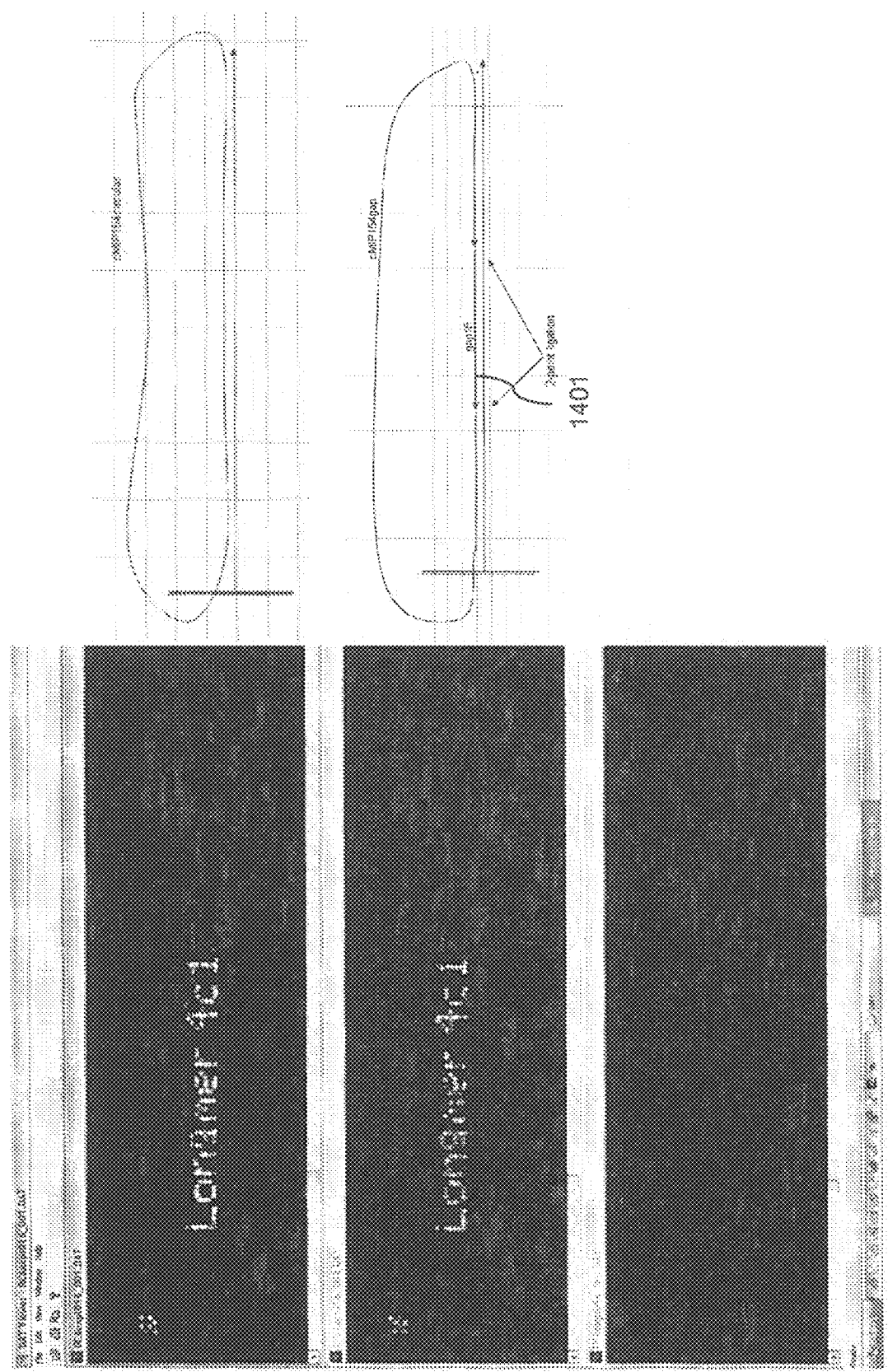
FIG. 13 shows array images of RCA on array using a closed circle target or a ligated closed circle target using the 2 point ligation method.

Rolling circle amplification (RCA) with phi29 DNA polymerase is demonstrated on Affymetrix GENECHIP arrays with 3'OH probes in FIG. 13. RCA templates can be hybridized as linear DNA molecules with inverted ends that can be subsequently ligated with T4 DNA ligase on the array to form closed circular templates. RCA products are long DNA strands that stretch beyond a single cell feature on the array, complicating intensity extraction. However, in the presence of certain cationic solutions, the long RCA DNA products condense and pack into singular feature cells, enabling accurate intensity determination.

In some embodiments a 2-point ligation on the array may be used. Alternatively, a single point ligation may be used in combination with an extension reaction. The bound DNA fragment may be extended using a polymerase to incorporate the complement of the universal priming sequence. The extended end can then be ligated to the end of the DNA target. Experiments performed with oligo targets demonstrate the function of the method. In preferred aspects arrays are designed with probes directed to selected genomic targets.

In some aspects a common restriction enzyme is used to define the target fragment locus. Although this approach is limited somewhat in its inability to target any fragment in the genome (fragments that are flanked by appropriate restriction sites are preferentially amplified), it has the advantage that complexity can be reduced using an adapter ligation amplification strategy if necessary. Also, the fragments are generated with end-point restriction enzyme cutting reactions that are easier to perform than DNAse I random fragmentation. The array bound probe in one embodiment has a 5' portion connected to the array, preferably through a linker, a center portion that includes the universal sequence and a 3' portion.

c) Locus-Specific Amplification and Sequencing Using Arrayed Probes

In a quest to enable the sequencing of entire genomes at low cost and high throughput, a number of methods of sequencing have been commercialized in recent years. Many of these technologies employ a massively parallel approach in order to accomplish sequencing at low cost. In these technologies, short fragments of random DNA are sequenced and then assembled together into a contiguous longer DNA sequence assembly. The disadvantage of these technologies is that each short fragment is essentially a random piece of DNA and in order to completely sequence a given region within the genome test sample, a large sampling redundancy is required. Secondly, there is no capability to avoid the repetitive, non-informative regions of the genome as sampling is random in nature.

To overcome this problem locus-specific probes can be used to target the regions of interest. One efficient method to generate highly multiplexed arrays of locus-specific probes is through in-situ synthesis, with one example being the photolithographic process used to produce Affymetrix GENECHIP arrays. Although the genome regions of interest can hybridize specifically to the arrayed probes and be detectable, the number of molecules (estimated to be in the hundreds or thousands at the maximum) is insufficient to conduct biochemical assays that deduce the sequence composition of hybridized molecules.

The method disclosed herein enables solid-phase locus specific amplification of limiting amounts of target molecules hybridized to arrayed probes. The hybridized target molecules are amplified while they remain specifically hybridized to the arrayed probes. Post solid-phase amplification, the amplified DNAs can be assayed by available sequencing methods. The methods may be used for locus-specific, low redundancy sequencing of genomic regions of interest or whole genomes.

In one embodiment the methods include generally the following steps: 1. Sample DNA is hybridized to a reverse probe (5' to 3' probes) array. 2. Specific DNA hybridized is used as template in an extension assay with DNA polymerase to extend the arrayed primer to the end of the hybridized target. 3. The hybridized target is removed via denaturation. 4. The end of the extended primer is attached to an oligonucleotide using DNA ligase or other available methods. The attached oligonucleotide may contain, for example, one or more nicking or cleaving restriction enzyme sites, universal sequences for priming, hairpin sequences, or a RNA polymerase promoter sequence such as T7, T3 or SP6. 5. By exploiting the attached oligonucleotide sequence, the extended probe can be made double-stranded using DNA polymerase. 6. The double stranded DNA is now used as template for strand-displacement, bridge-amplification, or in vitro transcription amplification reactions. 7. Amplified DNAs (or RNAs) hybridize to adjacent array probes as they get synthesized in the same physical space and the process could be repeated in cyclical fashion.

The amplification phase results in solid-phase amplification of locus-specific genomic sequences. The target hybridizes to the array at the feature that has the probe that is complementary to the target. This is shown schematically in FIG. 6. In FIG. 6A three single stranded target fragments 701a, b and c are shown. Each is a different sequence and the array shown on the right has three features 703a, b and c each having a different probe sequence. The probe sequence in feature 703a is complementary to a sequence in target 701a and likewise for the remaining two features. The boxes represent the probe sequence and the sequence in the target that is complementary to the probe in the array feature. The targets are hybridized to a complementary target probe in the feature corresponding to that target sequence to form probe: target complexes. The hybridized probe is extended to form an extended probe within the corresponding feature. The target fragments 701a, b and c are then removed from the extended probe, for example, by denaturation. They may hybridize to another probe in the feature and the probe extension may be repeated for one or more cycles. The extended probe may then be used as template to make copies of the extended probe 705a, b and c. Each time a copy is made it displaces the last copy made by SDA and the displaced copy is released and can hybridize to another probe in the feature resulting in multiple copies of the target hybridized in the feature. The amplified hybridized target can then be analyzed, for example by extending the probes using the hybridized target as template, for example in a sequencing by synthesis or sequencing by ligation assay.

The amplification of the target generates additional copies of the target sequence which can then hybridize to copies of the same target specific probe that are present at the original feature. Amplified sequences can be assayed by various biochemical methods such as single base extension or ligation assays using the same arrayed probes used for solid-phase amplification.

One embodiment is shown schematically in FIG. 1A. Probes 101 are attached to a support 103 at the 5' end leaving the 3' end available for extension. The target 105 hybridizes to the probe and the probe is extended to add region 107. The extended probe 109 includes both the probe 101 and the extended region 107 using a polymerase. The target is removed, for example, by denaturation, leaving the extension product attached to the array.

In the embodiment shown in FIG. 1A the next step is the ligation of a hairpin oligo 111 to the 3' end of the extended probe. The hairpin can fold back on itself to form a double stranded region with a 3' end hybridized to another region of the hairpin oligo. The 3' end of the hairpin oligo is extended with a polymerase using the extended probe as template, adding an extension region 113 to the end of the hairpin oligo and forming a double stranded extension product 115. The now double stranded extended probe may be subjected to a treatment that promotes strand switching so that the 3' end hybridizes to a second probe 117 on the array. Probes 101 and 117 may be different copies of the same probe sequence. The second probe may be extended to make a copy of 115 in a bridge amplification process as described in U.S. Pat. Nos. 6,060,288, 6,300,070 and 5,641,658. Multiple copies of 115 may be made by bridge amplification. In preferred embodiments the second probe is the same sequence as probe 101, but it may be a different sequence. The strand switching may be promoted by, for example, heat denaturation or helicase unwinding or by chemical means such as formamide or strong base. The second probe 117 may be extended using 115 as template. The resulting extension product is another copy of 115. Many copies of 115 may be made by repeating the migration of the 3' end of 115 to new probes in the region. The copies of 115 may be analyzed for sequence using sequencing by synthesis or ligation using probes 117 for extension. In some aspects probe 101 or 117 may contain a cleavage site, such as a uracil base or a restriction site.

The advantages of this approach include, for example, that the amplification is anchored and that the locus specific probe can be used for bridge amplification and sequencing. In preferred aspects high reaction temperatures are used for bridge amplification. Steps may be taken to minimize strand switching to neighboring probes.

In some aspects the hairpin oligo includes a cleavage site or a primer binding site. After amplification to make multiple copies of 115, the cleavage site in the hairpin may be used to separate 109 and 113 and 113, which is then just attached through hybridization, can be washed away leaving multiple copies of the starting template 109 attached to the solid support.

In a preferred aspect, the end of the hairpin is blunt so that the base at the 3' end of the hairpin is complementary to the base at the 5' end of the hairpin oligo. Alternatively the 3' end can be recessed to that the 5' end extends one or more bases beyond the last basepair of the hairpin double stranded region. In another aspect the 3' end of the hairpin may extend one or more bases beyond the 5' end when the hairpin is closed. The 3' end may be degenerate to allow for hybridization to unknown target sequences or it may be selective so that efficient extension occurs on only some targets that have complementarity to the 3' end of the hairpin.

In FIG. 1B the initial steps of target hybridization and probe extension are the same as in FIG. 1A, through the step of generating the extended probe 109. The extended probe is ligated to a double stranded adapter that includes a restriction site for a nicking restriction enzyme, shown by the triangle 121. The bottom strand of the adapter is extended to make the complement of the extended probe. In the presence of the nicking restriction enzyme the bottom strand of the adapter is cleaved to generate a nick at 123. The bottom strand of the adapter is extended from the 3' end created by the nick by a to generate a new strand 125 with displacement of the strand that is there 127. The nicking, extension and strand displacement can be repeated to generate multiple copies of 127. The displaced strands can then hybridize to adjacent probes with the same sequence as probe 101. In another embodiment the nicking of the bottom strand is accomplished by including a hemimodified restriction site as described in Walker, G. T. et al. (1992) *Proc. Natl. Acad. Sci. USA* 89, 392-396.

Advantages of this approach include, for example, strand displacement avoids high temperatures for cycling and locus specific probe can be used for sequencing. Amplified strands are associated by base pairing and can be released into solution by denaturation.

In general the probes are arranged in an array such that probes of the same sequence are present in the same area. The area may define a feature which may be, for example, a region of a support, such as a 10 micron by 10 micron two dimensional space. A feature may also be a bead. In preferred embodiments a feature contains many copies of the same probe sequence so that the probes in a feature are all complementary to the same target. In some aspects features contain a single predominant probe sequence or subsequences thereof, but a feature may also contain two or more different probe sequences.

In the embodiment shown in FIG. 1C an adapter that includes a chimeric RNA:DNA bottom strand 131 is ligated to the extended probe 109. The top strand of the adapter is ligated to the 3' end of the extended probe and the bottom strand is hybridized to the top strand. The RNA:DNA chimeric oligonucleotide is extended to generate a copy of the extended probe 133 and the RNA portion 135 is then digested using RNase H (for a description of methods for amplification of RNA using RNaseH see, for example, U.S. Pat. No. 6,686,156, US 20050064456, US 20060014182 and Kurn et al., *Clin Chem.* 51(10):1973-81, Epub 2005 Aug. 25). A second RNA:DNA chimeric primer can hybridize where the RNA portion was removed and can be extended, displacing a strand 135. This can be repeated to generate multiple copies of strand 135. The displaced strands can hybridize to adjacent probes. This method also avoids high temperatures needed for denaturation and can be done under isothermal conditions without a requirement for temperature cycling or the addition of reagents. In another embodiment the primer consists of RNA alone.

In. FIG. 1D a double stranded phage RNA polymerase promoter, such as a T7 promoter, is ligated to the end of the extended probe. An RNA transcriptase, such as T7 RNA polymerase, is used to make RNA copies 139 of the extended probe. The transcribed strands hybridize to adjacent probes and those probes may be extended in a template dependent manner using reverse transcriptase or may be extended by ligation. Using IVT (in vitro transcription) avoids high temperatures needed for cycling and the locus specific probes can be used for sequencing. Methods for performing IVT have been described in, for example, U.S. Pat. Nos. 5,545,522 and 6,040,138 and Lockhart et al., Nat Biotechnol. 1996 14(13):1675-80. The transcribed strands are not tethered and can float away and T7 transcription on an anchored template may be inefficient.

In FIG. 1E a method similar to that shown in FIG. 1C is shown but in this embodiment the top strand of the adaptor may be replaced by tailing the extended probe 109 using a terminal transferase or a polymerase that adds untemplated nucleotides, for example, polyA polymerase, and the chimeric RNA:DNA primer (SEQ ID No. 1) can include an oligo dT portion. The RNA portion may be oligo dU or a specific sequence as shown. The specific sequence may be a new priming sequence and the tailed extended probe may be extended using that sequence as a template for template directed extension so that the complement of the RNA portion is incorporated into the extended probe (shown as SEQ ID No. 2). In subsequent rounds of amplification a primer directed at the new priming sequence, or a portion of that sequence, may be used to prime synthesis of amplified strands and displace the copied strand 141.

Bridge amplification is disclosed, for example, in U.S. Pat. No. 6,300,070. Other references of interest include: Westin et al. *Nat Biotechnol.* 2000 February; 18(2):199-204., Walker et al., *Proc Natl Acad Sci USA*. 1992 Jan. 1; 89(1):392-6, Shapero et al., *Genome Res.* 2001 November; 11(11):1926-34, and Ju et al., *Proc Natl Acad Sci USA*. 2006 Dec. 26; 103(52):19635-40. Epub 2006 December. In general, one end of the target to be amplified is tethered via a first probe and the other end is free to hybridize to a second probe that is physically close enough to the first probe so that hybridization can occur. The distance within which a second probe can be located will be determined by the length of the target.

The methods disclosed herein provide for amplification of selected nucleic acids. Nucleic acid amplification has extensive applications in gene expression profiling, genetic testing, diagnostics, environmental monitoring, resequencing, forensics, drug discovery, pharmacogenomics and other areas. Nucleic acid samples may be derived, for example, from total nucleic acid from a cell or sample, total RNA, cDNA, genomic DNA or mRNA. Many methods of analysis of nucleic acid employ methods of amplification of the nucleic acid sample prior to analysis. A number of methods for the amplification of nucleic acids have been described, for example, exponential amplification, linked linear amplification, ligation-based amplification, and transcription-based amplification. An example of exponential nucleic acid amplification method is polymerase chain reaction (PCR) which has been disclosed in numerous publications. See, for example, Mullis et al. *Cold Spring Harbor Symp. Quant. Biol.* 51:263-273 (1986); and U.S. Pat. Nos. 4,582,788 and 4,683,194.

Nucleic acid amplification may be carried out through multiple cycles of incubations at various temperatures, i.e. thermal cycling or PCR, or at a constant temperature (an isothermal process). An example of an isothermal amplification technique involves a single, elevated temperature using a DNA polymerase that contains the 5' to 3' polymerase activity but lacks the 5' to 3' exonuclease activity. As the new strand of DNA is synthesized from the template strand of DNA, the complementary strand of the DNA target is displaced from the original DNA helix. The use of specific primers that invade the target DNA strand allows for self-sustaining amplification and detection techniques and can detect very low copy targets. Isothermal amplification methods, such as strand displacement amplification (SDA), are disclosed in U.S. Pat. Nos. 5,648,211, 5,824,517, 6,858,413, 6,692,918, 6,686,156, 6,251,639 and 5,744,311 and U.S. Patent Pub. No. 20040115644 and in Walker et al. *Proc. Natl. Acad. Sci. U.S.A.* 89: 392-396 (1992); Guatelli, J. C. et al. *Proc. Natl. Acad. Sci. USA* 87:1874-1878 (1990), which are incorporated herein by reference in their entirety.

When a pair of amplification primers is used, each of which hybridizes to one of the two strands of a double stranded target sequence, amplification is exponential. This is because the newly synthesized strands serve as templates for the opposite primer in subsequent rounds of amplification. When a single amplification primer is used, amplification is linear because only one strand serves as a template for primer extension and newly synthesized strands are not used as template. Amplification methods that proceed linearly during the course of the amplification reaction are less likely to introduce bias in the relative levels of different mRNAs than those that proceed exponentially. "Single-primer amplification" protocols have been reported in many patents (see, for example, U.S. Pat. Nos. 5,554,516, 5,716, 785, 6,132,997, 6,251,639, and 6,692,918 which are incorporated herein by reference in their entirety).

Nucleic acid amplification techniques may be grouped according to the temperature requirements of the procedure. Certain nucleic acid amplification methods, such as the polymerase chain reaction (PCR, Saiki et al., *Science*, 230: 1350-1354, 1985), ligase chain reaction (LCR, Wu et al., *Genomics*, 4:560-569, 1989; Barringer et al., *Gene*, 89:117-122, 1990; Barany, *Proc. Natl. Sci. USA*, 88:189-193, 1991), transcription-based amplification (Kwoh et al., *Proc. Natl. Acad. Sci., USA*, 86:1173-1177, 1989) and restriction amplification (U.S. Pat. No. 5,102,784), require temperature cycling of the reaction between high denaturing temperatures and somewhat lower polymerization temperatures. In contrast, methods such as self-sustained sequence replication (Guatelli et al., *Proc. Natl. Acad. Sci. USA*, 87:1874-1878, 1990), the Q.beta. replicase system (Lizardi et al., *BioTechnology*, 6:1197-1202, 1988), and Strand Displacement Amplification (SDA—Walker et al., *Proc. Natl. Acad. Sci. USA*, 89:392-396, 1992a, Walker et al., *Nuc. Acids. Res.*, 20:1691-1696, 1992b; U.S. Pat. No. 5,455,166) are isothermal reactions that are conducted at a constant temperature, which are typically much lower than the reaction temperatures of temperature cycling amplification methods.

The Strand Displacement Amplification (SDA) reaction initially developed was conducted at a constant temperature between about 37° C. and 42° C. (U.S. Pat. No. 5,455,166). This temperature range was selected because the exo-klenow DNA polymerase and the restriction endonuclease (e.g., HindII) are mesophilic enzymes that are thermolabile (temperature sensitive) at temperatures above this range. The enzymes that drive the amplification are therefore inactivated as the reaction temperature is increased. Isothermal SDA may also be performed at higher temperatures, for example, 50° C. to 70° C. by using enzymes that are thermostable. Thermophilic SDA is described in European Patent Application No. 0 684 315 and employs thermophilic restriction endonucleases that nick the hemimodified restriction endonuclease recognition/cleavage site at high temperature and thermophilic polymerases that extend from the nick and displace the downstream strand in the same temperature range.

Attempts have been made over the years since the invention of PCR to increase the multiplex level of PCR. Some of the strategies include two-stage PCR with universal tails (Lin Z et al., PNAS 93: 2582-2587, 1996; Brownie J. et al., Nucleic Acids Res. 25: 3235-3241, 1997), solid-phase multiplex PCR (e.g., Adams and Kron, U.S. Pat. No. 5,641,658; Shapero et al., Genome Res. 11: 1926-1934, 2001), multiplexed anchored runoff amplification (MARA, Shapero et al., Nucleic Acid Res. 32: e181, 2004 and U.S. Pat. No. 7,108,976), PCR with primers designed by a special bioinformatical tool (Wang et al., Genome Res. 15: 276, 2005), selector-guided multiplex amplification (Dahl F et al., Nucleic Acids Res. 33(8): e71, 2005), and dU probe-based multiplex PCR after common oligo addition (Faham M and Zheng J, US patent Publication No. 20030096291 and Faham M et al., PNAS 102: 14717-14722, 2005). Multiplex PCR methods are also disclosed in U.S. Patent publication Nos. 20030104459. See also, Nilsson et al., *Trends. Biotechnol.* 24(2):83-8, 2006 and Stenberg et al., NAR 33(8): e72, 2005. Methods for multiplex amplification of specific groups of targets using circularization have recently been disclosed for example, in Fredriksson et al. NAR 2007, 35(7):e47 and Dahl et al., NAR 33, e71 (2005). See also, US Patent Pub. 20050037356. Each of these references is incorporated herein by reference in its entirety. The current disclosure is related to US Patent Pub. No. 2008-0199916 and U.S. Pat. No. 7,108,976, the entire disclosures of which are incorporated herein by reference in their entireties.

In preferred aspects the methods are performed in a multiplex fashion for the simultaneous analysis of many different targets. For example, more than 100 to 1000, 1,000 to 10,000, 10,000 to 100,000 or more than 100,000 different targets may be amplified by the methods disclosed herein and analyzed. Analysis may be for example, for presence or absence of target sequences, to genotype polymorphisms (for example SNPs or CNPs) in a sample or for analysis of methylation status.

The methods disclosed herein are related to methods disclosed in other co-pending patent applications. Methods for isothermal locus specific amplification are disclosed in US Pat Pub 20070020639. Methods for genotyping with selective adaptor ligation are disclosed in US Pat Pub 20060292597. Methods for reducing the complexity of a genomic sample are disclosed in US Patent Pub, No. 20060073511. Genotyping arrays are disclosed, for example, in US Patent Pub. Nos. 20070065846 and 20070048756. Methods for adding common primers to the ends of target sequences for multiplex amplification are disclosed in US Patent Pub. No. 20030096291. Methods for identifying DNA copy number changes are disclosed in US Patent Pub. Nos. 20060134674 and 20050064476. Each of these disclosures is incorporated herein in its entirety for all purposes.

Kits for amplification using strand displacing polymerases, such as phi29, in combination with random primers are commercially available. This material may be purified, fragmented, for example using a nuclease such as DNase I, and end-labeled with TdT and DLR and hybridized to an array, for example, a SNP genotyping array such as the SNP 6.0 array from Affymetrix.

The fragmentation process produces DNA fragments within a certain range of length that can subsequently be labeled. The average size of fragments obtained is at least 10, 20, 30, 40, 50, 60, 70, 80, 100 or 200 nucleotides. Fragmentation of nucleic acids comprises breaking nucleic acid molecules into smaller fragments. Fragmentation of nucleic acid may be desirable to optimize the size of nucleic acid molecules for certain reactions and destroy their three dimensional structure. For example, fragmented nucleic acids may be used for more efficient hybridization of target DNA to nucleic acid probes than non-fragmented DNA. According to a preferred embodiment, before hybridization to a microarray, target nucleic acid should be fragmented to sizes ranging from about 50 to 200 bases long to improve target specificity and sensitivity.

Labeling may be performed before or after fragmentation using any suitable methods. The amplified fragments are labeled with a detectable label such as biotin and hybridized to an array of target specific probes, such as those available from Affymetrix under the brand name GENECHIP®. Labeling methods are well known in the art and are discussed in numerous references including those incorporated by reference.

In preferred aspects multiple copies of DNA generated by the disclosed methods are analyzed by hybridization to an array of probes. One of skill in the art would appreciate that the amplification products generated by the methods are suitable for use with many methods for analysis of nucleic acids. Many different array designs are available and are suitable for the practice of this invention. In some aspects the target is labeled and hybridized to an array where features of the array are at known or determinable locations. The feature is labeled by the interaction of the labeled target with the probe at the feature. In other embodiments the target is unlabeled and the probe on the array becomes labeled by an enzymatic process. For example, the probe may be extended using the hybridized target as a template. High density arrays may be used for a variety of applications, including, for example, gene expression analysis, genotyping and variant detection. Array based methods for monitoring gene expression are disclosed and discussed in detail in U.S. Pat. Nos. 5,800,992, 5,871,928, 5,925,525, 6,040,138 and PCT Application WO92/10588 (published on Jun. 25, 1992). Suitable arrays are available, for example, from Affymetrix, Inc. (Santa Clara, Calif.).

d) Genomic DNA Modification for Solid-Phase Amplification and Sequencing

Methods for locus-specific hybridization of whole, non-complexity reduced genomic DNA sample to DNA probe arrays followed by in-situ locus-specific solid-phase amplification and sequence determination on the array are also contemplated. The steps of a preferred embodiment are illustrated in FIG. 2. Firstly, genomic DNA 201 is fragmented randomly into a collection of fragments 203 of approximately 50 to 300 bp in length. This can be accomplished, for example, using DNaseI, mechanical shearing or by random primed extensions of the genomic DNA template. Next, adaptors 205 (or DNA ends) containing user-defined sequences (such as common priming sites, Phage promoters for IVT, or restriction recognition site sequences or other utilities) are added onto each DNA fragment to generate adaptor ligated fragments 207. The adapters are typically double stranded and may be the same or different.

For simplification purposes a single fragment is shown with adaptors in subsequent steps, but all fragments are substrates for adaptor ligation. Adaptor ligation can be accomplished, for example, via random priming with primers harboring the user-selected sequences in addition to the random bases, or by DNA ligase action to join the adaptors to the fragment ends. The adaptors preferably contain universal primers such that when ligated to the ends of the DNA fragments they can serve as PCR amplification priming sites in a PCR reaction to obtain amplified adaptor ligated fragments 209. During PCR amplification, the complexity may be reduced because PCR will preferentially amplify fragments that fall within a size range, for example, about 200 to about 2000 bases. The amplification step can be skipped if the input genomic DNA is of sufficient quantity. Amplified (or un-amplified) end-tagged genomic DNA is hybridized to an array 211 that has probes 213 that are target 215 specific and oriented in the 5 to 3' direction so that the 3' end is available for extension. Target 215 is shown hybridized to its complementary probe 213 to form a probe:target complex. The probe is extended at the 3' end using the target as template to form an extended probe 217 that is part of a double stranded complex 219. The extended probe can then be used as template for making multiple copies of the target 221. Amplification may be by any means known to one of skill in the art, including, for example, IVT using an RNA polymerase such as T7 RNA polymerase, strand displacement from a nick generated, for example, by a nicking restriction enzyme or the use of a chimeric RNA/DNA primer with RNase H and strand displacement (for a description of methods for amplification of RNA using RNaseH see, for example, U.S. Pat. No. 6,686,156, US 20050064456, US 20060014182 and Kurn et al., *Clin Chem.* 51(10):1973-81, Epub 2005 Aug. 25). The amplified strands that are generated 221 may be used as templates for a sequencing reaction. For example, the amplified strands 221 may hybridize to an un-extended probe 223 on the array and probe 223 may be extended with labeled nucleotides to determine the sequence of one or more bases in the target 215. Probe 223 may be on array 221 or on a different array, but in preferred aspects probe 223 and probe 213 are in close proximity and may be part of the same feature of the array. For example, if the feature is a bead, probes 213 and 223 may be attached to the same bead. Solid supports 211 and 225 are, in preferred embodiments, the same.

DNA fragments 211 specifically hybridized to the arrayed probes are used as templates in a polymerase extension assay which strand polymerizes the array DNA probe to incorporate the hybridized genomic sequence along with the user-defined end-tag sequence. The double stranded DNA can now serve as a template for linear amplification reactions performed on the array (in-situ). For example, if a T7 adaptor is incorporated, the T7 RNA polymerase can be used to generate RNA transcripts. If a nicking restriction enzyme site is added via the end-adaptor, the restriction can be used to nick the DNA to initiate strand-displacement amplification. It may also be possible to use a RNA/DNA chimeric primer to initiate polymerization with subsequent cycles re-initiated by the presence of RnaseH.

Solid phase amplified DNAs immediately hybridize to the neighboring locus-specific array probes which are in close proximity to the DNA synthesis sites. These array probes can now serve as "primers" in single-base extension reactions where each of the 4 bases to be extended is differentially labeled. The nucleotides may also contain reversible terminators or removable labeling groups to permit several rounds of single-base extension and sequence determination.

In one aspect, to immobilize the amplified strands and prevent the strand displaced or T7 transcribed templates from floating in to the aqueous reaction mix, the amplification reactions can precede in a solid matrix, such as a polyacrylamide gel medium infused with the necessary enzymes, nucleotides, and other reagents necessary for the reaction.

In many of the embodiments the target hybridizes to the solid support through a sequence specific hybridization between the target and the support bound probe. The target hybridizes in a single orientation and typically a single strand is amplified instead of amplification of both strands as is common in many other amplification methods. When both strands are amplified efficiently there are two separate amplification products of different sequence and this can interfere with downstream analysis such as sequencing. Many sequencing methods that use non-specific target amplification employ additional purification steps to separate one strand from the other prior to amplification so that only one strand is amplified in the clonal amplification, other methods take steps to eliminate the signal from one of the strands.

Methods for multiplex amplification and analysis that may be combined with the presently disclosed methods have been described elsewhere. For example, Westin L, et al., *Nat Biotechnol.* 2000 February; 18(2):199-204, describes a method wherein sets of amplification primers are electronically anchored in distinct areas on the microchip, creating distinct zones of amplification and reducing primer-primer interactions, thereby increasing the efficiency of the multiplex amplification reactions. They used SDA with the microelectronic chip system because of the isothermal nature of the assay. Anchored SDA supported multiplex DNA or RNA amplification without decreases in amplification efficiency and allows multiplexed amplification and detection to be performed on the same platform. Shapero et al., *Genome Res.* 2001 November; 11(11):1926-34, describes methods for multiplexed genotyping of SNPs using PCR amplification on microspheres. The target is subjected to solid phase amplification using one primer that has a recognition site for a type IIS restriction enzyme followed by locus-specific sequence from immediately upstream of the polymorphic site. After amplification the SNP is exposed by cleavage with the type IIS restriction enzyme and interrogated by primer extension 4-color minisequencing.

In some embodiments the amplified targets are subjected to sequencing by synthesis using bases that have reversible terminators and removable labels, such as the methods disclosed in Ju et al. *Proc Natl Acad Sci USA,* 2006 Dec. 26; 103(52):19635-40. Epub 2006 December and in U.S. Pat. No. 5,547,839 and WO9210587A1, published Jun. 25, 1992. In one aspect primer is extended by a polymerase, using the target to be sequenced as template, to add a single base. The base is labeled, preferably in a base specific manner, and only a single base is added in each round because the addition of additional bases is blocked by a terminator at the 3' position as in dideoxy based sequencing. After the addition of the base the support is scanned to detect which type of base was added at each feature and the label and the terminator are removed. Another base can then be added, detected and the label and terminator removed. This can be repeated multiple times to determine the sequence of the target. In one embodiment each of the four bases, A, C, G, and T, has a differentially detectable label. The label and the terminator may be removed in the same or in a different step. Similar methods for sequencing by synthesis have also been described in, for example, EP1634963 (Adessi et al.) which also discloses methods for amplifying nucleic acid prior to sequencing. Marguilies et al. *Nature* 2005:437:326-7 describes a sample preparation and sequencing using adapter ligation, emulsion PCR amplification, and pyrosequencing of the amplified products, see also EP1590477A2 and EP1594980A2. Pyrosequencing is described for example in U.S. Pat. No. 6,258,568.

Rubina A Y, et al. Biotechniques. 2003 May; 34(5):1008 and Vasiliskov et al. Biotechniques. 1999 September; 27(3): 592 provide background information on gel-based microchips and methods for fabricating and using gel-based microchips. Vasiliskov et al. provides methods for fabricating microarrays of oligonucleotides and proteins immobilized within gel pads and Rubina et al. describes fabrication of DNA gel drop microchips.

Recent developments in sequencing technologies may be combined with the methods disclosed herein. Methods for sequencing are disclosed in Fields et al., Science 316(5830): 1441-1442 (2007), Bentley, Curr Opin Genet Dev. 16(6): 545-552 (2006), Margulies et al, Nature 437(7057):326-7 (2005), Leamon et al., Gene Therapy and Regulation Vol. 3, No. 1 (2007) 15-31, Huse et al., Genome Biology 2007, 8:R143 and Robertson et al., Nature Methods 4(8):651-657 (2007). Methods for polony PCR amplification and sequencing are described in Shendure et al, Science 309:1728-1732, (2005). For additional information see references available on the Polonator web site at Harvard. Bridge amplification methods are described in Bing et al. in the conference proceedings from the Seventh International Symposium on Human Identification, 1996, available on the Promega web site. Additional methods may be found in U.S. Pat. No. 7,115,400, PgPub. Nos. 20070207482 which describes methods for sequencing by ligation, 20070087362 and which describes polony fluorescent sequencing beads.

Genome Amplification on an Array

DNA amplification has extensive applications in genetic testing, diagnostics, environmental monitoring, resequencing, forensics, drug discovery and other areas. Genomic DNA preparations typically represent the complex DNA sequences of an entire genome. As a result it is often desirable to reduce the complexity of a genomic DNA preparation prior to analysis. Complexity reduction is a process where the complexity of a genomic DNA sample is reduced without losing the DNA sequences of interest. For example, certain regions with SNPs of interest may be selectively amplified and analyzed. The resulting sample has a reduced complexity (certain regions are not amplified or not amplified efficiently), but the regions of interest are still represented. The regions of interest may be enriched in the amplified sample.

In one embodiment of the invention, methods are provided for isothermal amplification of target DNA that has been captured on a solid support. The methods employ a capture step, a nicking step in which one strand of a double stranded DNA is cleaved while the other strand is left in tact, and an extension step. The methods preferably employ multiple rounds of nicking followed by extension of the 3' hydroxyl generated by the nicking. Nicking may be accomplished by, for example, use of a nicking endonuclease or by use of a restriction enzyme that cleaves both strands, but cleavage of one strand is blocked by use of a modified base. In many embodiments a DNA polymerase having strand displacing activity and lacking 5'-3' exonuclease activity (such as the DNA Polymerase I Large (Klenow) Fragment or similar enzymes) is used. See also U.S. Patent Pub. No. 20040115644, which is incorporated herein by reference in its entirety.

Detection of target nucleic acids from a complex sample may be enhanced by target specific amplification. For many nucleic acid analysis methods it is useful to amplify the sample to improve detection. For some methods it is may be useful to amplify the sample by methods that result in enrichment of selected target sequences. The target sequences may be sequences that will be analyzed by downstream detection methods. For example, a genomic sample may be amplified by a method that enriches for a subset of selected target sequences and those selected target sequences may be detected by hybridization to an array of probes that are designed to detect the selected target sequences or to detect features, for example, polymorphisms, in the selected target sequences. During amplification other sequences may or may not be amplified but after amplification the target sequences are enriched relative to the sequences that are not target sequences. Target sequences may be selected because they have a feature of interest such as a selected polymorphism.

Allele specific hybridization methods may be used to determine the genotype of an organism for a plurality of polymorphic positions. Much of the diversity found between individual humans is thought to be the result of variation at positions that are polymorphic in a population, meaning that some members of the population have one sequence at that position and the other members of the population have a different sequence at that position. If all members of the population have one or the other sequence the polymorphism is biallelic. It is also possible to have more than two possible alleles of a polymorphism.

In one embodiment target sequences are amplified in solid-phase using probes attached to a solid support. Target specific probes which may or may not be allele specific are attached to a solid support so that a free 3'hydroxly group is available for extension. Probes on the array may include probes that are complementary to the sense strand (sense PM probes), probes that are complementary to the antisense strand (antisense PM probes) and control probes that have a mismatch (MM) in at least one position, preferably at or near the middle position of the probe. In many embodiments the target sequences do not hybridize efficiently to the mismatch probes, as a result of the mismatch, so the MM probes will not be extended efficiently.

FIG. 3 shows allele specific probes on the array. Adaptor ligated target 303 (shown double stranded) is hybridized to a first copy of a probe 301 so that a single strand 305 hybridizes to the complementary probe. The probe is specific for a particular target of interest and may be allele specific. The "X" in the figure indicates a polymorphic position. The adaptor has a cleavage site indicated by "NS". The hybridized probe is extended to make extended probes 307 that include a copy of the 5' portion of the bound target, terminating with a copy of the adaptor sequence, including the complement of the "NS" sequence. The target is still hybridized. The target is then cleaved at the nicking site (shown by the arrow) to generate a primer 309 with a 3' OH available for extension. The extended probe 307 is not cleaved at the corresponding arrow. Cleavage may be blocked by incorporating a base that blocks cleavage (indicated by the "S". The primer generated by cleavage 309 is extended to make a copy 311 of the extended probe and releasing the 3' portion of the adaptor ligated target 313. The copy of the target 311 includes a copy of the nicking site. The released molecule 313 can hybridize to a second copy of probe 301. The cleavage and extension may be repeated multiple times to generate many copies of the target 313 that are released in solution and can hybridize to target specific probes which may be located in the same region or a nearby region.

In a preferred aspect, the probes may be allele specific and can be used to distinguish between different variants, for example, polymorphisms. The X may be a position of interest in the target, such as a polymorphic base, that can be distinguished in a hybridization based assay. The figure shows the X position being present in the probe so the complementary position in the target hybridizes to the probe. Preferably hybridization of the target to the probe may discriminate between different variations at the variable position indicated by the X so that extension is based on discrimination at the variable position. If there is a mismatch between the probe and the target at the X the target hybridization will be less efficient and the amplification will be less inefficient.

In one aspect, the first extension (of the probe after hybridization of the target 307) is done in the presence of a modified base that is resistant to restriction enzyme cleavage, for example phosphorothioate. For example, the probes on the solid support may be extended in the presence of dCTPαS at 38° C. or 65° C. in the presence of the restriction enzyme that cleaves in the adapter. The dCTPαS is incorporated into the extended probe strand so that the αS is at the cleavage site for the restriction enzyme (as shown in FIG. 3). This results in hemi cleavage at that site—the strand with the αS (the extended capture probe) isn't cleaved but the template strand is. The free 3' OH generated by cleavage may be extended in the second extension with a strand displacing polymerase using the extended capture probe as template. Multiple cycles of cleavage and extension may be performed to generate an amplified product using the extended probe is used as template.

In another aspect, after the extension of the probe using the first hybridized template, the template can be removed and a primer that is complementary to the adapter sequence may be hybridized to the extended probe and extended using the extended probe as template. The restriction enzyme is present so when the primer is extended and regenerates the restriction site it will be cleaved, but only on the new strand (the extended probe has "S" to block cleavage). A new primer is then generated and can be used to make additional copies of the extended probe.

An example of an adaptor that may be used and includes BsrI, BsmFI and N.Bpu10 I sites is:

```
                                        (SEQ ID NO 3)
   5'p-GTCCTTAGCCAGTTANNGTCCCAGGAAATCCG-3'

(SEQ ID NO 4)
   3'p-CAGGAATCGGTCAATNNCAGGGTCCTTTAGG-3'
```

The methods provide for isothermal amplification wherein the signal on the array may be amplified on the array. This may provide increased label incorporation and reduce the need for density of individual probes on an array. Because the target is amplified in a region that is co-localized with the complementary probes detection is improved. However co-localization is not required, signal amplification on the array may be used to improve signal detection when the probes are not co-localized.

In another embodiment the extension probe further comprises a region 5' or the target specific region that is common to a plurality of extension probes. This region may be incorporated into the copies of the target to incorporate a priming site into the 3' end of the target copies. The target copies may be amplified using a primer to that region and a primer to the adaptor sequence.

Figure 4:
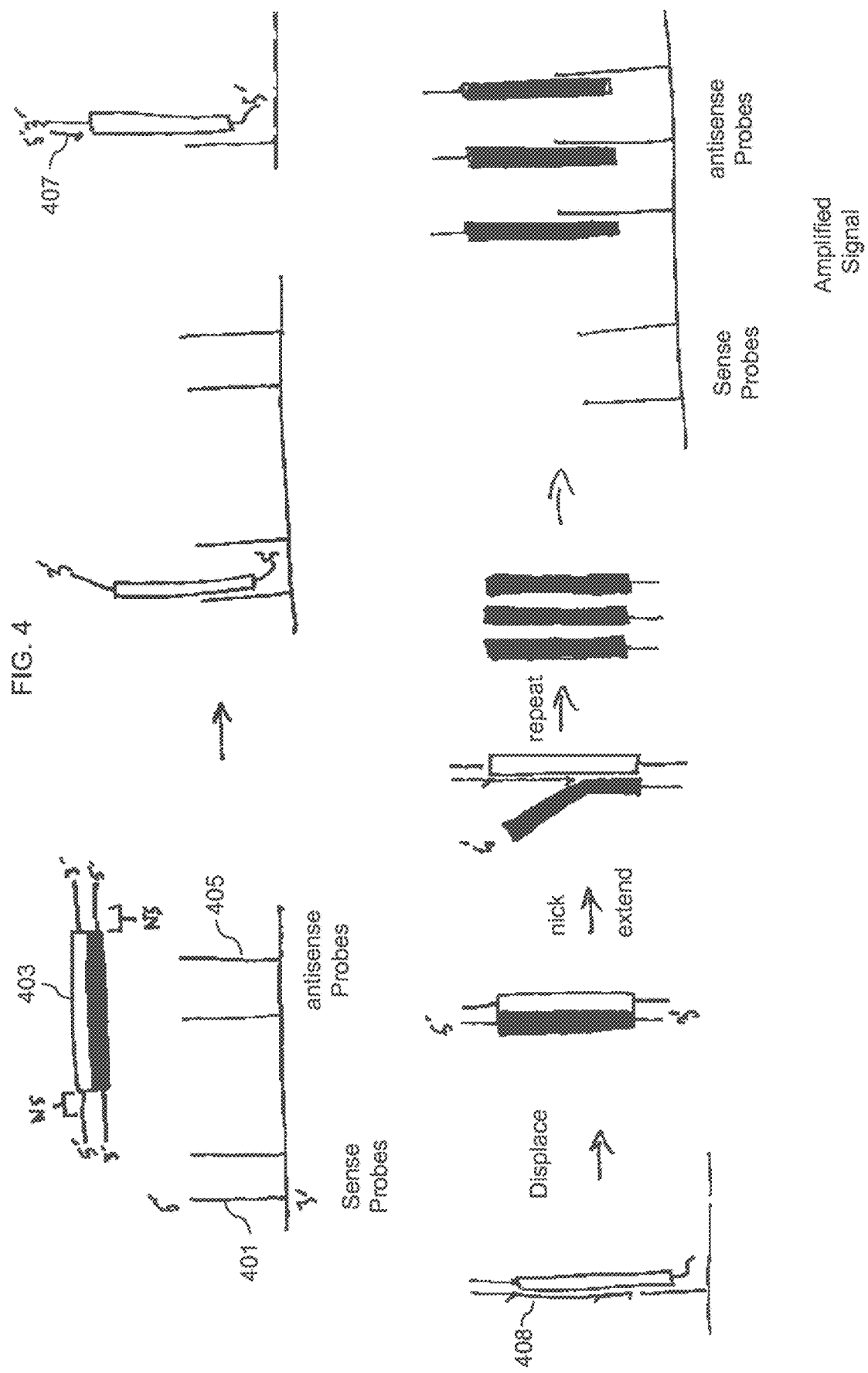
FIG. 4 shows a schematic of on-chip amplification using sense strand amplification probes and antisense strand capture/analysis probes.

In another embodiment complexity is reduced by capturing selected targets on an array of probes that are synthesized 3' to 5' and include sense and antisense probes for targets (FIG. 4). Genomic DNA is fragmented and ligated to a common adaptor sequence that contains a nicking restriction site. The adaptor ligated genomic DNA 403 is denatured and individual strands hybridize to sense probes 401. The nicking site "NS" can either be a site recognized by a nicking endonuclease or cleavage of one strand of the adaptor may be blocked by incorporation of a modified base and a restriction endonuclease may be used. After the sense strand is captured by the sense probes on the array, a primer 407 that is complementary to the adaptor is hybridized to the target strand and extended. The extended primer 408 is the same sequence as the antisense strand and displaces the sense strand from the sense probe, essentially as a copy of 403. The copy can be nicked in the adaptor as the nicking site and another copy of the primer 407 can be hybridized and extended, displacing the portion of the strand that is 3' of the nicking site, this is the antisense target strand. The conditions for cleavage and extension are the same so the regenerated nicking site may be cleaved before the first antisense strand is copied and a synthesis of a second antisense strand may begin. In this manner multiple copies of the antisense target strand are generated in a localized area, resulting in a high concentration of target in a localized area. In some aspects, the localized area includes a region of diffusible solid mater, for example, cross-linked polyacrylamide, agarose, gelatin or other similar polymers. The copies of the antisense target strand can hybridize to the antisense probes. The antisense probe feature is within or adjacent to the sense probe feature so hybridization efficiency is increased.

In some embodiments the perfect match probes are "extension capable" and will hybridize stably to the complementary target strand and may be extended. In some embodiments the mismatch probes, are "extension refractory" and are not stably hybridized to the targets and are not extended efficiently.

In some embodiments the nucleic acid sample to be analyzed, for example, genomic DNA, is fragmented and ligated to an adaptor sequence prior to hybridization to the extension probes on the solid support. In a preferred embodiment the adaptor contains a nicking restrictions site. In some embodiments the adaptor has a restriction site containing a modified base. In some embodiments the modified base is at the cleavage site of the restriction enzyme and may be used to block cleavage of one strand. Cleavage may be blocked selectively so that cleavage depends on the conditions of digestion. Under some conditions the strand with the modified base will be cleaved and under some conditions it will be resistant to cleavage.

In some embodiments the adaptor contains a restriction site for a nicking enzyme. A nicking enzyme cleaves one strand of a double stranded DNA but not the other strand. Nicking enzymes include, for example, N. Bpu10 I, N.BbvC IA, N.BbvC IB, N.BstNB I, N.Alw I, for additional information see the New England Biolabs catalog.

For each polymorphism there is a probe set including at least one allele specific capture probe. In a preferred embodiment the probe set for each allele includes between 2 and 10 allele specific capture probes that are PM probes and between 2 and 10 allele specific probes that are MM probes. The mismatch probes have at least a one base mismatch with the target so they hybridize inefficiently and should not extend efficiently. The mismatch is preferably near the 3' end of the probe. The capture probes may be attached to a solid support so that they have a free 3' hydroxyl and can be extended. Antisense PM and MM probes that are complementary to the opposite strand of the allele may also be included in the probe set.

In a preferred embodiment the target is genomic DNA that has been fragmented and ligated to an adaptor sequence. In a preferred embodiment the adapter includes a nicking restriction site. A nicking restriction site is one that can be cleaved so that only one of the two strands is cleaved. Cleavage of one strand may be blocked by, for example, inclusion of a modified nucleotide at or near the cleavage site. In one embodiment a thiophosphate is included at the cleavage site in one strand to block cleavage of that strand. In another embodiment a nicking site is one that is recognized by a restriction enzyme that nicks DNA, cleaving one strand but not the other.

The target is hybridized to the capture probes so that fragments in the target hybridize to complementary capture probes. In a preferred embodiment one strand of the double stranded target fragments hybridizes to a capture probe. The opposite strand may hybridize to the antisense probes. Those capture probes that are extension capable are then extended. In one embodiment the capture probes are extended by the addition of a DNA polymerase, dNTPs and the appropriate buffer. The capture probe is extended using the target fragment as template. Since the target fragment has one strand of the adaptor sequence at its 5' end, the extended capture probe incorporates the complement of that adaptor sequence at its 3' end-thus regenerating the double stranded adaptor sequence, including the restriction site. In preferred embodiments the restriction site is regenerated as a nicking restriction site-either by inclusion of a modified base to block cleavage in the extended capture probe or as a restriction site recognized by a nicking enzyme.

In one embodiment the capture probe is extended in the presence of at least one $dNTP_\alpha S$ so that the restriction site in the adaptor is regenerated with a thiophosphate at the cleavage site in the extended capture probe. As a result, cleavage of the extended capture probe at the restriction site is blocked while cleavage of the target strand is not blocked. If the restriction site is a site for a nicking enzyme addition of $dNTP_\alpha S$ is not necessary.

Cleavage at the nicking site generates a free 3' hydroxyl in the hybridized target strand which can act as a primer. The primer may then be extended using a strand displacing polymerase. As the primer is extended it displaces the remaining target strand bound to the extended capture probe. The released target strand may then hybridize to other capture probes in the same feature. The cleavage and extension reactions are repeated for a plurality of cycles in a preferred embodiment. At each cycle a copy of the target strand (lacking the primer region) is released and can hybridize to another capture probe. In a preferred embodiment the released target strands hybridize to probes in the same feature so the kinetics of hybridization are improved because complementary target and probe sequences are in close proximity.

In a preferred embodiment extension is done in the presence of a detectable nucleotide, for example, biotin-dATP. The released target strands have incorporated detectable nucleotide and can subsequently be detected.

In a preferred embodiment capture probes in a single feature may discriminate between different alleles of a gene, for example, a gene may contain a biallelic SNP and probes in one feature may be designed to hybridize to one allele of the SNP while probes in another feature may be designed to hybridize to the other allele.

In another embodiment target sequences are amplified by hybridizing the target sequences to complementary primer-probes on an array, extension of the primer-probes on the array and strand-peeling amplification as described above and then the target sequences are genotyped by hybridization to allele specific probes. In a preferred embodiment the primer-probes and the allele specific probes are both part of a feature of an array. For example, allele specific probes may be arranged in an interrogation block with PM and MM probes for both alleles arranged in the same feature space or in adjacent features. The reaction vessels may be, for example, square, rectangular, circular, triangular, oval, hexagonal or irregular in shape. The size of the well may be about 1 micron in diameter to about 10 mm in diameter. Each vessel is comprised of a plurality of different features. Individual vessels are shown as squares that are approximately 1 $mm^2$. The vessel may have a series of individual features in the center. Each different feature may have a different oligonucleotide sequence synthesized in that feature. The primer-probes may be synthesized in a border surrounding the interrogation block. The border surrounding the individual features may have probes that are used as primers to amplify the target. The probes in the center may be for interrogation of specific features of the RNA. For example the primer oligonucleotides may hybridize to the target downstream of a region of interest and may be used to amplify that region using the methods disclosed. The internal features may have probes to interrogate features of the region of interest, for example, the interior features may be used to genotype a SNP in the target region of interest. In another embodiment the interior features may distinguish between different spliced forms of a gene or transcript.

Reaction vessels may be formed, for example, by the following process: 1) pretreat the substrate, 2) coat with photoresist, 3) soft bake, 4) expose, 5) post expose bake, 6) develop, 7) rinse and dry, 8) hard bake, 9) chemical etching if needed, 10) removal of photoresist, 11) photolithographic synthesis of probes or spotting of pre-formed probes. Steps 9 and 10 may include surface modification for in situ probe synthesis or spotting.

In one embodiment parallel locus specific DNA amplification in a vessel may be done by depositing oligonucleotides, hybridization of template targets, washing array to remove unhybridized nucleic acid, addition of amplification reagents, sealing of the vessels, first round amplification of the target and second round amplification of the target.

Figure 5:
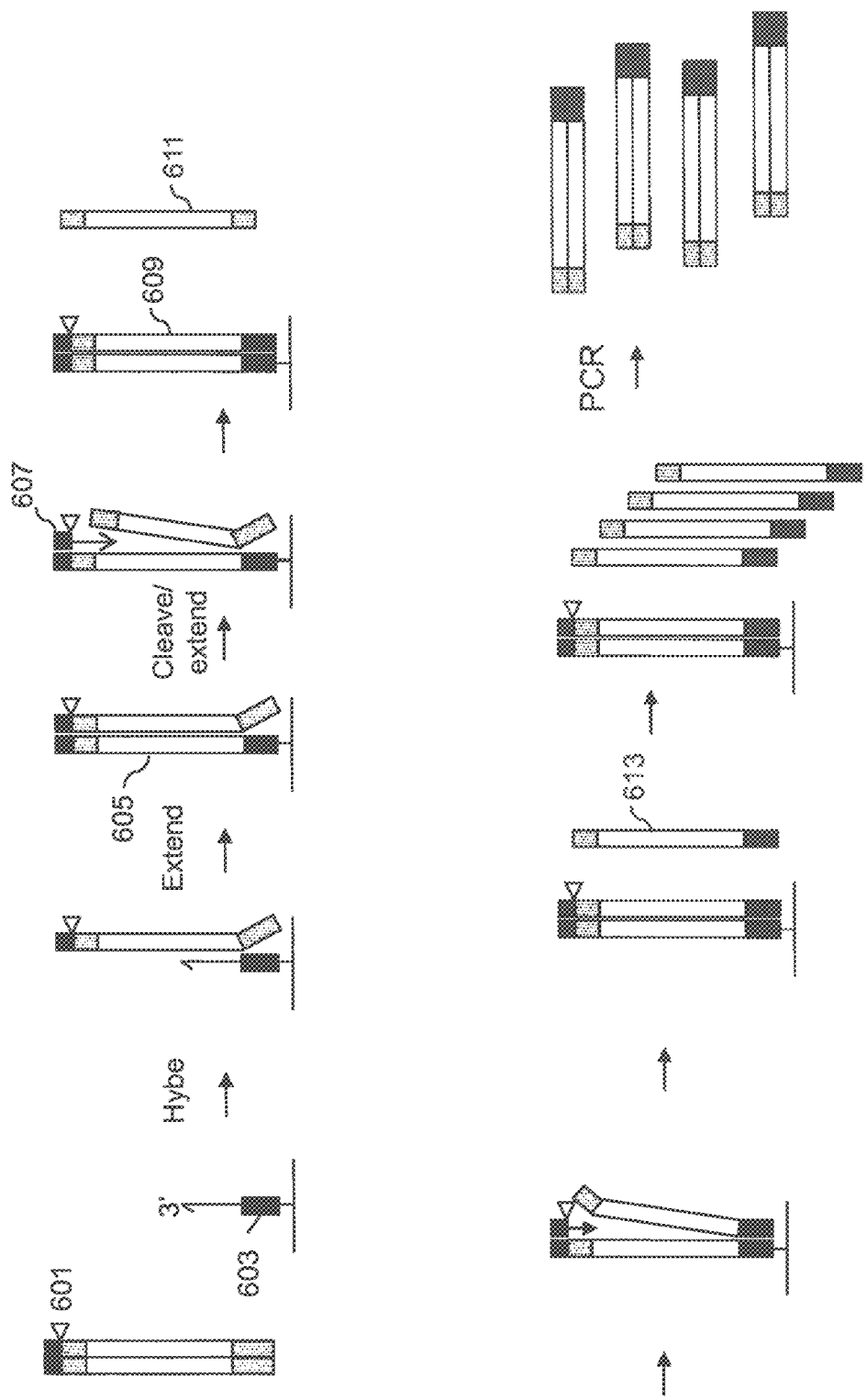
FIG. 5 shows a schematic of on-chip amplification by strand peeling where the probe has a 5' portion that is a common priming sequence.

In another embodiment illustrated by FIG. 5. the adaptor ligated genomic DNA fragments with nicking site 601 in the adaptor region are hybridized to 3' up probes that have a common priming site 603 proximal to the surface of the array. The target is hybridized to the probe on the array through target specific base pairing between the 3' region of the probe and genomic sequence within the fragment. The probe is extended using template dependent extension with the hybridized target serving as template to make an extended probe 605 that is a copy of the target including the adaptor sequence at the 5' end of the target strand. The target strand is nicked at 601 to generate a 3' site for extension from a primer 607 that is the adaptor region that was 5' of 601. The primer 607 is extended using 605 as template, thereby displacing the portion of the original target strand that was 3' of the nick site 611 and creating a new extension product 609 that includes a copy of the common priming site 603 from the probe at the 3' end of the newly synthesized copy. That newly synthesized copy 609 can be nicked and extension from the nicking site can occur releasing 613. This nicking and extending can be repeated to make multiple copies of 613 in solution. Those copies have common priming sites at both ends and can be amplified in a multiplex reaction using primers to the common priming sites, for example, by PCR. The common priming sites may be the same so that a single primer may be used for amplification. The amplification products may be detected by hybridization to the extension probes or to other probes on the same array or on a different array.

One of skill in the art would appreciate that the amplification products generated by the methods are suitable for use with many other genotyping and nucleic analysis methods. For example, oligonucleotide probes may be immobilized on beads or optical fibers. In addition, the fragments with reduced complexity may be used for sequencing, gene expression quantitation and re-sequencing applications. Resequencing by hybridization methods have been previously disclosed.

E. On Chip Clonal Amplification of Hybridized DNA Targets (ID 00182-2007)

Figure 7B:
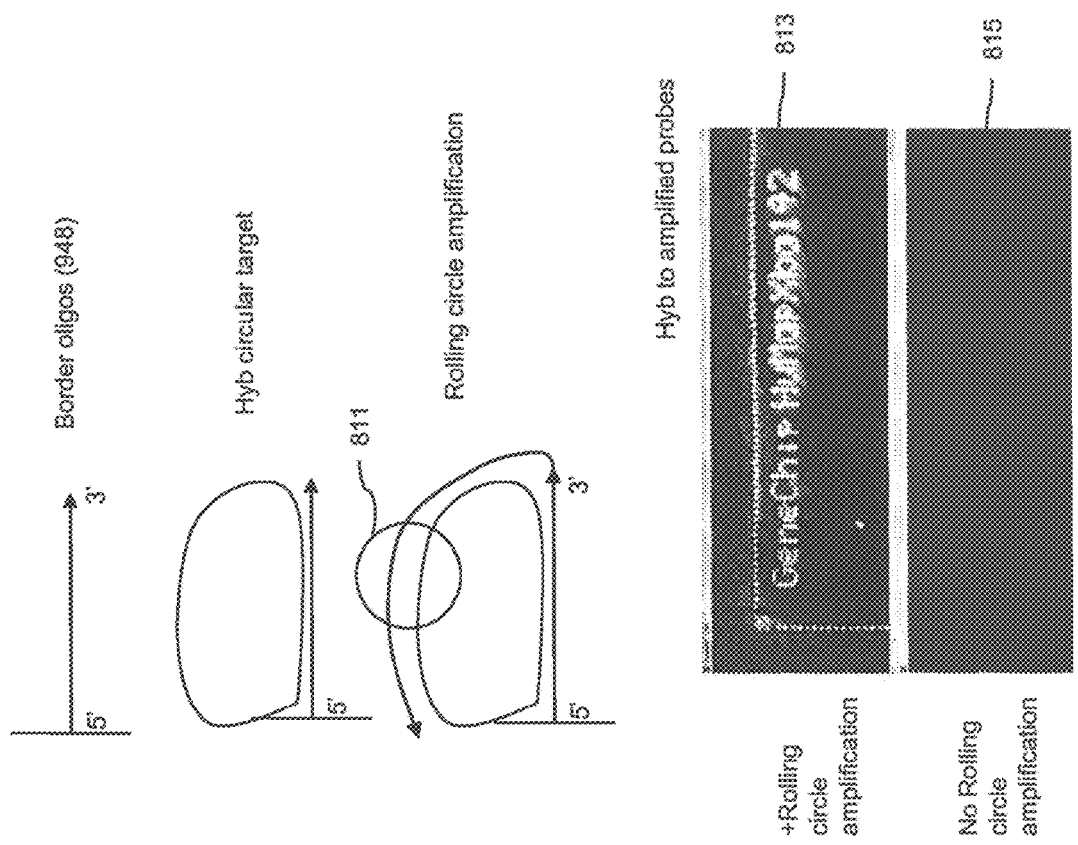
FIGS. 7A and 7B show a method for amplification of a circularized target using RCA.
Figure 7A:
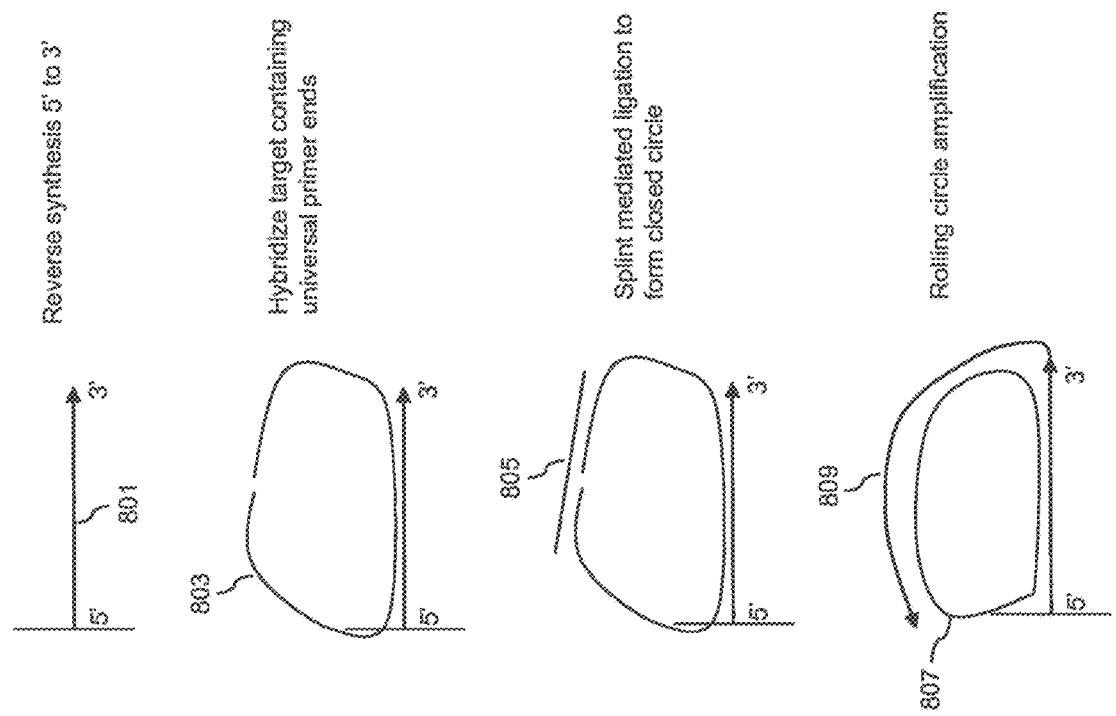

In another embodiment targets to be analyzed, for example, for sequence or for quantification of amount of a target in a given sample (e.g. copy number analysis or gene expression analysis) may be clonally amplified on an array according to the following methods. In general, as shown in FIG. 7 the targets 803 are hybridized to a target specific probe 801 attached to a solid support so that the 3' end of the probe is free to be extended. In one aspect the target contains common or known sequences at the 5' and 3' ends of the target sequence so that an oligo-splint 805 can be used to bring the ends of the target together to form a circularized target 807 (FIG. 7A). The probe is extended, for example, by rolling circle amplification (Fire and Xu, PNAS 92(10): 4641-5, 1995 and Lizardi et al. Nature Genet 19:225-232, 1998) to form an extension product 809. Nallur et al. NAR 29(23) e118 describes method for amplification of targets by rolling circle amplification on solid supports.

The extension product can be detected by hybridization of a probe to the extension product. In one aspect the probe may be complementary to a common sequence present in the circularized target, for example, if the target sequences have common sequences at the 5' or 3' ends those can be targeted for hybridization of a detection probe. The same probe can be used to detect multiple extension products. In another aspect a target specific probe may be used. In another embodiment a tag that is common to some or all of the targets may be used. In some aspects the splint oligo may be used for detection. In preferred aspects the extension product is labeled indirectly by hybridization of a labeled probe. The probe may be labeled before hybridization to the extension product or it may be labeled after hybridization. In a preferred aspect the detection probe is extended by template-dependent extension by a polymerase. In some aspects the extension reaction is a sequencing reaction and the method is used to analyze the sequence of the target in a sequencing by synthesis reaction or sequencing. In another aspect the detection probe is extended by ligation of one or more bases resulting in incorporation of one or more labeled nucleotides, for example in a sequencing by ligation reaction.

In one embodiment, arrays are synthesized with reverse MeNPOC protecting groups, as described, for example, in McGall and Fidanza, in Rampal, J B, ed. Methods in Molecular Biology DNA Arrays Methods and Protocols. Totowa N.J.: Humana Press, 2001:71-101. The array used in the example described below is a BisB surface, 5 to 3' MeNPOC 10K v2 array. BisB and methods for using BisB are described, for example, in U.S. Patent Pub. Nos. 20070238185, 20090215652 and 20090286690 and U.S. Pat. No. 7,790,389 each of which are incorporated herein by reference. Targets are hybridized to the arrays. In one embodiment they can be circularized after hybridization by enzymatic or chemical means. In another embodiment the targets may be circularized before hybridization to the arrays. Post circularization, the arrayed probes serve as primers for any DNA polymerase with a strong strand displacement activity, such as Phi29 DNA polymerase which was used in the example below. Amplification of the hybridized circular target proceeds in a rolling circle fashion, resulting in a single copy of the hybridized target being clonally amplified hundreds of times.

Current efforts are underway to find suitable means of circularizing hybridized genomic DNA targets. Some of the possible mechanisms include using oligonucleotides as splints in ligation assays. The ends of the genomic DNAs can also be tagged with universal priming sequences which may then serve as a tool not only for DNA amplification but also for use as a priming site during DNA sequencing on the arrays.

Figure 10:
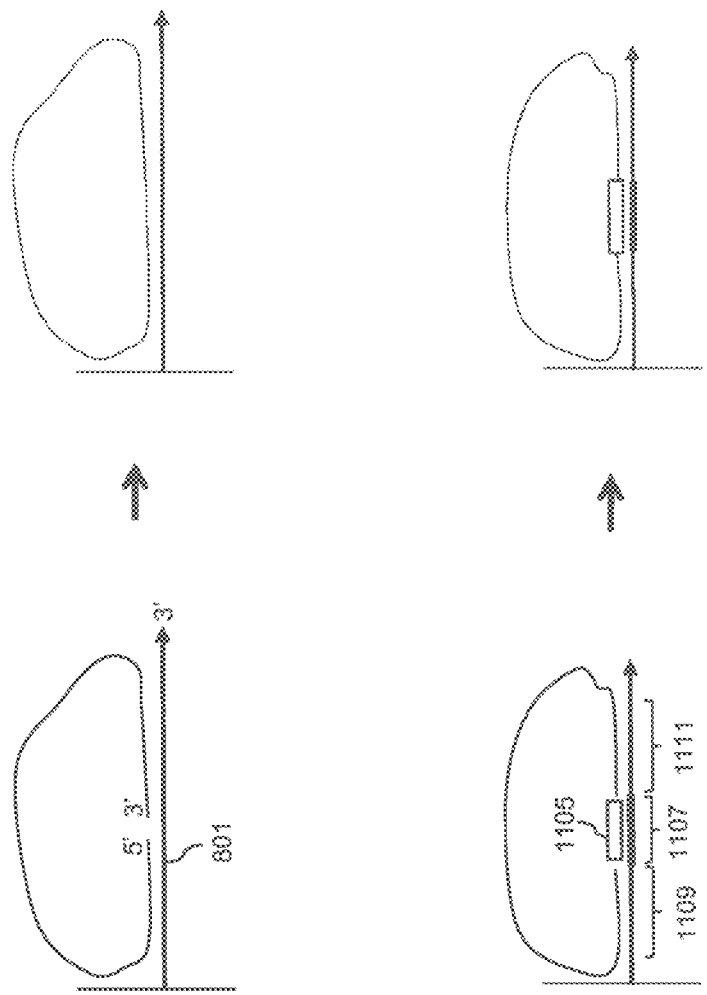
FIG. 10 shows a schematic of an RCA strategy.

FIG. 10 shows a schematic of how amplified targets can invade into neighboring features or cells and a preferred alternative whereby the amplified target is primarily localized within a feature. Condensation of the amplified surface DNA may be used to achieve feature localization. Instead of using 0.9 M NaCl (6×SSPE) the conditions were 100 mM MgCl2, 10 mM Tris pH 7.8 or 6% PEG 8000, 50 mM MgCl2, 10 mM Tris pH 7.8. The addition of various additives allows for long DNA strands to be "packaged" and confined to single features. Agents that have been shown to cause condensation in vitro include multivalent cations, for example, spermidine$^{3+}$ and spermidine$^{4+}$, the inorganic cation $Co(NH_3)_6^{3+}$, polylysine and basic histones. High concentrations of divalent transition metals also cause the aggregation of linear DNA. Alcohols including ethanol, methanol and isopropanol at levels as low as 15-20% can be used if $Co(NH_3)_6^{3+}$ is present. Neutral crowding polymers like PEG at high concentrations and in the presence of adequate concentrations of salt can result in condensation through excluded volume mechanisms. Polyvinylpyrrolidone or albumin can be used. The necessary concentration of PEG decreases with increasing degree of polymerization and salt concentration. Cationic liposomes may also be used to condense DNA.

FIG. 10 shows a schematic of an RCA strategy. In one embodiment, shown in the upper portion of the figure, linear DNA target is hybridized to an array probe in an inverted manner (5' end of target adjacent to 3' end of target), so the ends can be joined. The gap may be closed with T4 DNA ligase prior to rolling circle amplification. In another embodiment, shown below, the linear DNA target hybridizes as an inversion and a universal sequence 1105 hybridizes between the ends of the single stranded target fragment. The array probe included 3 regions, a 5' region 1109 that is complementary to a 5' region, preferably the 5' 10 or 20 bases, of the target fragment, a central region 1107 that is complementary to the universal sequence 1105 and a 3' region 1111 that is complementary to a 3' region, preferably the 3' 10 to 20 bases, of the target fragment. A 2 point ligation is performed using T4 DNA ligase to form a closed circle RCA template with a universal priming site. The method incorporated a universal sequence into the amplified DNA.

Figure 11:
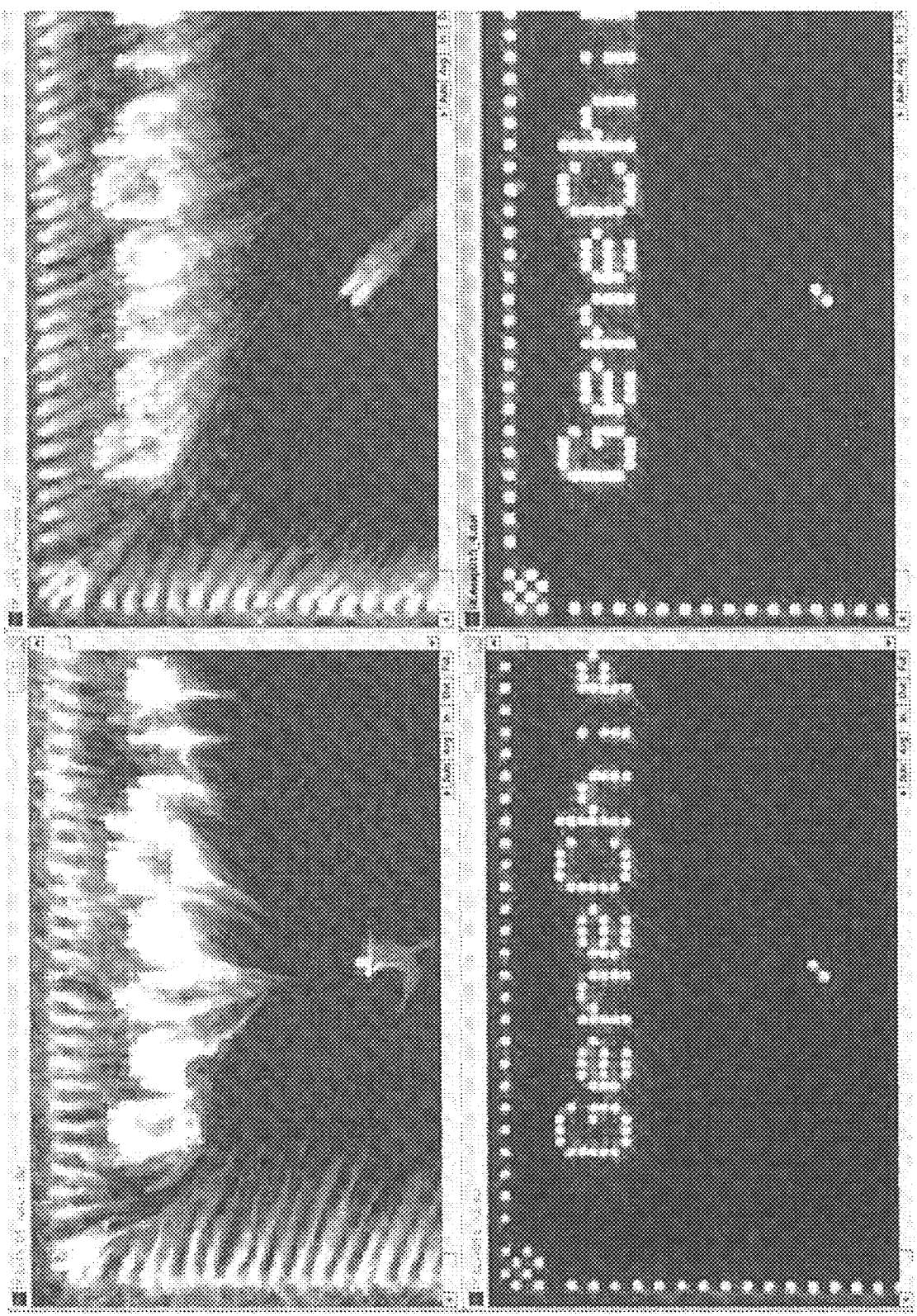
FIG. 11 shows condensation of the RCA product on the array under different conditions.

In some aspects methods for condensing or aggregating the RCA products into a smaller space may be preferred. FIG. 11 shows array images showing the effect of condensation of the amplicons on the array surface DNA under different conditions. The results demonstrate that long DNA strands can be packaged and confined to single features under selected buffer conditions. The top two panels (0.9M NaCl (6×SSPE)) show an earlier embodiment and the bottom two panels show improved conditions. 100 mM MgCl2, 10 mM Tris pH 7.8 and 6% PEG 8000, 50 mM MgCl2, 10 mM Tris pH 7.8.

A method for amplification is shown in FIG. 12. Genomic DNA 1301 is fragmented to generate a collection of fragments 1303. Fragmentation preferably generates predictable or defined ends, for example, restriction fragmentation. The fragments are hybridized to probes on an array to form an inverted structure 1305 such that the 5' and 3' ends are directed toward one another and so that there is a gap between the ends of the fragments. The array probe has two regions that are complementary to sequences at the ends of the target (in opposite orientations) separated by a gap region. The gap region contains a universal sequence. An oligo 1307 that is complementary to the universal sequence is hybridized to the array probes between the ends of the hybridized fragments. The oligo can be hybridized before the target is added, after the target is added or at the same time as the target. Each end of the fragments is ligated to one end of the oligo, for example, by ligation, so the target and the oligo form a closed circular target 1309. The array probe is extended using RCA with the closed circle as a template. The extended probe now has multiple copies of the target separated by the universal sequence. The universal sequence in the extended probe can be used as a priming site for sequencing of the target complement using, for example, sequencing by incorporation of labeled bases or sequencing by ligation.

Locus capture, target amplification and readout can be performed on the same array or solid support. Cut genomic DNA with a first selected 4 base cutter restriction enzyme. Hybridize to an array where the probes of the array have the complement of a universal priming sequence. Do the 2-way ligation and incorporate the priming site into the closed circle. Each hybridized target is clonally amplified into hundreds of copies or more that are covalently attached to the array. Sequencing can be performed on the array using standard methods. One method is shown. Each of the different dNTPs is labeled with a differentially detectable label. This can be by, for example, sequencing by incorporation or sequencing by ligation. The universal priming site can be used to facilitate sequencing.

In some aspects rolling circle amplification is performed with a strand displacing polymerase using a primer that is attached at the 5' end to a solid support and is extended from the 3' end. The RCA template can be hybridized to a probe on the array as a linear DNA molecule with inverted ends that can then be ligated with T4 DNA ligase on the array to form closed circular templates. The template can hybridize to the probe so that the ends are immediately adjacent so that they can be ligated directly, or there can be a gap that can be extended to include a portion of the probe sequence and then the ends can be ligated or a segment can be ligated onto the first end and the end of that segment ligated to the second end of the template. The amplification products are long DNA strands that stretch beyond a single feature on the array. In preferred embodiments the products are exposed to conditions, for example, the presence of cationic solutions, in which the long products condense and pack into a single feature enabling accurate intensity determination.

FIG. 13 shows results and a schematic of 2 point ligations for formation of closed circular templates on the array. The upper panel shows results of RCA using a circularized target. The center panel shows RCA starting with a linear target and performing a 2 point ligation to close the linear gapped target into a circle. The lower panel has no target. The detectable signal in the upper and middle panel (see the "Longmer 4c1") demonstrates that RCA is occurring and in the middle panel the signal demonstrates that the two point ligation occurs. DNA ligase efficiently closes the gap in the presence of a gap oligo. The gap oligo 1401 can serve as a universal priming sequence for downstream applications.

Figure 14:
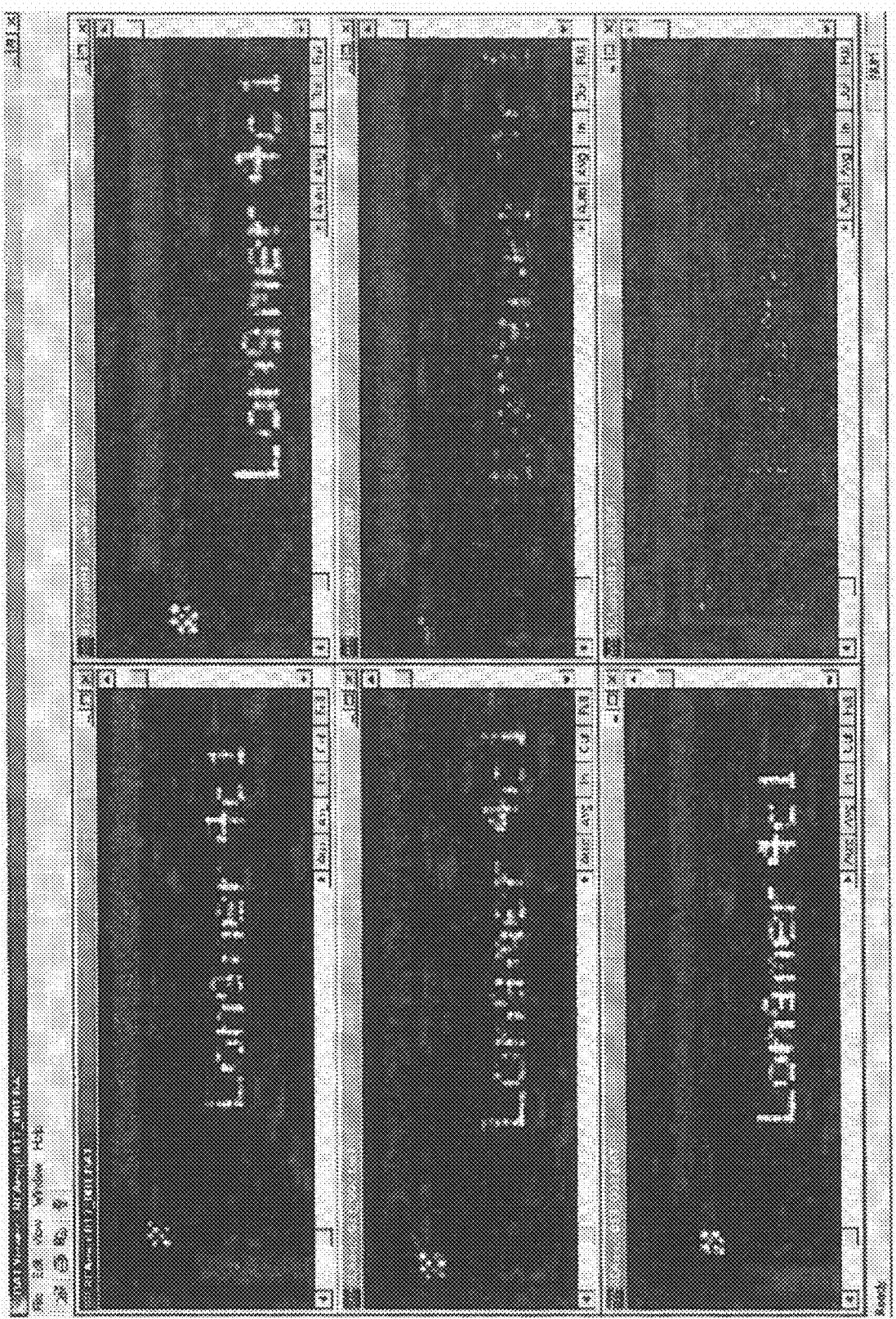
FIG. 14 shows the results of analysis of the detection sensitivity of an RCA method using different starting targets.

FIG. 14 shows the results of analysis of the detection sensitivity of an RCA method. Clockwise from upper right: 1) 10 pM linear 2 point ligation, no hsDNA, 2) 1 pM circular no hsDNA, 3) 1 pM linear 2 point ligation no hsDNA, 4) 10 pM circular no hsDNA, 5) 10 pM linear 2 point ligation plus hsDNA, and 6) 10 pM circular plus hsDNA. Circular control targets or gapped linear targets were hybridized at various concentrations with or without herring sperm DNA (serving as complex target background). 10 min SAPE stain on complement oligo to gap sequence was used for detection (no antibody amplification). The results indicate that under these conditions detection falls off at 1 pM target concentration. The probes on the array are 70 mer probes with 30 bases hybridized on either side of the gap. Target concentrations of greater than or equal to about 1 pM are preferred. Target concentrations of about 10 pM or greater are more preferred. In some aspects the target concentration can be between 0.5 pM to 3 pM is disclosed. 1 to 10 pM is another range that may be used.

During the RCA the universal gap sequence is amplified along with the hybridized target sequences, serving as a priming site for downstream reactions. Improved sensitivity may be achieved by varying hybridization and wash conditions, probe length, position of the universal gap sequence in the probe, feature size and setback.

The following different conditions were tested: 8% PEG8000, 8% PEG8000 without formamide, no PEG, no formamide, no stringency wash, or standard conditions. The standard conditions (0.8 pM target, 40 hr hybridization, formamide, and stringency wash) were used except as noted. The results indicate that the use of volume excluding reagents improved detection. Increased hybridization time may also improve detection. The conditions where PEG8000 and formamide are both included performed best in this example.

Figure 15:
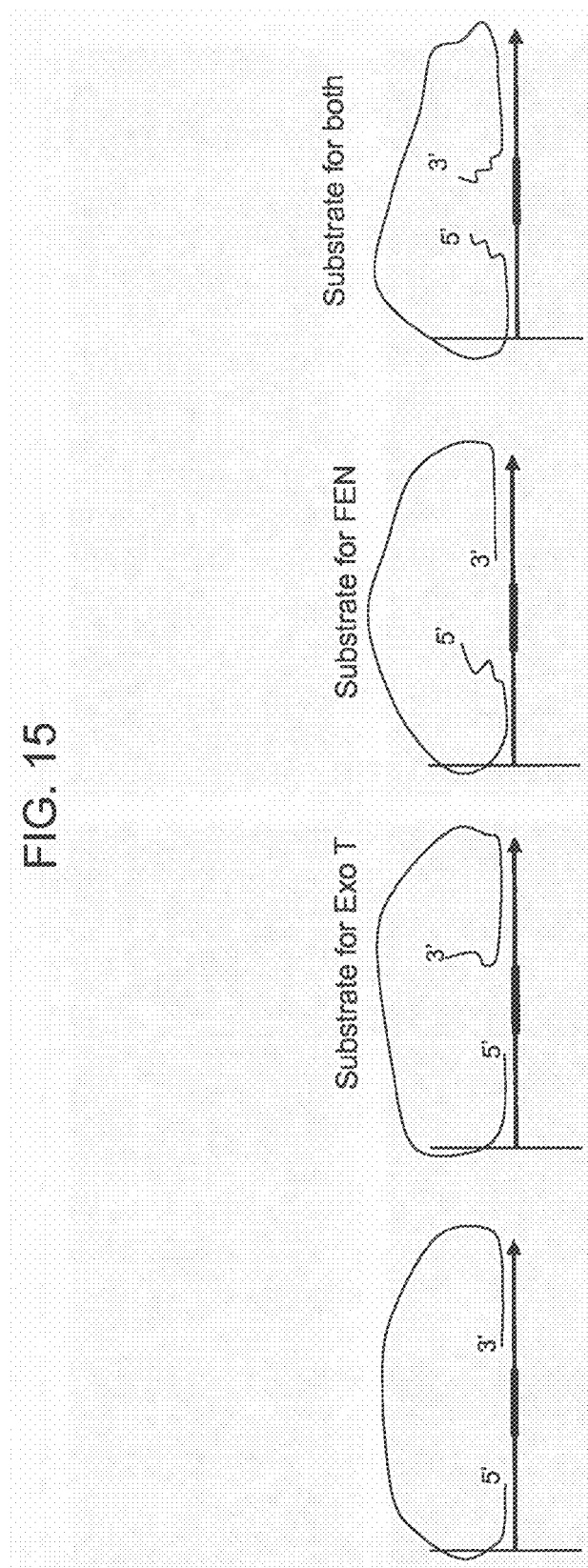
FIG. 15 shows a schematic of random fragments access.

FIG. 15 shows a schematic of a method for circularization of randomly fragmented genomic DNA targets. The targets may hybridize to the array probe with no overhangs, with a 3' overhang, with a 5' overhang or with both a 3' and 5' overhang. Enzymatic methods can be used to remove the overhangs, for example Exo T for the 3' overhang, FEN for the 5' overhang or a combination if both 5' and 3' overhangs are present. In many aspects, the probe is 3' up and available for extension in the same reaction that the gap between the ends of the target is being extended. In some aspects it may be preferable to block the extension of the probe during the gap fill reaction as there may be a competition between extension of the probe and formation of the closed circle. In a preferred aspect the 3' end of the probes that will be used for extension, for example for RCA, may be reversibly blocked during the gap fill reaction. After the gap fill and ligation the blocking may be reversed so the array probes can be extended. In a preferred aspect the 3' up probes are blocked with a phosphate group. After gap fill and ligation to form the closed circle template the phosphate may be removed, for example, by treatment with T4 polynucleotide kinase. Then the 3' up probe can be extended using the circularized target as template. Alternative blocking groups include the acid sensitive protective group dimethoxytrityl (DMT) (see also US Patent Pub. 20090215652), and the inclusion of a mismatch base that is removed prior to extension.

Figure 16:
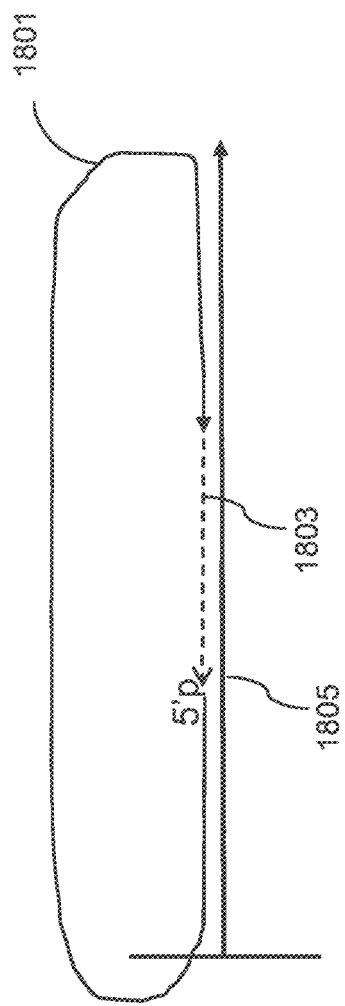
FIG. 16 shows schematically a method of extending the target through a gap prior to circularization.

FIG. 16 shows a schematic of a method whereby the hybridized pre-circle target 1801 is extended using the array probe 1805 as template to fill in the gap between the two ends of the target. The extended portion 1803 is shown as a dashed line. Using this method different conditions of extension followed by ligation and RCA were tested. The following reaction conditions were tested: (i) T4 DNA polymerase plus ligase, (ii) DNA polymerase I plus ligase, (iii) klenow plus ligase, and (iv) klenow exo-plus ligase. Long RCA products were not apparent, indicating that RCA was inefficient. This may result from strand displacement activity of the polymerases used. Each of the enzymes used has some strand displacement activity that could remove the template from the probe. In preferred aspects polymerases with reduced or no strand displacing activity may be used or conditions that disfavor strand displacement. For example, increased amounts of ligase and reduced amounts of polymerase may increase the likelihood of ligation to close the circle instead of strand displacement. In some aspects the probe may be circularized so that it includes one or more uracil bases so that the circle can be linearized by cleavage with UDG.

Figure 17:
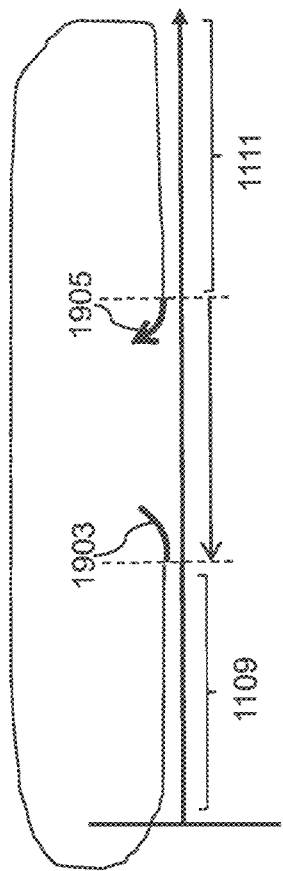
FIG. 17 shows a schematic of a target that hybridizes to the array probe with overhangs that can be cleaved using a flap endonuclease.

FIG. 17 shows a method wherein one or more single stranded exonucleases is used for the digestion of single stranded overhangs. The following combinations were tested: (i) a 3' overhang with Exo VII, (ii) no overhang with Exo VII, (iii) no overhang and no Exo VII, (iv) a 5' and a 3' overhang with Exo VII and (v) a 5' overhang with Exo VII. The conditions tested did not result in efficient amplification as detected by hybridization, but with optimization this method is expected to generate the expected results. For example, the use of exonuclease resistant array probes may facilitate amplification.

In this aspect the ends of the fragments need not be known because the free end portions of the target that are not hybridized to the probe can be digested using a flap endonuclease for example, FEN 1 or an exonuclease, for example, Exo VII. This allows the targets to be fragmented by methods that may not produce predictable or known ends, such as shearing or DNase. As shown in the schematic, the target hybridizes to the array probe so that there is a gap between the target/probe complementary regions and there may be single stranded regions 5' 1903 and/or 3' 1905 of the double stranded regions. The array probe regions 1109 and 1111 are complementary to sequences that need not be at the ends of the target fragments. The single stranded regions at the ends can be digested to remove the overhangs, leaving ends that correspond to the ends of the gap. The array probes are used to define the fragments that will be amplified by RCA. The amplicons will include those regions that are bound by the 5' and 3' target regions in the array probes, but not the regions 1903 and 1905 that are outside of the regions bound to the array probe at 1109 and 1111. Overhangs are removed with a single stranded exonuclease, for example Exo VII, before circularization with ligase. This method allows for more flexibility in selection of targets as they need not be defined by restriction sites. Exo VII (available from USB) has both 5' and 3' exonuclease activities on single stranded and may be used or a combination of enzymes, for example one enzyme with 5' single stranded exo activity and a second enzyme with 3' single stranded exonuclease activity may be used. The array probes may be used to define any locus or combination of loci in the genome to amplify. In a preferred aspect, the ends of the array probes may be protected from digestion by the exonuclease. For example, the 3' end of the probe may contain exonuclease resistant nucleotides such as phosphorothioate linkages. The schematic shows the array probe having a central region, this is optional and may be filled by extension of the target or by ligation of an oligonucleotide as described above.

For additional information on methods for removal of flaps see US Patent Pub. 20080199916 which is incorporated herein by reference for a description of methods of removing overhangs from targets hybridized to juxtapose ends for ligation. Where a 5' flap nuclease is used, a 5' to 3' ssDNA exonuclease, such as RecJ or Exo VII (which contains both 5' to 3' and 3' to 5' exonuclease activities), may be used to shorten the length of the 5' flap. By doing this, the efficiency of the removal of long 5' flaps (for example, greater than 50 bases) may be increased, since the removal efficiency is dependent on flap length, although very good cleavage can be obtained up to at least 500 bases in most cases. In another aspect Dna2 may be used to shorten the 5' and 3' flaps. See Kim et al., Nucleic Acids Res. 34:1854-1864 (2006), Stewart et al. JBC 281:38565-38572 (2006) and Stewart et al. 2009, 284(13):8283-8289. In another aspect the endonucleolytic activity of Taq polymerase may be used to recognize the specific branched structure formed by the flap. See Lyamichev et al., *Science* 1993: 260:778-783. In some aspects, the lengths of the flaps may be, for example, 1 to 500 bases or 1 to 1,000 bases. The length of the targets to be amplified may be, for example, about 100 to 1,000 or 2,000 bases, but the targets may be longer, for example, 2,000 to 10,000 basepairs or larger.

Other single stranded exonucleases include Exonuclease I, Exonuclease T, Lambda Exonuclease and T7 Exonuclease. In another aspect flap structure-specific endonucleases may be used. FEN1 encodes a human enzyme that removes 5' overhanging flaps.

Figure 18:
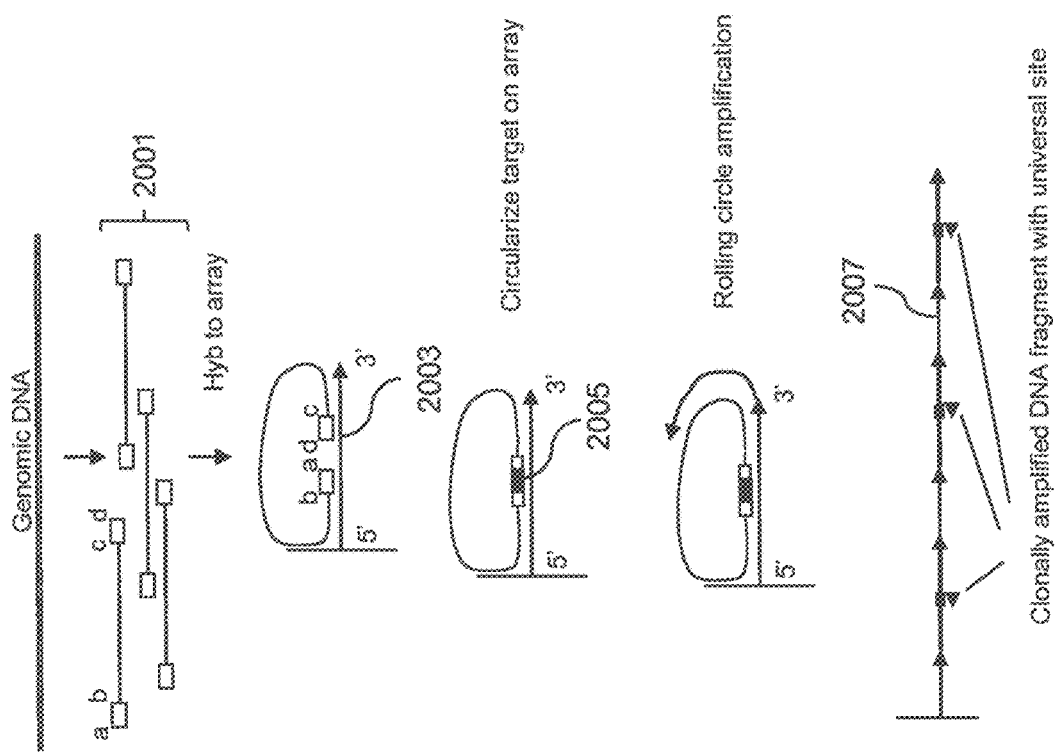
FIG. 18 shows the inversion of the ends of the fragments by hybridization to the array probe.

FIG. 18 shows a schematic of an embodiment. Genomic DNA is digested with restriction enzymes, for example, having a 4 base restriction recognition site. This generates double stranded fragments having two fragment ends. The individual single strands 2001 each have a 5' end (a) and a 3' end (d). The array probes 2003 are designed to be complementary to the ends of the target fragments but in an inverse manner. The 5' target region of a strand has a 5' and 3' end (a and b) and the 3' target region of a strand has a 5' and 3' region (c and d). In the target these are in the orientation a, b, c and d (from 5' to 3'). When the target is hybridized to the probe 2003 this is inverted and now the orientation is b, a, d, and c (3' to 5' in the figure). The common oligo 2005 is complementary to the central region of the array probe. When the target fragment hybridizes to the array probe and the common oligo hybridizes between the two ends of the target fragment a 2 step ligation can take place to form a circle that includes the target and the common oligo. The array probe may then be extended by RCA/RCR to generate a resulting extension product 2007 that has clonally amplified target with universal sites in between.

Common restriction enzymes may be used to define the target fragment locus. The probes of the array are designed to target fragments in the genome that are flanked by appropriate restriction sites. This may be combined with an upstream prep method where complexity is reduced using a WGSA approach. The fragments are generated with end-point restriction enzyme cutting reactions that are easier to perform than DNAse I random fragmentation.

Figure 19:
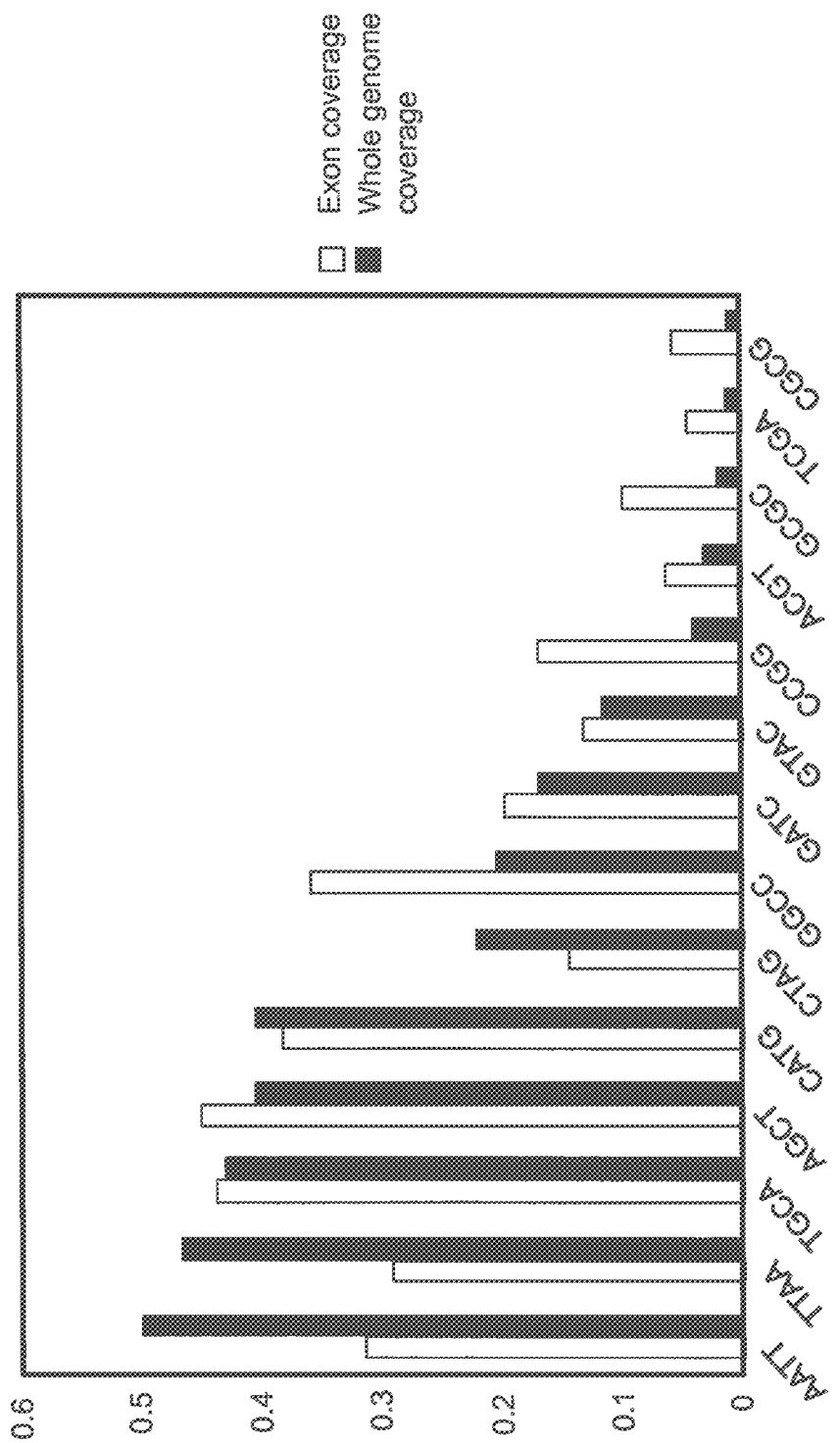
FIG. 19 shows distribution of genome coverage for fourteen 4 base recognition sequences.

FIG. 19 shows distribution of genome coverage for fourteen 4 base recognition sequences. There are 16 palindromic 4 base recognition sequences, 14 of which have commercial enzymes available from NEB and shown here. The fragment coverage of coding exons and all genomic DNA is computed for fragments between 80 and 350 bp. Shown here is single enzyme coverage. Multiple enzyme coverage can also be computed. Table 1 shows examples of genome partitioning with single or multiple enzymes.

TABLE 1

| Region | Coverage | Enzyme or Enzyme Combination |
|---|---|---|
| Exon coding region | 0.453 | AGCT |
| Chromosome 21 | 0.495 | AATT |
| Whole genome | 0.503 | AATT |
| Exon coding region | 0.687 | AGCT and TGCA |
| Chromosome 21 | 0.726 | AATT and TGCA |
| Exon coding region | 0.802 | AGCT, TGCA and CATG |
| Chromosome 21 | 0.834 | AATT, TGCA and AGCT |

The distribution of the enzyme recognition sites vary over different chromosomes. For example, for one combination chromosome 19 has the lowest coverage with only slightly higher than 90% and chromosome 5 is highest with over 96%. A calculation of coverage with restriction fragments generated using all 14 enzymes in separate reactions gives 97.59% coverage of the non-repetitive human genome, or 98.16% of coding exons. With 6 enzymes in the following 5 reactions, coverage is 95.70% of non-repetitive: (1) a multi-enzyme reaction of CATG and CTAG, (2) AATT, (3) TGCA, (4) AGCT, and (5) TTAA. This same combination covers about 92.12% of all coding exons. A different set of 6 enzymes (a multi-enzyme reaction of CATG and TTAA plus single enzyme reactions for AGCT, TGCA, AATT and GGCC) covers 94.95% of coding exons. With 7 enzymes in the following reactions: multi-enzyme reaction of CATG and TTAA, with single enzyme reactions of AGCT, TGCA, AATT, GGCC and CCGG, 96.12% of coding exons can be assayed. As will be clear to one of skill in the art, any number of enzymes and enzyme combinations can be used to optimize coverage of the genome or of specific genomic regions.

In some aspects arrays may be designed to test fragment length and position of inversion duplex ends on the array probe. The probes of the array are preferably attached to the array via the 5' end of the probe. A linker may be used to join the 5' end of the probes to the support. Methods for synthesizing arrays are well known in the art. In particular, methods for synthesizing arrays with free 3' ends are disclosed in US Pat. Pubs. 20090192050 and 20070265366. In some aspects the array probes are designed to be complementary to targets that are of predicted length and sequence based on in silico restriction digestion of the genome to be analyzed. The probes may be designed so that the targets hybridize to the probes so that the ends of the fragments form a double stranded region with the probe. Restriction digestion generates predictable strand ends so the array probe can be designed to have a region that is perfectly complementary to a region of the target. For example, if the target fragment has the following sequence 5' GTACC TCTCC ATCCT $N_x$ CTGAT CCTGT ACCTC 3' (SEQ ID No. 5) where $N_x$ is the central region of the target, then the target specific array probe for this target will have a 5' segment that is 5' AGGATGGAGAGGTAC//GAGGTA-CACAGGATCAG-3' (SEQ ID No. 6) wherein // indicates the fixed common sequence that is common to all target specific probes in the set. The ends of the fragment are perfectly complementary to the segment of the array probe, meaning that over the length of complementarity they form a duplex with no mismatches. The sequence of the target specific array probe is determined by the sequences at the ends of the strands of the target fragment. When restriction enzymes are used the ends of all of the targets may have some common sequences, that is the portion of the target that is part of the recognition sequence for the restriction enzyme may be the same in all or a plurality of the target sequences so the array probes. For example, if EcoRI is used the 5' end of the strands will have AATTC at the absolute end and the 3' ends will have G at the absolute end. Preferably the arrays will have more than 1,000, more than 10,000, more than 100,000 or more than 1,000,000 different target specific array probes each being present in a feature, so that the feature is a location that includes a plurality of copies of the same target specific array probe so that the majority of the full length probes in the feature are of the same sequence and specific for the same target sequence. The feature may overlap with other features to some degree or it may be largely discrete. The feature may be at a known or determinable location in the array. The feature can be a bead or a region of a support, for example.

Arrays were generated to test length and position. In one aspect the probe comprised a 5' portion of 31 bases, a central universal segment of 18 bases and a 3' region of 21 bases— this is referred to herein as "31-18-21" where the 31 is the length (in nucleotide bases) of the 5' region, the 18 is the length of the universal region and the 21 is the length of the 3' region, "5' region-universal-3' region". In some embodiments there may be additional segments included in the probe. The 5' region and the 3' region are complementary to the inverted ends of the target fragment. The central region is complementary to a selected oligonucleotide. The array was synthesized using a 7c3 (7 micron center to center feature spacing with 3 micron gap). Other combinations that were tested included 30-18-22, 35-18-17, 40-18-12, 30-18-12, and 25-18-17. These probes being either 70 or 60 bases in length. Experiments performed with oligonucleotide targets demonstrated the ability to hybridize and circularize, and perform RCA on the arrays. Genomic DNA targets were tested. Probes were selected for targets having TG/CA restriction fragments and being found on chromosome 21. Preferably about 90% of the targets are between 80 and 600 base pairs and about 10% are greater lengths, for example, 601 to 1000 bp. Preferably the targets do not contain repetitive sequence in the first 60 or last 60 base pairs. This array design may be used to test fragment length and position of inversion duplex ends on the probe. An example probe:

(SEQ ID NO. 7)
substrate-5'
gtc gtc aag atg cta ccg ttc agg att aga
tta tca tac tgg gct atc gca aca caa cca cct ctg ccg
a 3'.

The underlined sequence is the constant 18 mer central sequence. For each target, 5 different probe length and tag (constant central portion) positions were tested for both strands and tiled in 3 replicates. So for each target there were 30 features (3×2×5) on the array. The array tested had about 94,344 features so at 30 features per target approximately 3,145 target fragments could be tiled.

To test one disclosed approach, a circular DNA molecule was prepared and hybridized to the array. The experimental design is shown schematically in FIG. 7B. A circular target was designed to be complementary to control probes arranged in features in a known pattern on an Affymetrix GENECHIP array. The control oligonucleotides or "border oligos 948" were then extended using rolling circle amplification or not extended in a control reaction. After amplification, a labeled reporter oligonucleotide that has the same sequence as a region in the circular target (probe is complementary to the region of the extension product indicated by circle 811 and is the same sequence as the target in that region) and is thus complementary to a region in the amplification product was hybridized to the array. The hybridization pattern for the array with RCA is shown 813 and without RCA is shown 815. Results show a dramatic increase in the intensity of the reporter hybridization in the presence of RCA. The amplification observed on the array appears to be very robust.

Figure 8A:
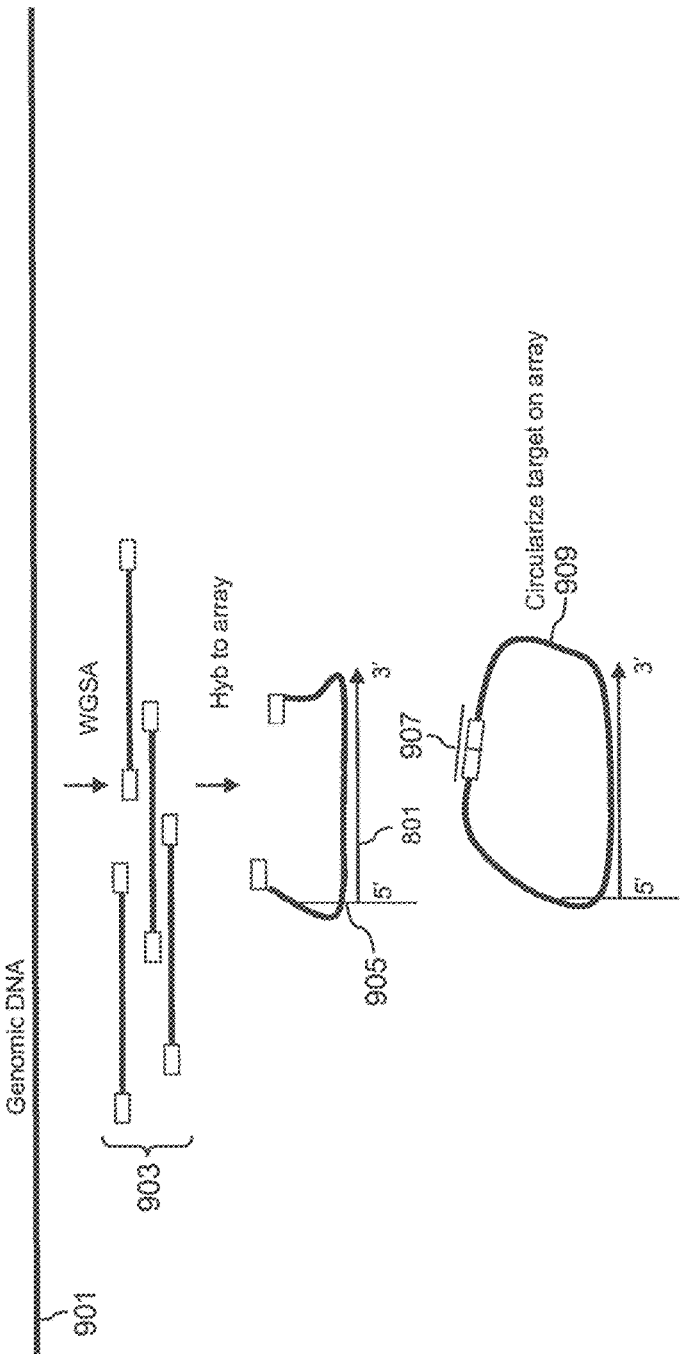
FIG. 8A shows a method for preparing genomic DNA for circularization and amplification using RCA on array.

FIG. 8 shows an example of how the method may be applied to analysis of genomic DNA. FIG. 8A shows the general scheme for target amplification. The genomic DNA 901 is fragmented and ligated to common adapter sequences to obtain fragments with common sequences at the 5' and 3' ends 903, for example, using the Affymetrix Whole Genome Sampling Assay (WGSA) described, for example, in Matsuzaki et al. *Nat. Methods.* 1(2):109-11, 2004 and Kennedy et al., *Nat. Biotechnol.* 21:1233-7 (2003). The adapter-ligated fragments are hybridized to an array of target specific probes 905 that are attached to a solid support so that the 3' end is free for extension. The targets are circularized by ligation mediated by a splint 907 that is complementary to the common adapter sequences. The probe is extended to obtain an extension product 911.

Figure 8B:
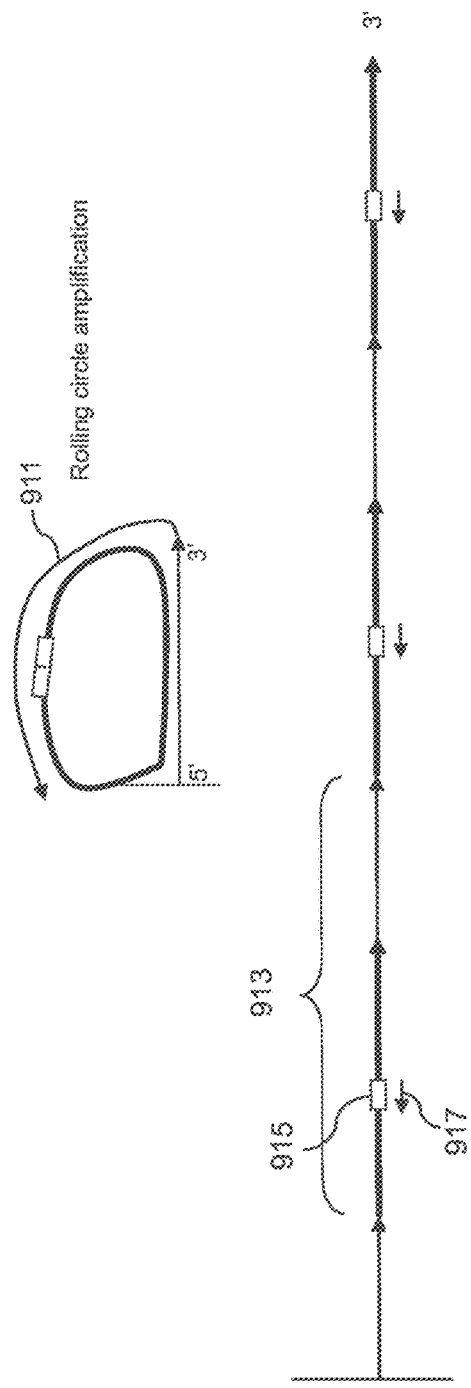
FIG. 8B shows the extension product 911 in greater detail.
Figure 9:
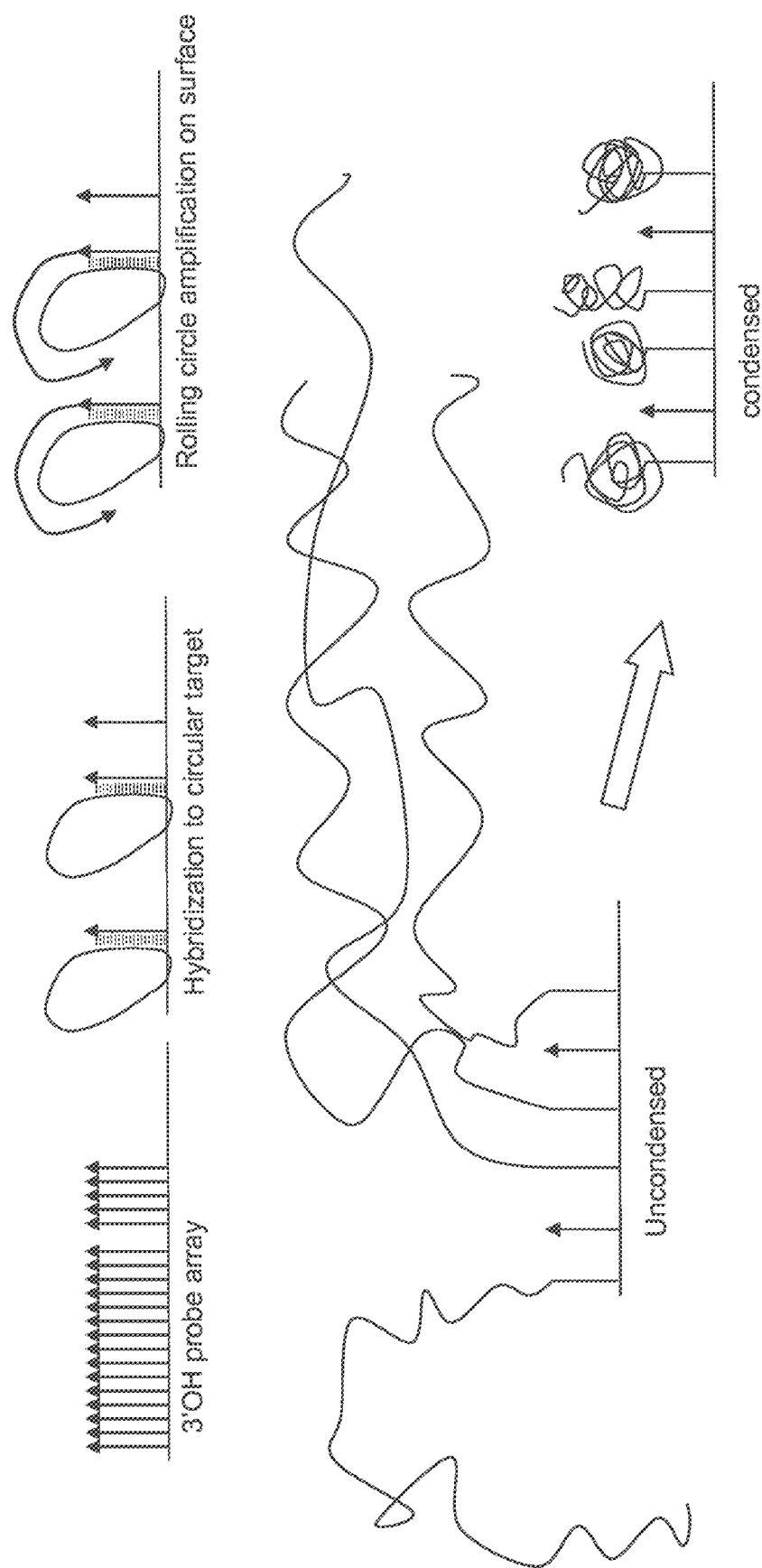
FIG. 9 shows a schematic of how amplified targets might invade into neighboring features or cells and a preferred alternative whereby the amplified target can be condensed to achieve feature localization.

FIG. 8B shows the extension product 911 in greater detail. The product that is formed by the RCA has multiple copies (1 complete copy is identified by bracket 913) of the complement of the circularized target 909. The extension product includes the following from left to right: the probe sequence at the 5' end and then multiple copies of the complement of the target circle. The complement of the adapter region 915 can be used for hybridization of a probe 917 for amplification, detection or further analysis. In some embodiments the probe includes a detectable label such as biotin or a fluorescent label or a quantum dot and hybridization of the probe can be detected to determine the presence of the target in the starting sample or to quantify the amount of any given target in the starting sample, such as in a gene expression profiling assay. In another embodiment the probe can be used as a primer and can be extended in a template directed way. This may be used, for example, to determine the sequence of the target by determining the sequence of the extension product. For methods for sequencing that may be used in combination with the disclosed methods see, for example, US20090176234. Methods that may be used include, for example, sequencing by synthesis as described in U.S. Pat. No. 5,547,839. In another embodiment the probe can be extended by ligation of one or more nucleotides to the end in a template dependent manner in a sequencing by ligation assay.

In one aspect the probes of the array are target specific and contain a region of complementarity to selected targets that is between 15 and 100 bases, more preferably between 20 and 50 and more preferably between 20 and 30. In some embodiments the probes of the array are about 25 bases in length or between 20 and 30 bases in length. In preferred aspects the arrays contain more than 1,000,000 different target specific probes and more preferably contain 1,000,000 to 5,000,000 different target specific probes. In some aspects the array may contain 5 million to 10 million different target specific probes. The density of the features of the array is preferably greater than 1000 features per square cm and more preferably greater than 10,000 features per square cm. A feature generally is an area containing probes directed at the same target. Many of the probes in the feature have the same sequence. In preferred aspects the most abundant probe in a feature is the full length target specific probe. A feature may be an area on a single solid support or it may be a bead in solution or a bead attached or associated with a solid support.

The examples demonstrate that RCA with strand displacing polymerase can be performed on GENECHIP Arrays with 3' OH up probes. RCA templates can be hybridized as linear DNA molecules with inverted ends that can be ligated subsequently using T4 DNA ligase on the array to form closed circular templates. RCA products are long DNA strands that stretch beyond a single cell feature on the array, complicating intensity extraction. However, in the presence of certain cationic solutions, the long RCA DNA products condense and pack into singular feature cells, enabling accurate intensity determination.

FIG. 20 shows a schematic for sequencing with terminal ligation probes. The RCA product 2201 having multiple binding sites 2203 for a common primer 2205 is hybridized with the common primer and ligation probes 2207 having a label specific for the terminal base (a terminal T in the first ligation labeled with Cy3, for example). The ligation probes are differentially labeled according to the base at the 3' terminus, for example, FAM-N8A, Cy3-N8T, Cy3.5-N8G and Cy5-N8C, where "N8" refers to a sequence that is a random sequence of 8 bases in length which is followed by a single position that is fixed. Other labels such as ROX and JOE may also be used for the ligation probes. As shown in the example, when the first base to be interrogated in the target is an "A" the Cy3-N8T should be ligated to the 5' end of the common primer. This forms a ligation product that includes the common primer 2205 ligated to the ligation probe 2207 that has a terminal base that is complementary to the interrogation position. The entire ligation product is removed and a second "plus 1" or "+1" primer 2209 is hybridized in a second round of ligation. The +1 primer has the same sequence as the common primer sequence with a single N at the 5' end. A second ligation probe is ligated to the end of the +1 primer, again labeled specific for the terminal base (a C in the example or Cy5-N8C). The newly generated ligation product is then removed and a primer "plus 2" or "+2" 2211 is added. The +2 has NN at the 5' end. This is repeated over as many cycles as desired bases to be sequenced, each time an additional N is added to the end of the common primer. A single base of the sequence is determined at each cycle. Preferably the 3' end of the ligation probes are blocked from ligation so that two ligation probes don't ligate to each other in a single step.

As the read length increases the accuracy of the read out may in some aspects decline. The signal degrades as a result of, for example, dephasing, with progressive cycles. Read lengths of about 10 bases are generally quite robust. Longer reads, for example, out to 20 bases or longer are also feasible.

Examples of cyclic reversible terminators (CRTs) that may be used in some embodiments disclosed herein have been described, for example, in Wu et al. Nuc. Acids. Res. 35(19):6339-6349 (2007), which is incorporated herein by reference, and provides methods for terminating DNA synthesis by $N^6$-alkylated photocleavable 2'-deoxyadenosine triphosphates. Useful reagents include 6-FAM labeled $C^7$-($\alpha$-isopropyl-2-nitrobenzyl-oxymethyl)-dATP, 6-JOE labeled 5-($\alpha$-isopropyl-2-nitrobenzyl-oxymethyl)-dUTP, 6-ROX labeled $C^7$-($\alpha$-isopropyl-2-nitrobenzyl-oxymethyl)-dGTP, and Cy5 labeled 5-($\alpha$-isopropyl-2-nitrobenzyl-oxymethyl)-dCTP.

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

We claim:

1. A method for amplifying a plurality of target sequences from a nucleic acid sample and analyzing the amplified target sequences, the method comprising:
   (a) mixing the nucleic acid sample with (a1) an array of probes arranged in features and (a2) a plurality of oligonucleotides,
   wherein the nucleic acid sample comprises target fragments comprising target sequences,
   each feature comprises multiple copies of a target specific array probe having (i) a first probe region that is complementary to a first target region, (ii) a second probe region that is complementary to a second target region, and (iii) a central probe region that is complementary to one of the oligonucleotides, said central probe region being between the first and second probe regions,
   the target fragments hybridize to complementary target specific array probes to form probe:target fragment complexes, and
   in the probe:target fragment complexes, the first target region hybridizes to the first probe region, the second target region hybridizes to the second probe region, and the oligonucleotide hybridizes to the central probe region;
   (b) joining the first target region, the oligonucleotide, and the second target region that hybridize to the same array probe to form a target circle;
   (c) extending the array probe using the target circle as a template, thereby obtaining an extended array probe comprising a plurality of copies of the complement of the target sequences; and
   (d) analyzing the copies.

2. The method of claim 1, wherein the plurality of target sequences comprises between 100 and 3,000,000 different target sequences.

3. The method of claim 1, wherein said (d) analyzing further comprises one or more selected from the group consisting of: (1) determining the genotype of a one or more polymorphisms in the target sequences in the nucleic acid sample; (2) determining the methylation status of one or more cytosines in the target sequences in the nucleic acid sample; and (3) determining the presence or absence of specific target sequences in the nucleic acid sample.

4. The method of claim 1, wherein said (b) joining comprises ligating the 5' end of the target fragment to the 3' end of the oligonucleotide and ligating the 3' end of the target fragment to the 5' end of the oligonucleotide.

5. The method of claim 1, wherein the extended array probe comprises a plurality of copies of the complement of the oligonucleotide.

6. The method of claim 1, wherein the oligonucleotide comprises a sequence complementary to a universal priming site and wherein the extended array probe comprises a plurality of copies of the universal priming site.

7. The method of claim 1, wherein the oligonucleotide is from 12 to 30 bases.

8. The method of claim 1, wherein the central probe region of the array probe is from 10 to 30 bases.

9. The method of claim 1, wherein the central probe region is common to each target specific array probe in the plurality of target specific array probes.

10. The method of claim 1, wherein the central probe region of the array probe is flanked by a 5' region and a 3' region and wherein the 5' region is complementary to a region at or near the 5' end of the target fragment and the 3' region is complementary to a region at or near the 3' end of the target fragment.

11. The method of claim 1, wherein the method further comprises fragmenting the nucleic acid sample.

12. The method of claim 11, wherein the fragmenting is by cleavage with one or more restriction fragments.

13. The method of claim 12, wherein a plurality of restriction fragments is selected to provide fragments of a selected size that cover at least 80% of a selected genome.

14. The method of claim 1, wherein said (d) analyzing comprises hybridizing a universal primer to the universal priming site and extending the universal primer by at least one base, wherein the identity of the at least one base is determined.

15. The method of claim 14, wherein said extending the universal primer comprises ligating an oligonucleotide to the primer.

16. The method of claim 14, wherein said extending the universal primer comprises (i) adding a nucleotide comprising a removable label and a reversible terminator to the end of the primer, (ii) detecting the label and (iii) thereby determining the identity of the nucleotide added, (iv) removing the label and the reversible terminator and optionally (v) repeating steps (i) to (iv) at least once.

17. The method of claim 1, wherein the target fragment hybridizes to the array probe so that a single stranded overhang of the target fragment is generated and wherein a nuclease that recognizes the overhang is used to remove the overhang.

* * * * *